United States Patent
Nunn et al.

(10) Patent No.: US 11,730,792 B2
(45) Date of Patent: Aug. 22, 2023

(54) COVERSIN (OMCI) FOR THE TREATMENT OF AUTOIMMUNE BLISTERING DISEASES: BULLOUS PEMPHIGOID (BP) AND EPIDERMOLYSIS BULLOSA ACQUISITA (EBA)

(71) Applicant: VOLUTION IMMUNO PHARMACEUTICALS SA, Geneva (CH)

(72) Inventors: Miles Andrew Nunn, Geneva (CH); Brihad Abhyankar, Geneva (CH); Christian David Sadik, Lubeck (DE)

(73) Assignee: Volution Immuno Pharmaceuticals SA, Geneva (CH)

( * ) Notice: Subject to any disclaimer, the term of this patent is extended or adjusted under 35 U.S.C. 154(b) by 548 days.

(21) Appl. No.: 16/603,352

(22) PCT Filed: Apr. 20, 2018

(86) PCT No.: PCT/EP2018/060241
§ 371 (c)(1),
(2) Date: Oct. 7, 2019

(87) PCT Pub. No.: WO2018/193122
PCT Pub. Date: Oct. 25, 2018

(65) Prior Publication Data
US 2020/0113971 A1    Apr. 16, 2020

(30) Foreign Application Priority Data

Apr. 21, 2017 (GB) .................... 1706404
Apr. 21, 2017 (GB) .................... 1706406
Apr. 24, 2017 (GB) .................... 1706452

(51) Int. Cl.
*A61K 38/17*    (2006.01)
*A61P 17/00*    (2006.01)
(Continued)

(52) U.S. Cl.
CPC ........ *A61K 38/1767* (2013.01); *A61K 9/0019* (2013.01); *A61K 31/56* (2013.01); *A61K 48/005* (2013.01); *A61P 17/00* (2018.01)

(58) Field of Classification Search
CPC combination set(s) only.
See application file for complete search history.

(56) References Cited

U.S. PATENT DOCUMENTS

2010/0105611 A1* 4/2010 Hamer .................. A61P 31/10
514/6.9
2010/0292130 A1* 11/2010 Skerra .................. A61P 35/00
435/325

(Continued)

FOREIGN PATENT DOCUMENTS

EP    1739078 A1    1/2007
EP    2173890 B1    3/2011
(Continued)

OTHER PUBLICATIONS

Yoshioka, Chest; 141(3): 795-797. (Year: 2012).*
(Continued)

*Primary Examiner* — Kevin S Orwig
*Assistant Examiner* — John Michael Cronin
(74) *Attorney, Agent, or Firm* — McNeill Baur PLLC

(57) ABSTRACT

The present invention relates to methods of treating or preventing AIBD.

21 Claims, 12 Drawing Sheets

Specification includes a Sequence Listing.

(51) Int. Cl.
    A61K 9/00       (2006.01)
    A61K 31/56      (2006.01)
    A61K 48/00      (2006.01)

(56) References Cited

U.S. PATENT DOCUMENTS

| | | | |
|---|---|---|---|
| 2011/0059885 A1* | 3/2011 | Lea | A61P 19/06 514/1.9 |
| 2012/0115773 A1* | 5/2012 | Nunn | A61P 37/02 435/254.11 |
| 2020/0113971 A1 | 4/2020 | Nunn et al. | |
| 2020/0385434 A1 | 12/2020 | Nunn | |
| 2021/0113658 A1 | 4/2021 | Weston-Davies | |

FOREIGN PATENT DOCUMENTS

| | | | | |
|---|---|---|---|---|
| JP | 2011511632 A | | 4/2011 | |
| WO | WO 95/29697 | * | 11/1995 | A61K 38/36 |
| WO | 2004106369 A2 | | 12/2004 | |
| WO | 2006128670 A1 | | 12/2006 | |
| WO | 2007028968 A1 | | 3/2007 | |
| WO | 2007095230 A2 | | 8/2007 | |
| WO | 2007028968 A9 | | 6/2008 | |
| WO | 2008113834 A2 | | 9/2008 | |
| WO | 2009098454 A2 | | 8/2009 | |
| WO | 2010100396 A1 | | 9/2010 | |
| WO | 2010151526 A1 | | 12/2010 | |
| WO | 2011056972 A2 | | 5/2011 | |
| WO | 2011083317 A1 | | 7/2011 | |
| WO | 2012178083 A1 | | 12/2012 | |
| WO | 2014047500 A1 | | 3/2014 | |
| WO | 2014160958 A1 | | 10/2014 | |
| WO | WO-2014160958 A1 | * | 10/2014 | A61K 31/7105 |
| WO | 2015185760 A1 | | 12/2015 | |
| WO | 2015185945 A2 | | 12/2015 | |
| WO | WO-2015185760 A1 | * | 12/2015 | A61K 38/17 |
| WO | 2016123371 A1 | | 8/2016 | |
| WO | 2016094834 A3 | | 10/2016 | |
| WO | 2016198133 A1 | | 12/2016 | |
| WO | 2016200627 A1 | | 12/2016 | |
| WO | 2016201301 A1 | | 12/2016 | |
| WO | 2017044811 A1 | | 3/2017 | |
| WO | 2018193120 A1 | | 10/2018 | |
| WO | 2018193122 A1 | | 10/2018 | |

OTHER PUBLICATIONS

Venning, British Journal of Dermatology; 167, pp. 1200-1214 (Year: 2012).*
Murrell, Blistering Diseases, Springer-Verlag Berlin Heidelberg. (Year: 2015).*
Clinical Pharmacokinetics of Prednisone and Prednisolone SpringerLink_Published Dec. 15, 2012, https://link.springer.com/article/10.2165/00003088-197904020-00004, generated by examiner Oct. 25, 2022 (Year: 2012).*
Bullous Pemphigoid_Nov.13, 2016, https://web.archive.org/web/20161113050120/https://rarediseases.org/rare-diseases/bullous-pemphigoid/, generated by examiner on Oct. 24, 2022. (Year: 2016).*
Pemphigus_Published_Apr. 24, 2016, https://web.archive.org/web/20160424182953/https://rarediseases.org/rare-diseases/, generated by examiner on Oct. 24, 2022. (Year: 2016).*
Epidermolysis Bullosa_Published_Feb. 19, 2017, https://web.archive.org/web/20170219083638/https://rarediseases.org/rare-diseases/epidermolysis-bullosa/, generated by examiner on Oct. 24, 2022. (Year: 2017).*
Anonymous, "Akari Therapeutics Announces Completion of Phase II Cobalt Trial of Coversin in Patients with PNH and Further Progress of Clinical Trials," 6 pages (2018).
Anonymous, "Akari Therapeutics—Coversin matches Soliris in Phase II" Retrieved from the Internet on Jun. 20, 2018: www.researchpool.com/download/?report id=I29517I&show pdf data=true, 9 pages, (2017).
Anonymous, "Akari Therapeutics Apr. 2017", Forward-Looking Statement, 26 pages. (2017).
Anonymous, "Akari Therapeutics ASH data highlight Conversin's unique properites," Edison Clinical Update, 8 pages, (Jan. 9, 2017).
Anonymous, "Akari Therapeutics Demonstrates Positive Response with Coversin in Ongoing Phase 2 PNH Trial and In Additional Clinical Targets," 4 pages (2017).
Anonymous, "Clinical trial 2017-002836-18," Jan. 24, 2018, retrieved from the Internet: www.clinicaltrialsregister.eu/ctr-search/trial/2017-002836-18/NL on Jun. 20, 2018, 5 pages (2018).
Ausubel et al, "Identification of Signal Transduction Pathways Leading to the Expression of *Arabidopsis thaliana* Defense Genes," Advances in Molecular Genetics of Plant-Microbe Interactions, vol. 1, pp. 357-364 (1991).
Bağci et al., "Bullous pemphigoid," Autoimmunity Reviews 16, pp. 445-455 (2017).
Breustedt et al., "Comparative ligand-binding analysis of ten human lipocalins," Biochim Biophys Acta 1764, pp. 161-173 (2006).
Chen et al., "Neutrophil-derived leukotriene B4 is required for inflammatory arthritis," J. Exp. Med., vol. 203, No. 4, pp. 337-842 (Apr. 17, 2006).
Curry et al. "Nonsteroidal Antiinflammatory Drugs: A Review," Journal of the American Animal Hospital Association vol. 41, pp. 298-309 (2005).
Del Prete et al., "Regulation of dendritic cell migration and adaptive immune response by leukotriene B4 receptors: a role for LTB4 in up-regulation of CCR7 expression and function," Blood, vol. 109, pp. 626-631 (2007).
Dube et al., "Zileuton: the first leukotriene inhibitor for use in the management of chronic asthma," Five-lipoxygenase Products in Asthma. New York, NY: Marcel Dekkar, Inc, pp. 391-428 (1998).
Ford-Hutchinson, "Leukotriene B4 in Inflammation," Crit. Rev. Immunol. vol. 10, pp. 1-12 (1990).
Guo et al., "Role of C5A in Inflammatory Responses,", Annu Rev Immunol, 23: pp. 821-852 (2005).
Harrison et al., "Isoleukotrienes Are Bilogically Active Free Radical Products of Lipid," 1995, J. Biol. Chem. vol. 270, No. 29,pp. 17273-17276 (Jul. 21, 1995).
Heimbach et al. "The C5a Receptor on Mast Cells Is Critical for the Autoimmune Skin-blistering Disease Bullous Pemphigoid" Journal of Biological Chemistry, vol. 286, No. 17, pp. 15003-15009 (2011).
Hellberg et al., "Methylprednisolone Blocks Autoantibody-Induced Tissue Damage in Experimental Models of Bullous Pemphigoid and Epidermolysis Bullosa Acquisita through Inhibition of Neutrophil Activation," Journal of Investigative Dermatology, 133, pp. 2390-2399 (2013).
Hoover et al,. "Leukotriene B4 action on endothelium mediates augmented neutrophil/endothelial adhesion," Proc. Nati. Acad. Sci. USAvol. 81, pp. 2191-2193 (Apr. 1984).
International Search Report and Written Opinion of International Application No. PCT/EP2018/060241,dated Sep. 26, 2018 (37 pages).
Jore et al., "Structural basis for therapeutic inhibition of complement CS," Nat Struct Mol Biol., 23(5): pp. 378-386 (May 2016).
Kaplan "Eculizumab (Alexion)" Current Opinion in Investigational drugs, vol. 3, No. 7, pp. 1017-1023 (2002).
Karsten et al. "Tissue Destruction in Bullous Pemphigoid Can Be Complement Independent and May Be Mitigated by C5aR2," Frontiers in Immunology, vol. 9, Article 488, 12 pages (Mar. 2018).
Kilchenstein et al. "Galactosylated IgGI immune complexes diminish C5a-dependent inflammation in experimental Epidermolysis Bullosa Acquisita" Abstracts, Immunobiology 217, pp. 1129-1222 (2012).
Kim et al., A unique requirement for the leukotriene B4 receptor BLT1 for neutrophil recruitment in infl ammatory arthritis J. Exp. Med. vol. 203, pp. 829-835 (Apr. 17, 2006).
Kim et al., "Regulation of Immune Cells by Eicosanoid Receptors," The Scientific World Journal 7, pp. 1307-1328 (2007).
Kirtschig et al., "Interventions for bullous pemphigoid: a summarised Cochrane Review," Cochrane Database of Systematic Reviews 2010, Issue 10, Art. No. CD002292, pp. 449-450, (2010).

(56) References Cited

OTHER PUBLICATIONS

Klaas et al., "Neutrophils mediate immune modulation of dendritic cells through glycosylationdependent interactions between Mac-1 and DC-SIGN," J. Exp. Med., vol. 201, No. 8, pp. 1281-1292 (2005).
Kuhn et al., "PASylated Coversin, a C5-Specific Complement Inhibitor with Extended Pharmacokinetics, Shows Enhanced Anti-Hemolytic Activity in Vitro," Bioconjugate Chem., 27 (10), pp. 2359-2371 (2016).
Leonardi, "Allergy and allergic mediators in tears," Experimental Eye Research xxx 12 pages (Jul. 29, 2013).
Liu et al., "The Role of Complement in Experimental Bullous Pemphigoid," The Journal of Clinical Investigation, vol. 95, pp. 1539-1544 (Apr. 1995).
Lundeen et al., Leukotriene B4 Receptors BLT1 and BLT2: Expression and Function in Human and Murine Mast Cells. J Immunol. 177, pp. 3439-3447 (2006).
Mihai et al. "Specific inhibition of complement activation significantly ameliorates autoimmune blistering disease in mice" Abstracts/ Molecular Immunology, vol. 48, pp. 1666-1733 (2011).
Mihai et al. "Specific inhibition of complement activation significantly ameliorates autoimmune blistering disease in mice" Frontiers in Immunology, vol. 9, Article 535, 11 pages (Mar. 16, 2008).
Miyahara et al. "Role of the LTB4BLT1 Pathway in Allergen-induced Airway Hyperresponsiveness and Inflammation," Allergology International. 55, pp. 91-97 (2006).
Murrell et al. Definitions and outcome measures for bullous pemphigoid: Recommendations by an international panel of experts. J Am Acad Dermatol. 66(3): pp. 479-485 (Mar. 2012).
Nishimura et al., "Genetic Variants in C5 and Poor Response to Eculizumab," New Engl J. Med., 30;7: pp. 632-639 (Feb. 13, 2014).
Noiri et al., "An in vivo approach showing the chemotactic activity of leukotriene B4 in acute renal ischemic-reperfusion injury," Proc Nat Acad Sci USA vol. 97, No. 2, pp. 823-828 (Jan. 18, 2000).
Nomura et al., "Treatment of bullous pemphigoid with a leukotriene receptor antagonist," Allergy, 58: pp. 162-163 (2003).
Ricklin et al., "Complement-targeted therapeutics," Nature Biotechnology, 25: pp. 1265-1275 (2007).
Roversi et al., "Bifunctional Lipocalin Ameliorates Murine Immune Complex-induced Acute Lung Injury," Journal of Biological Chemistry, vol. 288 (26) pp. 18789-18802 (Jun. 28, 2013).
Sadik et al. "Neutrophils cascading their way to inflammation" Trends Immunol., 32(10): pp. 452-460 (Oct. 2011).
Showell et al., "The In Vitro and In Vivo Pharmacologic Activity of the Potent and Selective Leukotriene B4 Receptor Antagonist CP-1 05696," the Journal of Pharmacology and Experimental Therapeutics, vol. 273, No. 1 pp. 176-184 (1995).
Schlapschy et al., "PASylation: a biological alternative to PEGylation for extending the plasma half-life of pharmaceutically active proteins," Protein Eng Des Sel. vol. 26, No. 8, pp. 489-501 (2013).
Schmidt et al., "The Diagnosis and Treatment of Autoimmune Blistering Skin Diseases," Dtsch Arztebl Int.,108(23): pp. 399-405 (2011).
Sebaldt et al., "Inhibition of eicosanoid biosynthesis by glucocorticoids in humans," Proc Natl Acad Sci. Vol. 87, pp. 6974-6978 (Sep. 1990).
Sezin T, et al., "The Leukotriene B4 and Its Receptor BL Tl Act as Critical Drivers of Neutrophil Recruitment in Murine Bullous Pemphigoid-Like Epidermolysis Bullosa Acquisita," J Invest Dermatol., 137(5): pp. 1104-1113 (2017).
Sezin, T., "The Role of Leukotriene B4 and Its Receptor BLT1 in Pathogenesis of Autoantibody-Induced Skin Inflammation," Dissertationfor Fulfillment of Requirements for the Doctoral Degree of the University of Lubeck, 153 pages( 2016).
Shao et al.,"Targeted Disruption of Leukotriene B4 Receptors BLT1 and BLT2: A Critical Role for BLT1 in Collagen-Induced Arthritis in Mice," J. Immunol, 176, pp. 6254-6261 (2006).
Sharma et al., "The role of leukotrienes in the pathophysiology of inflammatory disorders: Is there a case for revisiting leukotrienes as therapeutic targets?" Inflammopharmacology 14 pp. 10-16 (2006).

Anonymous, "Akari Therapeutics Announces Initiation of Pivotal Phase III Trial of Nomacopan in Bullous Pemphigoid (BP)," Apr. 12, 2021 (6 pages).
Chakievska et al., "IL-17A is functionally relevant and a potential therapeutic target in bullous pemphigoid," Journal of Autoimmunity, 96, (2019) pp. 104-112 (9 pages).
Horvath et al., "POSTER: A Phase II Clinical Trial of Safety and Efficacy of Nomacopan (rVA576) in Adult Mild to moderate Bullous Pemphigoid Patients," 4th Annual Emirates Dermatology Society Conference, Nov. 19-21, 2020 (1 page).
Karsten et al., "Galactosylated IgG1 links FcγRIIB and Dectin-1 to block complement-mediated inflammation," Nat Med. Sep. 2012; 18(9): 1401-1406 (21 pages).
Kasperkiewicz et al., "Genetic identification and functional validation of FcγRIV as key molecule in autoantibody-induced tissue injury," J Pathol 2012; 228: 8-19 (12 pages).
Muller et all., "Dimethylfumarate Impairs Neutrophil Functions," Journal of Investigative Dermatology (2016) 136, 117-126 (10 pages).
Nunn et al., POSTER: "Disease Remission During a Short-term Treatment Phase II Study of Nomacopan in Mild-to-moderate Bullous Pemphigoid—with Final Plan for Phase III Trial," American Academy of Dermatology Association (AAD) Virtual Meeting Experience (VMX) 2021, Apr. 23-25, 2021.
Schulze et al., "Fcγ Receptors III and IV Mediate Tissue Destruction in a Novel Adult Mouse Model of Bullous Pemphigoid," The American Journal of Pathology, vol. 184, No. 8, Aug. 2014 (12 pages).
Sezin et al., "Dual inhibition of complement factor 5 and leukotriene B4 synergistically suppresses murine pemphigoid disease," JCI Insight 2019;4(15):e128239 (13 pages).
Anonymous, "Akari Therapeutics Announces Completion of Phase II COBALT Trial of Coversin in Patients with PNH and Further Progress of Clinical Trials—Akari Therapeutics," Feb. 6, 2016, 6 pages. Retrieved from the internet on Jun. 6, 2018: https://www.akaritx.com/2018/02/06/akari-therapeutics-announces-completion-phase-ii-cobalt-trial-coversin-patients-pnh-progress-clinical-trials/.
Anonymous, Atopic Keratoconjunctivitis Management: Diagnosis and Management, Aug. 1, 2016 (15 pages). Retrieved on Jun. 17, 2021: https://www.aimu.us/2016/08/01/atopic-keratoconjunctivitis-diagnosis-and-management/.
Anonymous, "TSGP2," Database UniProt [Online], Database Accession No. Q8I9U1, Oct. 5, 2016, 1 page.
Calder et al., "Experimental immune-meditated conjunctivitis (EIC): downregulation by Coversin, a dual C5 and LTB4 inhibitor," Annual Meeting of the Association for Research in Vision and Opthamology, vol. 59, May 3, 2018, p. 507 (2 pages).
Simon et al., Glucocorticoids in Autoimmune Bullous Diseases: Are Neutrophils the Key Cellular Target? Journal of Investigative Dermatology 133, pp. 2314-2315 (2013).
Sitaru et al., "Induction of dermal-epidermal separation in mice by passive transfer of antibodies specific to type VII collagen," J Clin Invest., vol. 115, No. 4, pp. 870-878 (2005).
Tager et al., "BLT1 and BLT2: the leukotriene B4 receptors," Prostaglandins Leukot. Essent. Fatty Acids, 69, pp. 123-134 (2003).
Taube et al., The Leukotriene B4 Receptor (BLT1) Is Required for Effector CD8+ T Cell-Mediated, Mast Cell-Dependent AirwayHyperresponsiveness, J. Immunol. 176, pp. 3157-3164 (2006).
Terpe, K., "Overview of tag protein fusions: from molecular and biochemical fundamentals to commercial systems," Appl Microbiol Biotechnol, 60, pp. 523-533 (2003).
Ujiie et al., "Bullous Pemphigoid Autoantibodies Directly Induce Blister Formation without Complement Activation," J Immunol., 193: pp. 4415-4428 (2014).
Venning et al., "British Association of Dermatologists' guidelines for the management of bullous pemphigoid" British Journal of Dermatology, vol. 167, Issue 6, pp. 1200-1214 (Dec. 2012).
Yamaoka et al., "Leukotrine B4 Enhances Activation, Proliferation, and Differntiation of Human B Lymphocytes," J. Immunol. vol. 143, pp. 1996-2000 (1989).
Yokomizo et al., "A Second Leukotriene B4 Receptor, BLT2: A New Therapeutic Target in Inflammation and Immunological Disorders," J. Exp. Med. vol. 192, No. 3, pp. 421-432 (Aug. 7, 2000).

(56) References Cited

OTHER PUBLICATIONS

Yokomizo et al., "AG-protein-coupled receptor for leukotriene B4 that mediates chemotaxis," Nature vol. 387, pp. 620-624 (Jun. 5, 1997).
Yokomizo et al., "Hydroxyeicosanoids Bind to and Activate the Low Affinity Leukotriene B4 Receptor, BLT2," J. Biol. Chem. vol. 276, No. 15, pp. 12454-12459 (Apr. 13, 2001).
Communication pursuant to Article 94(3) EPC for European Patent Application No. 18726731.5, dated Mar. 12, 2021 (21 pages).
Mooney et al., "Studies on Complement Deposits in Epidermolysis Bullosa Acquisita and Bullous Pemphigoid", Archives of Dermatology, vol. 128, No. 1, 1992, pp. 58-60 (3 pages).
Nunn et al., "Therapeutic Development of Complement C5 Inhibitor Coversin (TM) with Extended Half-Life Via PASylation (R)," Biosis, Biosciences Information Service, Philadelphia, PA,US, Dec. 2, 2016 (2 pages).
Sadik et al., "Evaluation of Nomacopan for Treatment of Bullous Pemphigoid A Phase 2a Nonrandomized Controlled Trial," JAMA Dermatol, doi:10.1001/jamadermatol.2022.1156; May 4, 2022, pp. E1-E9 (9 pages).
Anonymous: "A teary-eyed look for clues about an autoimmune disease" www.dgiwire.com, 2 pages (Aug. 26, 2016).
Anonymous: "Akari Therapeutics: Sjorgen's dry eye," www.akaritx.com/sjorgen, 2 pages, Apr. 2017.
Roshwalb,G., "Coversin: A Novel Complement Inhibitor for Inflammatory and Autoimmune Disease" Drug Discovery and Development 8 pages (Oct. 21, 2016).
Schmidt et al., "Pemphigoid diseases," Lancet vol. 381, Jan. 26, 2013; pp. 320-332 (13 pages).
Anonymous; Internet Archive Wayback Machine: Epidermolysis Bullosa Acquista; retrieved from the internet on Jan. 25, 2023: https://web.archive.org/web/20161215012616/https://rarediseases.info.nih.gov/diseases/6360/epidermolysis-bullosa-acquisita (8 pages).
Tanaka et al., "Topical Treatment Of Oral Mucosal Lesions Of Autoimmune Hydroa With Corticosteroids," Journal of the Nichipi Society, 110(9), p. 1403-1410 (2000).

* cited by examiner

FIG. 2A

```
ATGCTGGTTTGGTGACCCTGATTTCTTCTTTTGCGAACATCGCATATGCTGACAGC    60
 M  L  V  V  T  L  I  F  S  F  A  N  I  A  Y  A  D  S       20
GAAAGCGACTGCACTGGAAGCGTTGAACCTGTTGAGCGTTCCAAGCTTCAGTGAGGCAAA  120
 E  S  D  C  T  G  S  B  P  V  D  A  F  Q  A  F  S  E  G  K   40
GAGGCATATGTCCTGGTGAGGTCCACGGATCCCAAGGCCGAGGACTGCTTGAAAGGAGAA  180
 E  A  Y  V  L  V  R  S  T  D  P  K  A  R  D  C  L  K  G  E   60
CCAGCCGGAGAAAAGCAGGACAACACGTTGCCGGTGATGACGTTTAAGAATGGCACA    240
 P  A  G  E  K  Q  D  N  T  L  P  V  M  M  T  F  K  N  G  T   80
GACTGGGCTTCAACGGATTGGACGTTTACTTTGGACGGCGCAAAGGTAACGGCAACCCTT  300
 D  W  A  S  T  D  W  T  F  T  L  D  G  A  K  V  T  A  T  L  100
GGTAACCTAACCCAAAATAGGGAAGTCGTCTACGACTCGCAAAGTCATCACTGCCACGTT  360
 G  N  L  T  Q  N  R  E  V  V  Y  D  S  Q  S  H  H  C  H  V  120
GACAAGGTCGAGAAGGAAGTTCCAGATTATGAGATGATGCTCGATGCGGGAGGGCTT    420
 D  K  V  E  K  E  V  P  D  Y  E  M  M  L  D  A  G  G  L    140
GAAGTGGAAGTCGAGTGCTGCCGTCAAAAGCTTGAAGAGTTGGCGTCTGGCAGAACCAA  480
 E  V  E  V  E  C  C  R  Q  K  L  E  E  L  A  S  G  R  N  Q  160
ATGTATCCCCATCTCAAGGACTGCTAG                                  507
 M  Y  P  H  L  K  D  C  *                                   168
```

FIG. 2B

| | |
|---|---|
| SEQ ID NO:4 (150 amino acids) | dsesdctgse pvdafqafse gkeayvlvrs tdpkardclk gepagekqdn tlpvmmtfkn gtdwastdwt ftldgakvta tlgnltqnre vvydsqshhc hvdkvekevp dyemwmldag glevevecr qkleelasgr nqmyphlkdc |
| SEQ ID NO:6 (149 amino acids) | sesdctgse pvdafqafse gkeayvlvrs tdpkardclk gepagekqdn tlpvmmtfkn gtdwastdwt ftldgakvta tlgnltqnre vvydsqshhc hvdkvekevp dyemwmldag glevevecr qkleelasgr nqmyphlkdc |
| SEQ ID NO:8 (148 amino acids) | esdctgse pvdafqafse gkeayvlvrs tdpkardclk gepagekqdn tlpvmmtfkn gtdwastdwt ftldgakvta tlgnltqnre vvydsqshhc hvdkvekevp dyemwmldag glevevecr qkleelasgr nqmyphlkdc |
| SEQ ID NO:10 (147 amino acids) | sdctgse pvdafqafse gkeayvlvrs tdpkardclk gepagekqdn tlpvmmtfkn gtdwastdwt ftldgakvta tlgnltqnre vvydsqshhc hvdkvekevp dyemwmldag glevevecr qkleelasgr nqmyphlkdc |
| SEQ ID NO:12 (146 amino acids) | dctgse pvdafqafse gkeayvlvrs tdpkardclk gepagekqdn tlpvmmtfkn gtdwastdwt ftldgakvta tlgnltqnre vvydsqshhc hvdkvekevp dyemwmldag glevevecr qkleelasgr nqmyphlkdc |
| SEQ ID NO:14 (145 amino acids) | ctgse pvdafqafse gkeayvlvrs tdpkardclk gepagekqdn tlpvmmtfkn gtdwastdwt ftldgakvta tlgnltqnre vvydsqshhc hvdkvekevp dyemwmldag glevevecr qkleelasgr nqmyphlkdc |

FIG. 10

MUTANT #1   SEQ ID NO:22 (150 amino acids)

dsesdctgse pvdafqafse gkeayvlvrs tdpkardclk gepagekqdn
tlpvmmtfkn gtdwastdwt ftldgakvta tlgnltqnre vvydsqshhc
hvdkvekevp dyeqwqsngs addkeveccr qkleelasgr nqmyphlkdc MUTANT #2   SEQ ID NO:23 (150 amino acids)

dsesdctgse pvdafqafse gkeayvlvrs tdpkardclk gepngekqdn
tlpvmmtfkn gtdwastdwt ftldgakvta tlgnltqnre vvydsqshhc
hvdkvekevp dyemwqsdag adaveveccr qkleelasgr nqmyphlkgc MUTANT #3   SEQ ID NO:24 (150 amino acids)

dsesdctgse pvdafqafse gkeayvlvrs tdpkardclk gepngekqdn
tlpvmmtfkn gtdwastdwt ftldgakvta tlgnltqnre vvydsqshhc
hvdkvekevp dyemwqldag gdeveveccr qkleelasgr nqmyphlkgc MUTANT #4   SEQ ID NO:25 (150 amino acids)

dsesdctgse pvdafqafse gkeayvlvrs tdpkardclk gepngekqdn
tlpvmmtfkn gtdwastdwt ftldgakvta tlgnltqnre vvydsqshhc
hvdkvekevp dyemwmldag gleveveccr qkleelasgr nqmyphlkdc

SEQ ID NO: 26 (11 amino acids) from amino acid positions 114 to 124 of SEQ ID NO: 4 and 132-142 of SEQ ID NO: 2 mwmldagglev

SEQ ID NO: 27 (11 amino acids)   from amino acid positions 114 to 124 of SEQ ID NO: 4 in Coversin variant 1 (SEQ ID NO: 22).

qwqsngsaddk

SEQ ID NO: 28 (11 amino acids)   from amino acid positions 114 to 124 of SEQ ID NO: 4 in Coversin variant 2 (SEQ ID NO: 23).

mwqsdagadav

SEQ ID NO: 29 (11 amino acids)   from amino acid positions 114 to 124 of SEQ ID NO: 4 in Coversin variant 3 (SEQ ID NO: 24).

mwqldaggdev

SEQUENCE LISTING

<160> NUMBER OF SEQ ID NOS: 29

<210> SEQ ID NO 1
<211> LENGTH: 507
<212> TYPE: DNA
<213> ORGANISM: Ornithodoros moubata

<400> SEQUENCE: 1

```
atgctggttt tggtgaccct gattttctcc ttttctgcga acatcgcata tgctgacagc      60
gaaagcgact gcactggaag cgaacctgtt gacgccttcc aagctttcag tgagggcaaa     120
gaggcatatg tcctggtgag gtccacggat cccaaagcga gggactgctt gaaaggagaa     180
ccagccggag aaaagcagga caacacgttg ccggtgatga tgacgtttaa gaatggcaca     240
gactgggctt caaccgattg gacgtttact ttggacggcg caaaggtaac ggcaaccctt     300
ggtaacctaa cccaaaatag ggaagtggtc tacgactcgc aaagtcatca ctgccacgtt     360
gacaaggtcg agaaggaagt tccagattat gagatgtgga tgctcgatgc gggagggctt     420
gaagtggaag tcgagtgctg ccgtcaaaag cttgaagagt tggcgtctgg caggaaccaa     480
atgtatcccc atctcaagga ctgctag                                         507
```

<210> SEQ ID NO 2
<211> LENGTH: 168
<212> TYPE: PRT
<213> ORGANISM: Ornithodoros moubata

<400> SEQUENCE: 2

Met Leu Val Leu Val Thr Leu Ile Phe Ser Phe Ser Ala Asn Ile Ala
1               5                   10                  15

Tyr Ala Asp Ser Glu Ser Asp Cys Thr Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Gly Leu Glu Val Glu Val
    130                 135                 140

Glu Cys Cys Arg Gln Lys Leu Glu Glu Leu Ala Ser Gly Arg Asn Gln
145                 150                 155                 160

Met Tyr Pro His Leu Lys Asp Cys
                165

<210> SEQ ID NO 3
<211> LENGTH: 453
<212> TYPE: DNA
<213> ORGANISM: Ornithodoros moubata

<400> SEQUENCE: 3
gacagcgaaa gcgactgcac tggaagcgaa cctgttgacg ccttccaagc tttcagtgag      60
ggcaaagagg catatgtcct ggtgaggtcc acggatccca agcgaggga ctgcttgaaa      120
ggagaaccag ccggagaaaa gcaggacaac acgttgccgg tgatgatgac gtttaagaat      180
ggcacagact gggcttcaac cgattggacg tttactttgg acggcgcaaa ggtaacggca     240
acccttggta acctaaccca aaatagggaa gtggtctacg actcgcaaag tcatcactgc     300
cacgttgaca aggtcgagaa ggaagttcca gattatgaga tgtggatgct cgatgcggga     360
gggcttgaag tggaagtcga gtgctgccgt caaaagcttg aagagttggc gtctggcagg     420
aaccaaatgt atccccatct caaggactgc tag                                  453

<210> SEQ ID NO 4
<211> LENGTH: 150
<212> TYPE: PRT
<213> ORGANISM: Ornithodoros moubata

<400> SEQUENCE: 4

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Ala Gly Glu Lys Gln
        35                  40                  45

Asp Asn Thr Leu Pro Val Met Met Thr Phe Lys Asn Gly Thr Asp Trp
    50                  55                  60

```
Ala Ser Thr Asp Trp Thr Phe Thr Leu Asp Gly Ala Lys Val Thr Ala
 65                  70                  75                  80

Thr Leu Gly Asn Leu Thr Gln Asn Arg Glu Val Val Tyr Asp Ser Gln
                 85                  90                  95

Ser His His Cys His Val Asp Lys Val Glu Lys Glu Val Pro Asp Tyr
                100                 105                 110

Glu Met Trp Met Leu Asp Ala Gly Gly Leu Glu Val Glu Val Glu Cys
            115                 120                 125

Cys Arg Gln Lys Leu Glu Glu Leu Ala Ser Gly Arg Asn Gln Met Tyr
        130                 135                 140

Pro His Leu Lys Asp Cys
145                 150

<210> SEQ ID NO 5
<211> LENGTH: 450
<212> TYPE: DNA
<213> ORGANISM: Ornithodoros moubata

<400> SEQUENCE: 5
agcgaaagcg actgcactgg aagcgaacct gttgacgcct tccaagcttt cagtgagggc      60
aaagaggcat atgtcctggt gaggtccacg gatcccaaag cgagggactg cttgaaagga     120
gaaccagccg gagaaaagca ggacaacacg ttgccggtga tgatgacgtt taagaatggc     180
acagactggg cttcaaccga ttggacgttt actttggacg gcgcaaaggt aacggcaacc     240
cttggtaacc taacccaaaa tagggaagtg gtctacgact cgcaaagtca tcactgccac     300
gttgacaagg tcgagaagga agttccagat tatgagatgt ggatgctcga tgcgggaggg     360
cttgaagtgg aagtcgagtg ctgccgtcaa aagcttgaag agttggcgtc tggcaggaac     420
caaatgtatc cccatctcaa ggactgctag                                      450

<210> SEQ ID NO 6
<211> LENGTH: 149
<212> TYPE: PRT
<213> ORGANISM: Ornithodoros moubata

<400> SEQUENCE: 6

Ser Glu Ser Asp Cys Thr Gly Ser Glu Pro Val Asp Ala Phe Gln Ala
 1               5                  10                  15

Phe Ser Glu Gly Lys Glu Ala Tyr Val Leu Val Arg Ser Thr Asp Pro
             20                  25                  30

Lys Ala Arg Asp Cys Leu Lys Gly Pro Ala Gly Glu Lys Gln Asp
         35                  40                  45

Asn Thr Leu Pro Val Met Met Thr Phe Lys Asn Gly Thr Asp Trp Ala
 50                  55                  60

Ser Thr Asp Trp Thr Phe Thr Leu Asp Gly Ala Lys Val Thr Ala Thr
 65                  70                  75                  80

Leu Gly Asn Leu Thr Gln Asn Arg Glu Val Val Tyr Asp Ser Gln Ser
                 85                  90                  95

His His Cys His Val Asp Lys Val Glu Lys Glu Val Pro Asp Tyr Glu
                100                 105                 110

Met Trp Met Leu Asp Ala Gly Gly Leu Glu Val Glu Val Glu Cys Cys
            115                 120                 125

Arg Gln Lys Leu Glu Glu Leu Ala Ser Gly Arg Asn Gln Met Tyr Pro
        130                 135                 140

His Leu Lys Asp Cys
145
```

-continued

```
<210> SEQ ID NO 7
<211> LENGTH: 447
<212> TYPE: DNA
<213> ORGANISM: Ornithodoros moubata

<400> SEQUENCE: 7
gaaagcgact gcactggaag cgaacctgtt gacgccttcc aagctttcag tgagggcaaa      60
gaggcatatg tcctggtgag gtccacggat cccaaagcga gggactgctt gaaaggagaa     120
ccagccggag aaaagcagga caacacgttg ccggtgatga tgacgtttaa gaatggcaca     180
gactgggctt caaccgattg gacgtttact ttggacggcg caaggtaaac ggcaacccct     240
ggtaacctaa cccaaaatag ggaagtggtc tacgactcgc aaagtcatca ctgccacgtt     300
gacaaggtcg agaaggaagt tccagattat gagatgtgga tgctcgatgc gggagggctt     360
gaagtggaag tcgagtgctg ccgtcaaaag cttgaagagt tggcgtctgg caggaaccaa     420
atgtatcccc atctcaagga ctgctag                                        447

<210> SEQ ID NO 8
<211> LENGTH: 148
<212> TYPE: PRT
<213> ORGANISM: Ornithodoros moubata

<400> SEQUENCE: 8

Glu Ser Asp Cys Thr Gly Ser Glu Pro Val Asp Ala Phe Gln Ala Phe
1               5                   10                  15

Ser Glu Gly Lys Glu Ala Tyr Val Leu Val Arg Ser Thr Asp Pro Lys
                20                  25                  30

Ala Arg Asp Cys Leu Lys Gly Glu Pro Ala Gly Glu Lys Gln Asp Asn
            35                  40                  45

Thr Leu Pro Val Met Met Thr Phe Lys Asn Gly Thr Asp Trp Ala Ser
        50                  55                  60

Thr Asp Trp Thr Phe Thr Leu Asp Gly Ala Lys Val Thr Ala Thr Leu
65                  70                  75                  80

Gly Asn Leu Thr Gln Asn Arg Glu Val Val Tyr Asp Ser Gln Ser His
                85                  90                  95

His Cys His Val Asp Lys Val Glu Lys Glu Val Pro Asp Tyr Glu Met
            100                 105                 110

Trp Met Leu Asp Ala Gly Gly Leu Glu Val Glu Val Glu Cys Cys Arg
        115                 120                 125

Gln Lys Leu Glu Glu Leu Ala Ser Gly Arg Asn Gln Met Tyr Pro His
    130                 135                 140

Leu Lys Asp Cys
145

<210> SEQ ID NO 9
<211> LENGTH: 444
<212> TYPE: DNA
<213> ORGANISM: Ornithodoros moubata

<400> SEQUENCE: 9
agcgactgca ctggaagcga acctgttgac gccttccaag ctttcagtga gggcaaagag      60
gcatatgtcc tggtgaggtc cacggatccc aaagcgaggg actgcttgaa aggagaacca     120
gccggagaaa agcaggacaa cacgttgccg gtgatgatga cgtttaagaa tggcacagac     180
tgggcttcaa ccgattggac gtttactttg gacggcgcaa ggtaacggca acccttggt     240 aacctaaccc aaaatagggga agtggtctac gactcgcaaa gtcatcactg ccacgttgac     300
```

```
aaggtcgaga aggaagttcc agattatgag atgtggatgc tcgatgcggg agggcttgaa    360
gtggaagtcg agtgctgccg tcaaaagctt gaagagttgg cgtctggcag gaaccaaatg    420
tatccccatc tcaaggactg ctag                                           444

<210> SEQ ID NO 10
<211> LENGTH: 147
<212> TYPE: PRT
<213> ORGANISM: Ornithodoros moubata

<400> SEQUENCE: 10

Ser Asp Cys Thr Gly Ser Glu Pro Val Asp Ala Phe Gln Ala Phe Ser
1               5                   10                  15

Glu Gly Lys Glu Ala Tyr Val Leu Val Arg Ser Thr Asp Pro Lys Ala
            20                  25                  30

Arg Asp Cys Leu Lys Gly Glu Pro Ala Gly Glu Lys Gln Asp Asn Thr
        35                  40                  45

Leu Pro Val Met Met Thr Phe Lys Asn Gly Thr Asp Trp Ala Ser Thr
    50                  55                  60

Asp Trp Thr Phe Thr Leu Asp Gly Ala Lys Val Thr Ala Thr Leu Gly
65                  70                  75                  80

Asn Leu Thr Gln Asn Arg Glu Val Val Tyr Asp Ser Gln Ser His His
                85                  90                  95

Cys His Val Asp Lys Val Glu Lys Glu Val Pro Asp Tyr Glu Met Trp
            100                 105                 110

Met Leu Asp Ala Gly Gly Leu Glu Val Glu Val Glu Cys Cys Arg Gln
        115                 120                 125

Lys Leu Glu Glu Leu Ala Ser Gly Arg Asn Gln Met Tyr Pro His Leu
    130                 135                 140

Lys Asp Cys
145

<210> SEQ ID NO 11
<211> LENGTH: 441
<212> TYPE: DNA
<213> ORGANISM: Ornithodoros moubata

<400> SEQUENCE: 11
gactgcactg gaagcgaacc tgttgacgcc ttccaagctt tcagtgaggg caaagaggca     60
tatgtcctgg tgaggtccac ggatcccaaa gcgaggact gcttgaaagg agaaccagcc    120
ggagaaaagc aggacaacac gttgccggtg atgatgacgt ttaagaatgg cacagactgg   180
gcttcaaccg attggacgtt tactttggac ggcgcaaagg taacggcaac ccttggtaac   240
ctaacccaaa atagggaagt ggtctacgac tcgcaaagtc atcactgcca cgttgacaag   300
gtcgagaagg aagttccaga ttatgagatg tggatgctcg atgcgggagg gcttgaagtg   360
gaagtcgagt gctgccgtca aaagcttgaa gagttggcgt ctggcaggaa ccaaatgtat   420
ccccatctca aggactgcta g                                              441

<210> SEQ ID NO 12
<211> LENGTH: 146
<212> TYPE: PRT
<213> ORGANISM: Ornithodoros moubata
```

```
<400> SEQUENCE: 12

Asp Cys Thr Gly Ser Glu Pro Val Asp Ala Phe Gln Ala Phe Ser Glu
1               5                   10                  15

Gly Lys Glu Ala Tyr Val Leu Val Arg Ser Thr Asp Pro Lys Ala Arg
            20                  25                  30

Asp Cys Leu Lys Gly Glu Pro Ala Gly Glu Lys Gln Asp Asn Thr Leu
        35                  40                  45

Pro Val Met Met Thr Phe Lys Asn Gly Thr Asp Trp Ala Ser Thr Asp
    50                  55                  60

Trp Thr Phe Thr Leu Asp Gly Ala Lys Val Thr Ala Thr Leu Gly Asn
65                  70                  75                  80

Leu Thr Gln Asn Arg Glu Val Val Tyr Asp Ser Gln Ser His His Cys
                85                  90                  95

His Val Asp Lys Val Glu Lys Glu Val Pro Asp Tyr Glu Met Trp Met
            100                 105                 110

Leu Asp Ala Gly Gly Leu Glu Val Glu Val Glu Cys Cys Arg Gln Lys
        115                 120                 125

Leu Glu Glu Leu Ala Ser Gly Arg Asn Gln Met Tyr Pro His Leu Lys
    130                 135                 140

Asp Cys
145

<210> SEQ ID NO 13
<211> LENGTH: 438
<212> TYPE: DNA
<213> ORGANISM: Ornithodoros moubata

<400> SEQUENCE: 13
tgcactggaa gcgaacctgt tgacgccttc caagctttca gtgagggcaa agaggcatat      60
gtcctggtga ggtccacgga tcccaaagcg agggactgct tgaaaggaga ccagccgga     120 gaaaagcagg acaacacgtt gccggtgatg atgacgttta agaatggcac agactgggct     180
tcaaccgatt ggacgtttac tttggacggc gcaaaggtaa cggcaaccct tggtaaccta     240
acccaaaata gggaagtggt ctacgactcg aaagtcatc actgccacgt tgacaaggtc      300
gagaaggaag ttccagatta tgagatgtgg atgctcgatg cgggagggct tgaagtggaa     360
gtcgagtgct gccgtcaaaa gcttgaagag ttggcgtctg caggaaccaa atgtatccc     420 catctcaagg actgctag                                                   438

<210> SEQ ID NO 14
<211> LENGTH: 145
<212> TYPE: PRT
<213> ORGANISM: Ornithodoros moubata

<400> SEQUENCE: 14

Cys Thr Gly Ser Glu Pro Val Asp Ala Phe Gln Ala Phe Ser Glu Gly
1               5                   10                  15

Lys Glu Ala Tyr Val Leu Val Arg Ser Thr Asp Pro Lys Ala Arg Asp
            20                  25                  30

Cys Leu Lys Gly Glu Pro Ala Gly Glu Lys Gln Asp Asn Thr Leu Pro
        35                  40                  45

Val Met Met Thr Phe Lys Asn Gly Thr Asp Trp Ala Ser Thr Asp Trp
    50                  55                  60

Thr Phe Thr Leu Asp Gly Ala Lys Val Thr Ala Thr Leu Gly Asn Leu
65                  70                  75                  80
```

```
Thr Gln Asn Arg Glu Val Val Tyr Asp Ser Gln Ser His His Cys His
                85                  90                  95

Val Asp Lys Val Glu Lys Glu Val Pro Asp Tyr Glu Met Trp Met Leu
            100                 105                 110

Asp Ala Gly Gly Leu Glu Val Glu Val Glu Cys Cys Arg Gln Lys Leu
        115                 120                 125

Glu Glu Leu Ala Ser Gly Arg Asn Gln Met Tyr Pro His Leu Lys Asp
    130                 135                 140

Cys
145

<210> SEQ ID NO 15
<211> LENGTH: 20
<212> TYPE: PRT
<213> ORGANISM: Artificial Sequence
<220> FEATURE:
<223> OTHER INFORMATION: PAS sequence

<400> SEQUENCE: 15

Ala Ser Pro Ala Ala Pro Ala Pro Ala Ser Pro Ala Ala Pro Ala Pro
1               5                   10                  15

Ser Ala Pro Ala
            20

<210> SEQ ID NO 16
<211> LENGTH: 20
<212> TYPE: PRT
<213> ORGANISM: Artificial Sequence
<220> FEATURE:
<223> OTHER INFORMATION: PAS sequence

<400> SEQUENCE: 16

Ala Ala Pro Ala Ser Pro Ala Pro Ala Ala Pro Ser Ala Pro Ala Pro
1               5                   10                  15

Ala Ala Pro Ser
            20

<210> SEQ ID NO 17
<211> LENGTH: 20
<212> TYPE: PRT
<213> ORGANISM: Artificial Sequence
<220> FEATURE:
<223> OTHER INFORMATION: PAS sequence

<400> SEQUENCE: 17

Ala Pro Ser Ser Pro Ser Pro Ser Ala Pro Ser Ser Pro Ser Pro Ala
1               5                   10                  15

Ser Pro Ser Ser
            20

<210> SEQ ID NO 18
<211> LENGTH: 20
<212> TYPE: PRT
<213> ORGANISM: Artificial Sequence
<220> FEATURE:
<223> OTHER INFORMATION: PAS sequence

<400> SEQUENCE: 18

Ser Ala Pro Ser Ser Pro Ser Pro Ser Ala Pro Ser Ser Pro Ser Pro
1               5                   10                  15

Ala Ser Pro Ser
            20
```

```
<210> SEQ ID NO 19
<211> LENGTH: 20
<212> TYPE: PRT
<213> ORGANISM: Artificial Sequence
<220> FEATURE:
<223> OTHER INFORMATION: PAS sequence

<400> SEQUENCE: 19

Ser Ser Pro Ser Ala Pro Ser Pro Ser Ser Pro Ala Ser Pro Ser Pro
1               5                   10                  15

Ser Ser Pro Ala
            20

<210> SEQ ID NO 20
<211> LENGTH: 24
<212> TYPE: PRT
<213> ORGANISM: Artificial Sequence
<220> FEATURE:
<223> OTHER INFORMATION: PAS sequence

<400> SEQUENCE: 20

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 21
<211> LENGTH: 20
<212> TYPE: PRT
<213> ORGANISM: Artificial Sequence
<220> FEATURE:
<223> OTHER INFORMATION: PAS sequence

<400> SEQUENCE: 21

Ala Ser Ala Ala Ala Pro Ala Ala Ala Ser Ala Ala Ala Ser Ala Pro
1               5                   10                  15

Ser Ala Ala Ala
            20

<210> SEQ ID NO 22
<211> LENGTH: 150
<212> TYPE: PRT
<213> ORGANISM: Artificial Sequence
<220> FEATURE:
<223> OTHER INFORMATION: Coversin variant 1

<400> SEQUENCE: 22

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
                20                  25                  30

Pro Lys Ala Arg Asp Cys Leu Lys Gly Glu Pro Ala Gly Glu Lys Gln
            35                  40                  45

Asp Asn Thr Leu Pro Val Met Met Thr Phe Lys Asn Gly Thr Asp Trp
        50                  55                  60

Ala Ser Thr Asp Trp Thr Phe Thr Leu Asp Gly Ala Lys Val Thr Ala
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110
```

```
Glu Gln Trp Gln Ser Asn Gly Ser Ala Asp Asp Lys Glu Val Glu Cys
            115                 120                 125

Cys Arg Gln Lys Leu Glu Leu Ala Ser Gly Arg Asn Gln Met Tyr
    130                 135                 140

Pro His Leu Lys Asp Cys
145             150

<210> SEQ ID NO 23
<211> LENGTH: 150
<212> TYPE: PRT
<213> ORGANISM: Artificial Sequence
<220> FEATURE:
<223> OTHER INFORMATION: Coversin variant 2

<400> SEQUENCE: 23

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
                20                  25                  30

Pro Lys Ala Arg Asp Cys Leu Lys Gly Glu Pro Asn Gly Glu Lys Gln
            35                  40                  45

Asp Asn Thr Leu Pro Val Met Met Thr Phe Lys Asn Gly Thr Asp Trp
        50                  55                  60

Ala Ser Thr Asp Trp Thr Phe Thr Leu Asp Gly Ala Lys Val Thr Ala
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110

Glu Met Trp Gln Ser Asp Ala Gly Ala Asp Ala Val Glu Val Glu Cys
            115                 120                 125

Cys Arg Gln Lys Leu Glu Glu Leu Ala Ser Gly Arg Asn Gln Met Tyr
    130                 135                 140

Pro His Leu Lys Gly Cys
145             150

<210> SEQ ID NO 24
<211> LENGTH: 150
<212> TYPE: PRT
<213> ORGANISM: Artificial Sequence
<220> FEATURE:
<223> OTHER INFORMATION: Coversin variant 3

<400> SEQUENCE: 24

Asp Ser Glu Ser Asp Cys Thr Gly Ser Glu Pro Val Asp Ala Phe Gln
1               5                   10                  15

```
Glu Met Trp Gln Leu Asp Ala Gly Gly Asp Glu Val Glu Val Glu Cys
            115                 120                 125

Cys Arg Gln Lys Leu Glu Glu Leu Ala Ser Gly Arg Asn Gln Met Tyr
    130                 135                 140

Pro His Leu Lys Gly Cys
145                 150

<210> SEQ ID NO 25
<211> LENGTH: 150
<212> TYPE: PRT
<213> ORGANISM: Artificial Sequence
<220> FEATURE:
<223> OTHER INFORMATION: Coversin variant 4

<400> SEQUENCE: 25

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Asn Gly Glu Lys Gln
        35                  40                  45

Asp Asn Thr Leu Pro Val Met Met Thr Phe Lys Asn Gly Thr Asp Trp
    50                  55                  60

Ala Ser Thr Asp Trp Thr Phe Thr Leu Asp Gly Ala Lys Val Thr Ala
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110

Glu Met Trp Met Leu Asp Ala Gly Gly Leu Glu Val Glu Val Glu Cys
            115                 120                 125

Cys Arg Gln Lys Leu Glu Glu Leu Ala Ser Gly Arg Asn Gln Met Tyr
    130                 135                 140

Pro His Leu Lys Asp Cys
145                 150

<210> SEQ ID NO 26
<211> LENGTH: 11
<212> TYPE: PRT
<213> ORGANISM: Artificial Sequence
<220> FEATURE:
<223> OTHER INFORMATION: Loop sequence

<400> SEQUENCE: 26

Met Trp Met Leu Asp Ala Gly Gly Leu Glu Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Loop sequence of Coversin variant 1

<400> SEQUENCE: 27

Gln Trp Gln Ser Asn Gly Ser Ala Asp Asp Lys
1               5                   10
```

```
<210> SEQ ID NO 28
<211> LENGTH: 11
<212> TYPE: PRT
<213> ORGANISM: Artificial Sequence
<220> FEATURE:
<223> OTHER INFORMATION: Loop sequence of Coversin variant 2

<400> SEQUENCE: 28

Met Trp Gln Ser Asp Ala Gly Ala Asp Ala Val
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Loop sequence of Coversin variant 3

<400> SEQUENCE: 29

Met Trp Gln Leu Asp Ala Gly Gly Asp Glu Val
1               5                   10
```

COVERSIN (OMCI) FOR THE TREATMENT OF AUTOIMMUNE BLISTERING DISEASES: BULLOUS PEMPHIGOID (BP) AND EPIDERMOLYSIS BULLOSA ACQUISITA (EBA)

CROSS REFERENCE TO RELATED APPLICATIONS

This application is a national phase entry pursuant to 35 U.S.C. § 371 of International Application No. PCT/EP2018/060241, filed Apr. 20, 2018, which claims the benefit of priority of Great Britain Application No. 1706404.9, filed Apr. 21, 2017, Great Britain Application No. 1706406.4, filed Apr. 21, 2017, and Great Britain Application No. 1706452.8, filed Apr. 24, 2017, each of which is incorporated by reference herein in its entirety for any purpose.

SEQUENCE LISTING

The instant application contains a Sequence Listing which has been submitted in ASCII format via EFS-Web and is hereby incorporated by reference in its entirety. Said ASCII copy, created on Nov. 1, 2019, is named 2019-11-01_01169-0017-00US_Seq_List_ST25.txt and is 22.8 KB in size.

FIELD OF THE INVENTION

The present invention relates to methods of treating and preventing autoimmune blistering diseases.

All documents mentioned in the text and listed at the end of this description are incorporated herein by reference.

BACKGROUND TO THE INVENTION

Complement

The complement system is an essential part of the body's natural defense mechanism against foreign invasion and is also involved in the inflammatory process. More than 30 proteins in serum and at the cell surface are involved in the functioning and regulation of the complement system. Recently, it has become apparent that, as well as the approximately 35 known components of the complement system, which may be associated with both beneficial and pathological processes, the complement system itself interacts with at least 85 biological pathways with functions as diverse as angiogenesis, platelet activation, glucose metabolism and spermatogenesis.

The complement system is activated by the presence of foreign antigens. Three activation pathways exist: (1) the classical pathway which is activated by IgM and IgG complexes or by recognition of carbohydrates; (2) the alternative pathway which is activated by non-self surfaces (lacking specific regulatory molecules) and by bacterial endotoxins; and (3) the lectin pathway which is activated by binding of mannan-binding lectin (MBL) to mannose residues on the surface of a pathogen. The three pathways comprise parallel cascades of events that result in the production of complement activation through the formation of similar C3[1] and C5 convertases on cell surfaces, resulting in the release of acute mediators of inflammation (C3a and C5a) and the formation of the membrane attack complex (MAC). The parallel cascades involved in the classical and alternative pathways are shown in FIG. 1.

[1] It is conventional to refer to the components of the complement pathway by the letter "C" followed by a number, such as "3", such that "C3" refers to the third component of the complement system. Some of these components are cleaved during activation of the complement system and the cleavage products are given lower case letters after the number. Thus, C5 is cleaved into fragments which are conventionally labelled C5a and C5b. The complement proteins do not necessarily act in their number order and so the number does not necessarily give any indication of the order of action. This naming convention is used in this application.

The classical complement pathway, the alternative complement pathway and the lectin complement pathway are herein collectively referred to as the complement pathways. C5b initiates the 'late' events of complement activation. These comprise a sequence of polymerization reactions in which the terminal complement components interact to form the MAC, which creates a pore in the cell membranes of some pathogens which can lead to their death. The terminal complement components include C5b (which initiates assembly of the membrane attack system), C6, C7, C8 and C9.

LTB4

Leukotriene B4 (LTB4) is the most powerful chemotactic and chemokinetic eicosanoid described and promotes adhesion of neutrophils to the vascular endothelium via upregulation of integrins [1]. It is also a complete secretagogue for neutrophils, induces their aggregation and increases microvascular permeability. LTB4 recruits and activates natural killer cells, monocytes and eosinophils. It increases superoxide radical formation [2] and modulates gene expression including production of a number of proinflammatory cytokines and mediators which may augment and prolong tissue inflammation [3,4]. LTB4 also has roles in the induction and management of adaptive immune responses. For example regulation of dendritic cell trafficking to draining lymph nodes [5,6], Th2 cytokine IL-13 production from lung T cells [7], recruitment of antigen-specific effector CD8+ T cells [8] and activation and proliferation of human B lymphocytes [9].

Leukotriene B4 (LTB4) and the hydroxyeicosanoids mediate their effects though the BLT1 and BLT2 G-protein coupled receptors [10,11]. Human BLT1 is a high affinity receptor (Kd 0.39-1.5 nM; [12]) specific for LTB4 with only 20-hydroxy LTB4 and 12-epi LTB4 able to displace LTB4 in competitive binding studies [13]. Human BLT2 has a 20-fold lower affinity (Kd 23 nM) for LTB4 than BLT1 and is activated by binding a broader range of eicosanoids including 12-epi LTB4, 20-hydroxy LTB4, 12(S)- and 15(S)-HETE and 12(S)- and 15(S)-HPETE [13]. Human BLT2 has 45.2 and 44.6% amino acid identity with human and mouse BLT1, while human and mouse BLT2 have 92.7% identity [11].

Human BLT1 is mainly expressed on the surface of leukocytes, though it has recently been described in endothelial cells and vascular smooth muscle cells. Human BLT2 is expressed in a broader range of tissue and cell types. A number of specific antagonists of BLT1 and BLT2 have been described which inhibit activation, extravasation and apoptosis of human neutrophils [14] and reduce symptoms caused by neutrophil infiltration in mouse models of inflammatory arthritis [15] and renal ischaemia reperfusion [16]. Increasing numbers of studies indicate that both BLT1 and BLT2 can mediate pathological effects through LTB4 and hydroxyeicosanoids [17], although BLT1 certainly has a dominant role in some pathologies such as collagen induced arthritis in mice [18]. BLT1−/− deficient mice have also highlighted the importance of BLT1 in directing neutrophil migration in inflammatory responses. In particular, a 5LO deficient mouse strain was used to show autocrine activation of BLT1 on neutrophils is needed for their recruitment into arthritic joints [19].

A number of marketed drugs target the eicosanoids. These include the glucocorticoids which modulate phopholipase A2 (PLA2) and thereby inhibit release of the eicosanoid precursor arachidonic acid (AA) [20]. Non-steroidal antiinflammatory drugs (NSAID) and other COX2 inhibitors which prevent synthesis of the prostaglandins and thromboxanes [21]. There are also a number of LK modifiers which either inhibit the 5-LO enzyme required for LTB4 synthesis (Zileuton; [22]), or antagonise the CysLT1 receptor that mediates the effects of cysteinyl leukotrienes (Zafirlukast and Montelukast) [23]. The LK modifiers are orally available and have been approved by the FDA for use in the treatment of e.g. asthma. No drug that acts specifically on LTB4 or its receptors has yet reached the market.

Autoimmune Blistering Diseases (AIBD)

The skin, the largest organ of the body, is made up of five distinct layers. The epidermis is the outermost, protective layer of skin, and this adheres to the dermis, which is between the epidermis (with which it makes up the cutis) and the subcutaneous tissues. The dermis primarily consists of dense irregular connective tissue and is tightly connected to the epidermis through a basement membrane. Specialized proteins and structures are required for the dermis and epidermis to adhere, and separation of these layers gives rise to blisters or bulla.

Under normal circumstances, blisters will develop in response to irritation or injury of the skin, but in autoimmune blistering diseases (AIBD) blisters arise as a result of autoantibodies that attack desmosomal or hemidesmosomal structural proteins. These proteins are essential to the proper function of the basement membrane zone. In AIBD, adhesion of the epidermis and dermis is damaged as a result of the attack arising from autoantibodies to specific structures or proteins, so that ultimately the epidermis and dermis separate and blisters form.

AIBD are thus a group of autoimmune disorders in which blistering lesions that primarily affect the skin arise as a result of autoantibodies directed to skin antigens. In some AIBD, blisters can also form on the mucous membranes (e.g. in the oesophagus, anus, mouth, nasal passageways, genitals and throat).

Risk factors for development of AIBD include old age, drug treatment, viral infection and exposure to UV radiation or Xrays.

The specific symptoms and severity of blistering diseases vary from person to person, and in some cases, blistering lesions can cover a significant portion of the skin. There is no cure for AIBD, but treatments do exist. Without such treatment the diseases can cause life-threatening complications.

There are several different categories of AIBD including pemphigus, pemphigoid, IgA-mediated dermatoses and epidermolysis bullosa acquista (EBA). Pemphigus, pemphigoid and IgA-mediated dermatoses can be further broken down into additional subtypes.

"Pemphigus" is a general term for a group of related AIBD caused by an antibody mediated autoimmune reaction to desmogleins. The two main types of pemphigus are pemphigus vulgaris and pemphigus foliaceus.

Pemphigus vulgaris is the most common form of pemphigus, characterized by autoantibodies to Dsg3 (with about 50% of patients also having autoantibodies to Dsg1) and by blisters that rupture easily and cause painful erosions. In most cases, pemphigus vulgaris first develops in the mouth, followed by blistering of the skin, although any area may potentially be affected.

Pemphigus foliaceus is characterized by multiple small, blisters that quickly break apart to form itchy, scaly, crusted lesions that affect the uppermost layer of the skin. The scalp and face are usually affected first. Eventually, the chest, upper back may become involved. The lesions are usually not painful. The mucous membranes are usually not affected. These patients have autoantibodies to Dsg1.

Additional disorders are sometimes classified as subtypes of pemphigus including paraneoplastic pemphigus (which is an AIBD that stems from a tumour, with autoantibodies to e.g. Dsg1 and Dsg3) and pemphigus IgA (with autoantibodies to desmocollin).

"Pemphigoid" is used to refer to the group of related diseases characterized by blistering skin eruptions. The main forms of pemphigoid are bullous pemphigoid, mucous membrane pemphigoid, and pemphigoid gestationis.

Bullous pemphigoid is a chronic skin disease characterized by pruritus and rigid subepidermal blisters. Autoantibodies against the antigen BP180 (also called dystonin) and its NC16A domain (located in collagen XVII) are observed. This target antigen is a hemisdesmosome antigen. Within weeks, blisters often spread to the groin, armpit, abdomen, and the skin of flexor muscles, and the lesions may become widespread covering a significant portion of the skin and blisters may form inside the mouth. In most cases, the mucous membranes are not affected and, when they are, they tend to heal quickly. The lesions of bullous pemphigoid are often associated with intense itching.

Mucous membrane pemphigoid (MMP) (also called cicatricial pemphigoid (CP)) is also associated with subepidermal blistering, primarily affecting the mucous membrane (mainly the mouth and eyes, but the nose, throat, genitalia, and anus may also be affected). The symptoms of MMP vary among affected individuals depending upon the specific site(s) involved and the progression of the disease. The autoantigens are again directed to BP180 but various other autoantigens have been identified.

Epidermolysis bullosa acquista is relatively rare. In this condition, dermoepidermal separation as is seen in BP is also seen. Autoantibodies against type VII collagen (which forms anchoring fibrils that connect the epidermis and the BMZ to the papillary dermis) are characteristic in this autoimmune disorder of the skin that typically affects middle-aged and elderly people.

Most forms occur in middle-aged individuals, usually people in their 50s and 60s. However, autoimmune blistering diseases can affect individuals of any age including children. The overall incidence and prevalence of these conditions varies depending upon the specific population studied. Bullous pemphigoid, for example, is the most common immunobullous disease in Western Europe with a reported incidence of 43 per million per year in the U.K. and 7-13 per million per year in other parts of Europe [24].

AIBD diagnosis is based on clinical evaluation, and a detailed patient history, as well as identification of the characteristic autoantibodies, e.g. in blood or on a skin biopsy. Immunofluorescent assays are the preferred method of diagnosis.

There is currently no cure for these disorders, but they can be controlled e.g. with corticosteroids such as prednisone. Treatments may not be well tolerated and may be associated with toxicity [24]. By way of example, systemic corticosteroid therapy (e.g. prednisone and prednisolone) can be effective but this is, however, not effective in all cases and long-term treatment with high-doses of corticosteroids can cause serious side effects. The steroids are general and non-specific anti-inflammatory agents. Other immunosuppressants are used in many such conditions as a "bridge", as subjects cannot be kept on long term high dose steroids.

Topical corticosteroids are also used, but their use in extensive disease may be limited by practical factors (ability of patient to apply the treatment) and they may be associated with systemic absorption and adverse events. Immuosuppressive drugs (e.g. dapsone methylprednisolone, mycophenolate, azathioprine or cyclophosphamide) and immunosuppressive biological therapies (e.g. rituximab, and intravenous immunoglobulin G (IVIG)) have also been used but may have adverse effects.

New therapies for treating and preventing AIBD are thus required.

Complement Inhibitors

WO 2004/106369 (Evolutec Limited [25]) relates to complement inhibitors. A particular subset of the disclosed complement inhibitors are directed at C5 and prevent C5 being cleaved into C5a and C5b by any of the complement activation pathways. A particular example of such an inhibitor of C5 cleavage is a protein produced by ticks of the species Ornithdoros moubata, which is a protein consisting of amino acids 19 to 168 of the amino acid sequence shown in FIG. 4 of WO 2004/106369. In WO 2004/106369, this protein is known by the names "EV576" and "OmCI protein" and has more recently been known as "Coversin" (see, for instance, Jore et. al., Nature Structural & Molecular Biology, Structural basis for therapeutic inhibition of complement C5, published online on 28 Mar. 2016—doi: 10.1038/nsmb.3196). This protein is referred to herein as "Coversin".

In the tick, Coversin is expressed as a pre-protein having a leader sequence comprising amino acids 1 to 18 of the amino acid sequence shown in FIG. 4 of WO 2004/106369 at the N-terminal end of the mature Coversin protein. The leader sequence is cleaved off after expression. The mature protein has the sequence consisting of amino acids 19 to 168 of the amino acid sequence shown in FIG. 4 of WO 2004/106369 and FIG. 2 of the present application.

Coversin also has the ability to inhibit leukotriene B4 (LTB4) activity. The ability to bind LTB4 may be demonstrated by standard in vitro assays known in the art, for example by means of a competitive ELISA between Coversin and an anti-LTB4 antibody competing for binding to labelled LTB4, by isothermal titration calorimetry or by fluorescence titration. There are a number of further patent applications, such as WO 2007/028968, WO 2008/029167, WO 2008/029169, WO 2011/083317 and WO 2016/198133, which relate to the use of Coversin or functional equivalents thereof in various applications. WO 2015/185760 discloses that Coversin and its structural equivalents are effective at preventing cleavage of polymorphs of C5 e.g. that reduce the therapeutic effectiveness of the marketed C5 complement inhibitor eculizumab. There is no disclosure in these applications of the use of Coversin or any functional equivalent thereof in the treatment of AIBD.

The potential role of the complement pathway has been discussed in the context of AIBD, but no current AIBD treatment targets complement, and the pathophysiology of these diseases is not fully understood. Furthermore, there is also evidence that blister formation can be induced directly, and without Complement activation [26], and on this basis new therapies that target the blocking of autoantibody binding, rather than prevention of complement activation are suggested in this field [26]. Furthermore, Exogenous C5a or IL-17A cannot overcome resistance to pemphigoid disease-like skin inflammation in Ltb4r1−/− mice [27].

Likewise, a role for LTB4 has been discussed in AIBD, and specifically in the context of neutrophil recruitment in the diseases, but again no current approved treatments for these conditions target this molecule.

In contrast, in work leading to the present invention, the molecule Coversin which binds LTB4 and which also inhibits the complement pathway by binding to C5, as discussed above, has been shown to reduce the affected body surface area (ABSA) with blisters in a mouse model of AIBD. Coversin has the ability to inhibit both Complement (by inhibiting C5) and also LTB4 and is therefore particularly advantageous in the prevention and treatment of AIBD, either alone or in combination with other AIBD treatments.

SUMMARY OF THE INVENTION

Coversin has been shown to reduce the percentage affected body surface area (ABSA) in a mouse model of EBA. In Example 1, the administration of Coversin before and during the induction of the disease was shown to lead to a reduction in the percentage ABSA (as assessed by determining skin areas exhibiting erythema, blisters, erosions, crusts, or alopecia and calculating the percentage of the total body surface affected by skin lesions (ABSA)) as compared to mice who were not treated with Coversin. By comparison with similar experiments in which other agents had been used (Zileuton and methylprednisolone), a greater effect could be observed with the administration of Coversin and this was particularly evident at the higher concentrations (e.g. 2.5 mg/kg and 0.25 mg/kg). Coversin thus appears to be more effective than a systemic immunosuppressant that is currently used in the treatment of AIBD (methylprednisolone), and more effective than an LTB4 inhibitor (Zileuton). It has also been shown (Example 2) that the administration of Coversin after induction of the disease can also lead to a reduction in the percentage ABSA. The dual inhibitory activity of Coversin, targeting both C5 and LTB4 thus appears to be particularly advantageous in the treatment of AIBD.

Prophylactic experiments were conducted using a modified Coversin polypeptide which has reduced or absent C5-binding activity but which retains LTB-4-binding ability. A reduction in the percentage of ABSA was also observed using this agent. Agents which have both C5-binding activity and LTB4-binding activity are preferred, but agents which have reduced or absent C5-binding activity but which retain LTB-4-binding ability or which have reduced or absent LTB4-binding activity but which retain C5-binding ability can be used in the present invention.

The present inventors have therefore demonstrated that administration of the tick protein Coversin (also referred to as EV576 and OmCI in the art and herein [25]) can be used to treat or prevent AIBD.

The invention therefore provides a method of treating or preventing an AIBD, which comprises administering a therapeutically or prophylactically effective amount of an agent which is a protein comprising amino acids 19 to 168 of the amino acid sequence in FIG. 2 (SEQ ID NO: 2) or a functional equivalent of this protein.

The invention also provides an agent which is a protein comprising amino acids 19 to 168 of the amino acid sequence in FIG. 2 (SEQ ID NO: 2) or a functional equivalent of this protein for use in a method of treating or preventing an AIBD.

The invention also provides a method of treating or preventing an AIBD, comprising administering a therapeutically or prophylactically effective amount of an agent which is a nucleic acid molecule encoding a protein comprising amino acids 19 to 168 of the amino acid sequence in FIG. 2 (SEQ ID NO: 2) or a functional equivalent of this protein.

The invention also provides an agent which is a nucleic acid molecule encoding a protein comprising amino acids 19 to 168 of the amino acid sequence in FIG. 2 (SEQ ID NO:

2) or a functional equivalent of this protein for use in a method of treating or preventing an AIBD.

The invention also provides a method of treating or preventing an AIBD, which comprises administering (a) a therapeutically or prophylactically effective amount of an agent which is a protein comprising amino acids 19 to 168 of the amino acid sequence in FIG. 2 (SEQ ID NO: 2) or a functional equivalent of this protein and (b) a second AIBD treatment.

The invention also provides (a) an agent which is a protein comprising amino acids 19 to 168 of the amino acid sequence in FIG. 2 (SEQ ID NO: 2) or a functional equivalent of this protein and (b) a second AIBD treatment, for use in a method of treating or preventing an AIBD.

The invention also provides a method of treating or preventing an AIBD, comprising administering (a) a therapeutically or prophylactically effective amount of an agent which is a nucleic acid molecule encoding a protein comprising amino acids 19 to 168 of the amino acid sequence in FIG. 2 (SEQ ID NO: 2) or a functional equivalent of this protein and (b) a second AIBD treatment.

The invention also provides (a) an agent which is a nucleic acid molecule encoding a protein comprising amino acids 19 to 168 of the amino acid sequence in FIG. 2 (SEQ ID NO: 2) or a functional equivalent of this protein and (b) a second AIBD treatment for use in a method of treating or preventing an AIBD.

The invention also provides a method of reducing the amount of a second AIBD treatment that is required to treat or prevent an AIBD, or reducing the duration of treatment with a second AIBD treatment that is required to treat or prevent an AIBD, said method comprising administering a therapeutically or prophylactically effective amount of an agent which is a protein comprising amino acids 19 to 168 of the amino acid sequence in FIG. 2 (SEQ ID NO: 2) or a functional equivalent of this protein, or a nucleic acid molecule encoding said agent, and said second AIBD treatment.

The invention also provides a method of reducing the autoantibody titre in a subject with an AIBD, said method comprising administering a therapeutically or prophylactically effective amount of an agent which is a protein comprising amino acids 19 to 168 of the amino acid sequence in FIG. 2 (SEQ ID NO: 2) or a functional equivalent of this protein, or a nucleic acid molecule encoding said agent, said method may optionally comprise administering a second AIBD treatment.

DETAILED DESCRIPTION

Diseases

The subject may have, be suspected of having or may be at risk of developing an AIBD.

The AIBD is preferably selected from pemphigus, pemphigoid, IgA-mediated dermatoses and epidermolysis bullosa acquista (EBA). Pemphigus may be pemphigus vulgaris or pemphigus foliaceus. "Pemphigoid" may be bullous pemphigoid, mucous membrane pemphigoid, and/or pemphigoid gestationis. Preferably the AIBD is EBA or bullous pemphigoid. The mouse model that is used in the Examples is a model for EBA but is also informative in respect of other AIBD, particularly bullous pemphigoid. The causative mechanism is similar for all AIBD i.e. immune complex formation and elaboration of immune response with in particular intense neutrophil and/or eosinophil involvement.

The presence of these diseases may be determined by routine diagnosis that is well understood in the art (see e.g. [28]).

Subjects at risk of developing an AIBD may benefit from administration of the agents referred to herein, in order to prevent AIBD. Risk factors for AIBD, and in particular Bullous Pemphigoid include genetic factors and other inducing factors [29]. There are reports of genetic predisposition, in terms of presence of major histocompatibility complex class II (MHC II) gene HLA-DQB1*0301 in patients with BP and mucous membrane pemphigoid. Polymorphism in the mitochondrially encoded ATP synthase 8 gene (MT-ATP8) may have an association with BP pathogenesis. Also included are CYP2D6 gene polymorphism and FCgamma R IIIa polymorphism Other inducing factors include:

1. Drugs: The majority of the BP-inducing medications contain or release sulfhydryl groups (penicillamine, captopril, penicillin and its derivatives, furosemide, and some cephalosporins). Also drugs containing a phenol ring (some cephalosporins and acetylsalicylic acid), angiotensin-converting enzyme inhibitors other than captopril, most non-steroidal antiinflammatory drugs, immunomodulators such as vaccines, dipeptidyl peptidase-IV inhibitors (gliptins), especially vildagliptin, and TNF-α blockers have been reported to induce BP 2. Viruses: post vaccination 3. UV or Xray irradiation About a third of BP patients have a neuro-psychiatric disease; stroke, dementia, Parkinsons etc.

Subjects having one or more of these risk factors are preferred, in terms of treatment or prevention of AIBD.

Outcomes of Administration

The subject may, as a result of the treatment, have reduced incidence of symptoms, alleviation of symptoms, inhibition or delay of occurrence or re-occurence of symptoms, or a combination thereof. Preferably the treatment gives rise to a reduction in the typical disease condition symptoms. For example, this may be manifest in reducing the size of blisters, reducing the number of blisters, reducing the percentage of the body surface that is affected, reducing the extent of oozing of the blisters, reduced pruritus, or reducing the incidence and/or severity of infection resulting from the blisters. A proportion of subjects will have complete resolution of symptoms and no further relapses. Clinical scoring may be conducted using the Bullous Pemphigoid Disease Activity Index (BPDAI) [30]. The global BPDAI is composed of 2 scores: total BPDAI activity and BPDAI damage. The total BPDAI activity score is the arithmetic sum of the 3 subcomponents—cutaneous blisters/erosions, cutaneous urticaria/erythema, and mucosal blisters/erosions.

The BPDAI damage score is the arithmetic sum of the items rated regionally for damage caused by more permanent features such as post-inflammatory hyperpigmentation, scarring and other. BPDAI quantifies lesion number and size thresholds. Lesions are rated based on the regions affected. BPDAI gives additional weighting to areas of the skin primarily affected in BP, such as the limbs, and less emphasis to scalp and face, to better differentiate clinical response in BP.

The global BPDAI scores can range from 0 to 372. For BPDAI activity up to 360 (maximum 240 for total skin activity-[120 for erosions/blisters, 120 for urticaria/erythema] and 120 for mucosal activity), and 0 to 12 for BPDAI damage, with higher scores indicating greater disease activity or damage. The global BPDAI score will be used to assess the inclusion of subjects.

BPDAI also has a separate subjective measure known as BPDAI-pruritus Index. The BPDAI pruritus component is based on a visual analogue scale, measuring the severity of itch during the past 24 h (0-10), the past week (0-10) and the past month (0-10) with a total score of 30.

Preferably the treatment gives rise to a reduction in the score of one or more signs measured by the Bullous Pemphigoid Disease Activity Index (BPDAI). Preferably the treatment gives rise to a reduction in the score of any one or more (for example 2 or 3) of cutaneous blisters/erosions, cutaneous urticaria/erythema and mucosal blisters/erosions.

In one embodiment the treatment gives rise to a reduction in the score for cutaneous blisters/erosions. In one embodiment the treatment gives rise to a reduction in the score for cutaneous urticaria/erythema. In one embodiment the treatment gives rise to a reduction in the score for mucosal blisters/erosions. In one embodiment the treatment gives rise to a reduction in the score for cutaneous blisters/erosions and cutaneous urticaria/erythema. In one embodiment the treatment gives rise to a reduction in the score for cutaneous urticaria/erythema and mucosal blisters/erosions. In one embodiment the treatment gives rise to a reduction in the score for cutaneous blisters/erosions and mucosal blisters/erosions. In one embodiment the treatment gives rise to a reduction in the score on the BPDAI-pruritus index.

In some embodiments the effects may be mediated by reduction or prevention of neutrophil and/or eosinophil involvement.

The treatment may also result in increasing the latency period before the onset of one or more stages of the disease, or between progression of disease stages. In some embodiments blistering may be prevented.

The treatment may also result in reduction of autoimmune antibody titre.

The treatment may also result in a reduction in the amount or duration of a second AIBD treatment that is required.

Thus in a further embodiment of the invention, there is provided a method of reducing the size and/or number of blisters in a subject with an AIBD, or reducing the percentage of the body surface that is affected in a subject with an AIBD, said method comprising administering a therapeutically or prophylactically effective amount of an agent which is a protein comprising amino acids 19 to 168 of the amino acid sequence in FIG. 2 (SEQ ID NO: 2) or a functional equivalent of this protein, or a nucleic acid molecule encoding said agent. This may be alone or with a second AIBD treatment.

The invention also provides an agent which is a protein comprising amino acids 19 to 168 of the amino acid sequence in FIG. 2 (SEQ ID NO: 2) or a functional equivalent of this protein, a nucleic acid molecule encoding said agent, for use in a method of reducing the size and/or number of blisters in a subject with an AIBD, or reducing the percentage of the body surface that is affected in a subject with an AIBD. This may be alone or with a second AIBD treatment.

The agent of the invention can be used in combination with other AIBD treatments, as discussed above. The combination of the agent of the invention with the other (referred to here as a "second" AIBD treatment may be such that the amount of the second AIBD is reduced in comparison to the amount that is used in the absence of treatment with the agent of the invention, or the duration of the treatment with second AIBD is reduced in comparison to the duration of treatment that is used in the absence of treatment with the agent of the invention. This is advantageous in view of the side effects of certain known treatments such as steroids, e.g. infections, diabetes mellitus, osteoporosis, thromboses, and gastrointestinal ulcers. Therefore, there is also provided a method of reducing the amount of a second AIBD treatment that is used for the treatment or reducing the duration of the treatment with a second AIBD, as detailed above.

Preferably the second AIBD treatment is selected from systemic corticosteroid therapy, topical corticosteroid therapy, immunosuppressive therapy and immunosuppressive biological therapy.

Preferably the corticosteroid is selected from prednisone and prednisolone. Preferably the immunosuppressive therapy is selected from methylprednisolone, mycophenolate, azathioprine, antiinflammatory antibiotics (e.g. dapsone) and cyclophosphamide. Preferably the immunosuppressive biological therapies is selected from rituximab, and intravenous immunoglobulin G (IVIG).

When the agent of the invention and a second AIBD treatment are used, they may be administered together or separately. The agent of the invention may be administered first and the second AIBD treatment may be administered second, or vice versa.

Thus, where the agent of the invention is used in combination with one or more other AIBD treatments, e.g. in methods described as above, this can be described an agent which is a protein comprising amino acids 19 to 168 of the amino acid sequence in FIG. 2 (SEQ ID NO: 2) or a functional equivalent of this protein for use in a method of treating or preventing AIBD with a second AIBD treatment, or as a second AIBD treatment for use in a method of treating or preventing AIBD with an agent which is a protein comprising amino acids 19 to 168 of the amino acid sequence in FIG. 2 (SEQ ID NO: 2) or a functional equivalent of this protein.

Where the treatment gives rise to a reduction in the amount of the second AIBD treatment, or in the duration of the treatment with the second AIBD, the reduction may be up to or at least 10, 20, 30, 40, 50, 60, 70, 80% compared to the amount of the second AIBD treatment that is used in the absence of the agent of the invention.

Subjects

Preferred subjects, agents, doses and the like are as disclosed herein.

Any reference to any reduction or increase is a reduction or increase in a disease parameter is compared to said subject in the absence of the treatment. Preferably, the parameter can be quantitated and where this is the case the increase or decrease is preferably statistically significant. For example the increase or decrease may be at least 3, 5, 10, 15, 20, 30, 40, 50% or more compared to the parameter in the absence of treatment (e.g. before said treatment is started).

The subject to which the agent is administered in the practice of the invention is preferably a mammal, preferably a human. The subject to which the agent is administered is at risk of an AIBD or a subject who has an AIBD.

Methods of the invention may also comprise one or more additional steps of (i) determining whether the subject is at risk of or has an AIBD, (ii) determining the severity of the AIBD, which may be carried out before and/or after administration of Coversin.

Agent to be Used in the Invention

According to one embodiment of the invention, the agent is Coversin itself or a functional equivalent thereof. In the following, the term "a Coversin-type protein" is used as shorthand for "a protein comprising amino acids 19 to 168 of the amino acid sequence shown in FIG. 2 (SEQ ID NO: 2) or a functional equivalent thereof".

Coversin was isolated from the salivary glands of the tick *Ornithodoros moubata*. Coversin is an outlying member of the lipocalin family and is the first lipocalin family member shown to inhibit complement activation. Coversin inhibits the classical, alternative and lectin complement pathways by binding to C5 and preventing its cleavage by C5 convertase into C5a and C5b, thus inhibiting both the production of C5a, which is an active (e.g. proinflammatory) peptide, and the formation of the MAC. Coversin has been demonstrated to bind to C5 and prevent its cleavage by C5 convertase in rat, mouse and human serum with an IC50 of approximately 0.02 mg/ml.

A Coversin-type protein may thus comprise or consist of amino acids 19 to 168 of the amino acid sequence in FIG. 2 (SEQ ID NO: 2) or amino acids 1 to 168 of the amino acid sequence in FIG. 2 (SEQ ID NO: 2). The first 18 amino acids of the protein sequence given in FIG. 2 form a signal sequence which is not required for C5 binding or for LTB4 binding activity and so this may optionally be dispensed with, for example, for efficiency of recombinant protein production.

The Coversin protein has been demonstrated to bind to C5 with a Kd of 1 nM, determined using surface plasmon resonance (SPR) [31]. Coversin-type peptides (e.g. functional equivalents of the Coversin protein) preferably retain the ability to bind C5, conveniently with a Kd of less than 360 nM, more conveniently less than 300 nM, most conveniently less than 250 nM, preferably less than 200 nM, more preferably less than 150 nM, most preferably less than 100 nM, even more preferably less than 50, 40, 30, 20, or 10 nM, and advantageously less than 5 nM, wherein said Kd is determined using surface plasmon resonance, preferably in accordance with the method described in [31].

Coversin inhibits the classical complement pathway, the alternative complement pathway and the lectin complement pathway. Preferably, a Coversin-type protein binds to C5 in such a way as to stabilize the global conformation of C5 but not directly block the C5 cleavage site targeted by the C5 convertases of the three activation pathways. Binding of Coversin to C5 results in stabilization of the global conformation of C5 but does not block the convertase cleavage site. Functional equivalents of Coversin also preferably share these properties.

C5 is cleaved by the C5 convertase enzyme (FIG. 1). The products of this cleavage include an anaphylatoxin C5a and a lytic complex C5b which promotes the formation of a complex of C5b, C6, C7, C8 and C9, also known as membrane attack complex (MAC). C5a is a highly proinflammatory peptide implicated in many pathological inflammatory processes including neutrophil and eosinophil chemotaxis, neutrophil activation, increased capillary permeability and inhibition of neutrophil apoptosis [32].

Monoclonal antibodies and small molecules that bind and inhibit C5 have been developed to treat various diseases [33], in particular PNH, psoriasis, rheumatoid arthritis, systemic lupus erythematosus and transplant rejection. However, some of these monoclonal antibodies do not bind to certain C5 proteins from subjects with C5 polymorphisms, and are thus ineffective in these subjects [34]. Preferably, the Coversin-type protein binds to and inhibits cleavage of not only wild-type C5 but also C5 from subjects with C5 polymorphisms (e.g. C5 polymorphisms that render treatment by eculizumab ineffective, or reduce the efficacy of treatment with eculizumab). The term "C5 polymorphism" includes any version of C5 which has been changed by insertion, deletion, amino acid substitution, a frame-shift, truncation, any of which may be single or multiple, or a combination of one or more of these changes compared to the wild-type C5. In a human subject, wild-type C5 is considered the C5 protein with accession number NP_001726.2; version GI:38016947. Examples of C5 polymorphisms include polymorphisms at amino acid position 885, e.g. Arg885Cys (encoded by c.2653C>T) p.Arg885His (encoded by c.2654G>A) and Arg885Ser, which decrease the effectiveness of the mAb eculizumab [34].

The ability of an agent to bind C5, including C5 from subjects with C5 polymorphisms, e.g. C5 polymorphisms that render treatment by eculizumab ineffective, or reduce the efficacy of treatment with eculizumab may be determined by standard in vitro assays known in the art, for example by surface plasmon resonance or western blotting following incubation of the protein on the gel with labelled C5. Preferably, the Coversin-type protein binds C5, either wild-type and/or C5 from subjects with C5 polymorphisms, e.g. C5 polymorphisms that render treatment by eculizumab ineffective, or reduce the efficacy of treatment with eculizumab, with a Kd of less than 360 nM, more conveniently less than 300 nM, most conveniently less than 250 nM, preferably less than 200 nM, more preferably less than 150 nM, most preferably less than 100 nM, even more preferably less than 50, 40, 30, 20, or 10 nM, and advantageously less than 5 nM, wherein said Kd is determined using surface plasmon resonance, preferably in accordance with the method described in [31].

It may show higher, lower or the same affinity for wild-type C5 and C5 from subjects with C5 polymorphisms, e.g. C5 polymorphisms that render treatment by eculizumab ineffective, or reduce the efficacy of treatment with eculizumab.

The ability of a Coversin-type protein to inhibit complement activation may also be determined by measuring the ability of the agent to inhibit complement activation in serum. For example, complement activity in the serum can be measured by any means known in the art or described herein.

The Coversin-type protein may also be defined as having the function of inhibiting eicosanoid activity. Coversin has also been demonstrated to bind LTB4. Functional equivalents of the Coversin protein may also retain the ability to bind LTB4 with a similar affinity as the Coversin protein. If the Coversin-type protein does not retain C5-binding ability, such a Coversin-type protein should retain significant LTB-4-binding ability.

The ability of a Coversin-type protein to bind LTB4 may be determined by standard in vitro assays known in the art, for example by means of a competitive ELISA between Coversin and anti-LTB4 antibody competing for binding to labelled LTB4, by isothermal titration calorimetry or by fluorescence titration. Data obtained using fluorescence titration shows that Coversin binds to LTB4 with a Kd of between 200 and 300 pM. For example, Binding activity for LTB4 (Caymen Chemicals, Ann Arbor, Mich., USA) in phosphate buffered saline (PBS) can be quantified in a spectrofluorimeter e.g. a LS 50 B spectrofluorimeter (Perkin-Elmer, Norwalk, Conn., USA). This may be carried out by may be carried out as follows:

Purified 100 nM solutions of Coversin, in 2 mL PBS were applied in a quartz cuvette (10 mm path length; Hellma, Malheim, Germany) equipped with a magnetic stirrer. Temperature was adjusted to 20° C. and, after equilibrium was reached, protein Tyr/Trp fluorescence was excited at 280 nm (slit width: 15 nm). The fluorescence emission was measured at 340 nm (slit width: 16 nm) corresponding to the emission maximum. A ligand solution of 30 μM LTB4 in PBS was added step-wise, up to a maximal volume of 20 μL (1% of the whole sample volume), and after 30 s incubation steady state fluorescence was measured. For calculation of the KD value, data was normalized to an initial fluorescence intensity of 100%, the inner filter effect was corrected using a titration of 3 μM N-acetyl-tryptophanamide solution and data was plotted against the corresponding ligand concentration. Then, non-linear least squares regression based on the law of mass action for bimolecular complex formation was used to fit the data with Origin software version 8.5 (OriginLab, Northampton, Mass., USA) using a published formula (Breustedt et al., 2006) [35].

Coversin may bind LTB4 with an with a Kd of less than 1 nM, more conveniently less than 0.9 nM, most conveniently less than 0.8 nM, preferably less than 0.7 nM, more preferably less than 0.6 nM, most preferably less than 0.5 nM, even more preferably less than 0.4 nM, and advantageously less than 0.3 nM, wherein said Kd is determined using fluorescence titration, preferably in accordance with the method above. The Coversin-type protein preferably shares these properties.

The Coversin-type proteins (e.g. the modified Coversin polypeptides which have reduced or absent C5-binding activity but which retain LTB-4-binding ability) may e.g. bind LTB4 with an with a Kd of less than 5 nM, 2 nM or 1 nM, more conveniently less than 0.9 nM, most conveniently less than 0.8 nM, preferably less than 0.7 nM, more preferably less than 0.6 nM, most preferably less than 0.5 nM, even more preferably less than 0.4 nM, and advantageously less than 0.3 nM, wherein said Kd is determined using fluorescence titration, preferably in accordance with the method above.

According to one embodiment of the invention, the Coversin-type protein may bind to both wild-type C5 and C5 from subjects with C5 polymorphisms, e.g. C5 polymorphisms that render treatment by eculizumab ineffective, or reduce the efficacy of treatment with eculizumab, and to LTB4.

The Coversin-type protein may thus act to prevent the cleavage of complement C5 by C5 convertase into complement C5a and complement C5b, and also to inhibit LTB4 activity. Using an agent which binds to both C5 and LTB4 is particularly advantageous. C5 and the eicosanoid pathway are may both contribute to the observed pathology in AIBD. Thus by using a single agent which inhibits multiple pathways involved in the AIBD an enhanced effect can be achieved, compared to using an agent which inhibits only a single pathway involved in the inflammatory effects of complement-mediated diseases and disorders. There are furthermore practical advantages associated with administering a single molecule.

Preferably, the agent of the invention is derived from a haematophagous arthropod. The term "haematophagous arthropod" includes all arthropods that take a blood meal from a suitable host, such as insects, ticks, lice, fleas and mites. Preferably, the agent is derived from a tick, preferably from the tick *Ornithodoros moubata*.

A functional equivalent of Coversin may be a homologue or fragment of Coversin which retains its ability to bind to C5, either wild-type C5 or C5 from a subject with a C5 polymorphism, and to prevent the cleavage of C5 by C5 convertase into C5a and C5b. The homologue or fragment may also retain its ability to bind LTB4.

A functional equivalent of Coversin may also be a molecule which is structurally similar to Coversin or which contains similar or identical tertiary structure, particularly in the environment of the active site or active sites of Coversin which binds to C5, either wild-type C5 or C5 from a subject with a C5 polymorphism e.g. C5 polymorphisms that render treatment by eculizumab ineffective, or reduce the efficacy of treatment with eculizumab, and/or LTB4, such as synthetic molecules. The precise amino acid residues in Coversin which are required for binding to C5 and to LTB4 are set out on the Jore et. al. reference given above.

Homologues include paralogues and orthologues of the Coversin sequence that is explicitly identified in FIG. 2, including, for example, the Coversin protein sequence from other tick species, including *Rhipicephalus appendiculatus, R. sanguineus, R. bursa, A. americanum, A. cajennense, A. hebraeum, Boophilus microplus, B. annulatus, B. decoloratus, Dermacentor reticulatus, D. andersoni, D. marginatus, D. variabilis, Haemaphysalis inermis, Ha. leachii, Ha. punctata, Hyalomma anatolicum anatolicum, Hy. dromedarii, Hy. marginatum marginatum, Ixodes ricinus, I. persulcatus, I. scapularis, I. hexagonus, Argas persicus, A. reflexus, Ornithodoros erraticus, O. moubata moubata, O. m. porcinus,* and *O. savignyi.*

The term "homologue" is also meant to include the equivalent Coversin protein sequence from mosquito species, including those of the *Culex, Anopheles* and *Aedes* genera, particularly *Culex quinquefasciatus, Aedes aegypti* and *Anopheles gambiae*; flea species, such as *Ctenocephalides felis* (the cat flea); horseflies; sandflies; blackflies; tsetse flies; lice; mites; leeches; and flatworms. The native Coversin protein is thought to exist in *O. moubata* in another three forms of around 18 kDa and the term "homologue" is meant to include these alternative forms of Coversin.

Methods for the identification of homologues of the Coversin sequence given in FIG. 2 will be clear to those of skill in the art. For example, homologues may be identified by homology searching of sequence databases, both public and private. Conveniently, publicly available databases may be used, although private or commercially-available databases will be equally useful, particularly if they contain data not represented in the public databases. Primary databases are the sites of primary nucleotide or amino acid sequence data deposit and may be publicly or commercially available. Examples of publicly-available primary databases include the GenBank database (http://www.ncbi.nlm.nih.gov/), the EMBL database (http://www.ebi.ac.uk/), the DDBJ database (http://www.ddbj.nig.ac.jp/), the SWISS-PROT protein database (http://expasy.hcuge.ch/), PIR (http://pir.georgetown.edu/), TrEMBL (http://www.ebi.ac.uk/), the TIGR databases (see http://www.tigr.org/tdb/index.html), the NRL-3D database (http://www.nbrfa.georgetown.edu), the Protein Data Base (http://www.rcsb.org/pdb), the NRDB database (ftp://ncbi.nlm.nih.gov/pub/nrdb/README), the OWL database (http://www.biochem.ucl.ac.uk/bsm/dbbrowser/OWL/) and the secondary databases PRO SITE (http://expasy.hcuge.ch/sprot/prosite.html), PRINTS (http://iupab.leeds.ac.uk/bmb5dp/prints.html), Profiles (http://ulrec3.unil.ch/software/PFSCAN_form.html), Pfam (http://www.sanger.ac.uk/software/pfam), Identify (http://dna.stanford.edu/identify/) and Blocks (http://www.blocks.fhcrc.org) databases. Examples of commercially-available databases or private databases include PathoGenome (Genome Therapeutics Inc.) and PathoSeq (previously of Incyte Pharmaceuticals Inc.).

Typically, greater than 30% identity between two polypeptides (preferably, over a specified region such as the active site) is considered to be an indication of functional equivalence and thus an indication that two proteins are homologous. Preferably, proteins that are homologues have a degree of sequence identity with the Coversin protein sequence identified in FIG. 2 (SEQ ID NO:2) of greater than 60%. More preferred homologues have degrees of identity of greater than 70%, 80%, 90%, 95%, 98% or 99%, respectively with the Coversin protein sequence given in FIG. 2 (SEQ ID NO:2). Percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1]. The % identity may be over the full length of the relevant reference sequence (e.g. amino acids 1-168 of SEQ ID NO:2 or amino acids 19-168 of SEQ ID NO:2). Coversin-type proteins thus can be described by reference to a certain % amino acid sequence identity to a reference sequence e.g. amino acids 19-168 of FIG. 2, SEQ ID NO:2 or amino acids 1-168 of FIG. 2, SEQ ID NO:2 e.g. as a protein comprising or consisting of a sequence having at least 60%, 70%, 80%, 90%, 95%, 98% or 99% identity to amino acids 19-168 of FIG. 2, SEQ ID NO:2 or amino acids 1-168 of FIG. 2, SEQ ID NO:2), Where the Coversin-type protein comprises said sequence, the Coversin-type protein may be a fusion protein (with e.g. another protein, e,g. a heterologous protein). Suitable second proteins are discussed below.

Functional equivalents of the Coversin protein sequence given in FIG. 2 include mutants containing amino acid substitutions, insertions or deletions from the wild type sequence, for example, of 1, 2, 3, 4, 5, 7, 10 or more amino acids, or up to 1, 2, 3, 4, 5, 7 or 10 amino acids, (e.g. deletions from the N or C terminus) provided that such mutants retain the ability to bind wild-type C5 and/or C5 from subjects with a C5 polymorphism (e.g. C5 polymorphisms that render treatment by eculizumab ineffective, or reduce the efficacy of treatment with eculizumab) and/or LTB4. This is relative to the relevant reference sequence (e.g. amino acids 1-168 of SEQ ID NO:2 or amino acids 19-168 of SEQ ID NO:2). Mutants thus include proteins containing conservative amino acid substitutions that do not affect the function or activity of the protein in an adverse manner. This term is also intended to include natural biological variants (e.g. allelic variants or geographical variations within the species from which the Coversin proteins are derived). Mutants with improved ability to bind wild-type C5 and/or C5 from subjects with a C5 polymorphism (e.g. C5 polymorphisms that render treatment by eculizumab ineffective, or reduce the efficacy of treatment with eculizumab) and/or LTB4 may also be designed through the systematic or directed mutation of specific residues in the protein sequence.

Functional equivalents of Coversin include fragments of the Coversin protein providing that such fragments retain the ability to bind wild-type C5 and/or C5 from subjects with a C5 polymorphism (e.g. C5 polymorphisms that render treatment by eculizumab ineffective, or reduce the efficacy of treatment with eculizumab) and/or LTB4. Fragments may include, for example, polypeptides derived from the Coversin protein sequence (or homologue) which are less than 150 amino acids, less than 145amino acids, provided that these fragments retain the ability to bind to complement wild-type C5 and/or C5 from subjects with a C5 polymorphism (e.g. C5 polymorphisms that render treatment by eculizumab ineffective, or reduce the efficacy of treatment with eculizumab) and/or LTB4. Fragments may include, for example, polypeptides derived from the Coversin protein sequence (or homologue) which are at least 150 amino acids, at least 145, amino acids, provided that these fragments retain the ability to bind to complement wild-type C5 and/or C5 from subjects with a C5 polymorphism (e.g. C5 polymorphisms that render treatment by eculizumab ineffective, or reduce the efficacy of treatment with eculizumab) and/or LTB4.

Any functional equivalent or fragment thereof preferably retains the pattern of cysteine residues that is found in Coversin. For example, said functional equivalent comprises six cysteine residues that are spaced relative to each other at a distance of 32 amino acids apart, 62 amino acids apart, 28 amino acids apart, 1 amino acid apart and 21 amino acids apart as arranged from the amino terminus to the carboxyl terminus of the sequence according to amino acids 1 to 168 of the amino acid sequence in FIG. 2 (SEQ ID NO:2). Exemplary fragments of Coversin protein are disclosed in SEQ ID NO: 4, SEQ ID NO: 6, SEQ ID NO: 8, SEQ ID NO: 10, SEQ ID NO: 12, SEQ ID NO: 14. The DNA encoding the corresponding fragments are disclosed in SEQ ID NO: 3, SEQ ID NO: 5, SEQ ID NO: 7, SEQ ID NO: 9, SEQ ID NO: 11, SEQ ID NO: 13.

Included as such fragments are not only fragments of the *O. moubata* Coversin protein that is explicitly identified herein in FIG. 2, but also fragments of homologues of this protein, as described above. Such fragments of homologues will typically possess greater than 60% identity with fragments of the Coversin protein sequence in FIG. 2, although more preferred fragments of homologues will display degrees of identity of greater than 70%, 80%, 90%, 95%, 98% or 99%, respectively with fragments of the Coversin protein sequence in FIG. 2. Preferably such fragment will retain the cysteine spacing referred to above. Fragments with improved properties may, of course, be rationally designed by the systematic mutation or fragmentation of the wild type sequence followed by appropriate activity assays. Fragments may exhibit similar or greater affinity for C5, either the wild-type or polymorphic variant of C5 or both, and/or LTB4 as Coversin. These fragments may be of a size described above for fragments of the Coversin protein.

As discussed above, Coversin-type proteins preferably bind to both wild-type C5 and/or C5 from subjects with a C5 polymorphism (e.g. C5 polymorphisms that render treatment by eculizumab ineffective, or reduce the efficacy of treatment with eculizumab) and LTB4. Coversin-type proteins that have reduced or absent C5 binding ability but which do retain LTB4 binding activity may also be used in the present invention.

Coversin-type proteins which do not retain C5-binding ability but which do retain LTB-4-binding activity are disclosed, for instance, in co-pending UK patent application No. GB 1706406.4 (Applicant's reference P070475GB) filed on 21 Apr. 2017, as well as International application No. PCT/EP2018/XXXXXX (Applicant's reference P070475WO) filed on the same day as the present application was filed, the entire contents of which are incorporated herein by reference. Such Coversin-type proteins which have reduced or absent C5-binding activity but which retain LTB-4-binding ability may be used in all aspects of the present invention.

Such Coversin-type proteins which have reduced or absent C5-binding activity but which retain LTB-4-binding ability may comprise or consist of the following sequences:

SEQ ID NO: 22 (SEQ ID NO: 5 of GB 1706406.4) is the amino acid sequence of a modified Coversin in which SEQ ID NO: 4 has been modified to change Met114 to Gln, Met116 to Gln, Leu117 to Ser, Asp118 to Asn, Ala119 to Gly, Gly120 to Ser, Gly121 to Ala, Leu122 to Asp, Glu123 to Asp and Val124 to Lys. (Coversin variant 1)

SEQ ID NO: 23 (SEQ ID NO: 6 of GB 1706406.4) is the amino acid sequence of a modified Coversin in which SEQ ID NO: 4 has been modified to change Ala44 to Asn, Met116 to Gln, Leu117 to Ser, Gly121 to Ala, Leu122 to Asp, Glu123 to Ala and Asp149 to Gly. (Coversin variant 2)

SEQ ID NO: 24 (SEQ ID NO: 7 of GB 1706406.4) is the amino acid sequence of a modified Coversin in which SEQ ID NO: 4 has been modified to change Ala44 to Asn, Met116 to Gln, Leu122 to Asp and Asp149 to Gly. (Coversin variant 3)

SEQ ID NO: 25 (SEQ ID NO: 8 of GB 1706406.4) is the amino acid sequence of a modified Coversin in which SEQ ID NO: 4 has been modified to change Ala44 to Asn. (Coversin variant 4)

SEQ ID NO: 26 (SEQ ID NO: 9 of GB 1706406.4) is the amino acid sequence of the loop between beta H and alpha2 at amino acid positions 114 to 124 of SEQ ID NO: 4 (amino acid positions 132-142 of SEQ ID NO: 2).

SEQ ID NO: 27 (SEQ ID NO: 10 of GB 1706406.4) is the amino acid sequence of the loop between beta H and alpha2 at amino acid positions 114 to 124 of SEQ ID NO: 4 in Coversin variant 1 (SEQ ID NO: 22).

SEQ ID NO: 28 (SEQ ID NO: 11 of GB 1706406.4) is the amino acid sequence of the loop between beta H and alpha2 at amino acid positions 114 to 124 of SEQ ID NO: 4 in Coversin variant 2 (SEQ ID NO: 23).

SEQ ID NO: 29 (SEQ ID NO: 12 of GB 1706406.4) is the amino acid sequence of the loop between beta H and alpha2 at amino acid positions 114 to 124 of SEQ ID NO: 4 in Coversin variant 3 (SEQ ID NO: 24).

The Coversin-type polypeptides which have reduced or absent C5-binding activity but which retain LTB-4-binding ability may be described as modified Coversin polypeptides (e.g which exhibit leukotriene or hydroxyeicosanoid binding activity and reduced or absent C5 binding). References to a "modified Coversin polypeptide" are to be understood as a reference to a modified version of either SEQ ID NO: 2 or SEQ ID NO: 4 i.e. the Coversin polypeptide with or without the 18 amino acid signal sequence seen at the N-terminus of SEQ ID NO: 2.

Such polypeptides may exhibit leukotriene or hydroxyeicosanoid binding activity and reduced or absent C5 binding and can comprise SEQ ID NO: 4 in which from 1 to 30 amino acid substitutions are made, wherein (i) in the positions 114 to 124 of SEQ ID NO: 4 one or more of the following substitutions (a)-(j) is made:

a. Met114 is replaced with Gln, Asp, Asn, Glu, Arg, Lys, Gly, Ala, Pro, His, or Thr;
  b. Met116 is replaced with Gln, Asp, Asn, Glu, Arg, Lys, Gly, Ala, Pro, His, or Thr;
  c. Leu117 is replaced with Ser, Asp, Asn, Glu, Arg, Lys, Gly, Ala, or Pro;
  d. Asp118 is replaced with Asn, Gln, Arg, Lys, Gly, Ala, Leu, Ser, Ile, Phe, Tyr, Met Pro, His, or Thr;
  e. Ala119 is replaced with Gly, Asp, Asn, Glu, Arg, Lys, Leu, Ile, Phe, Tyr, Met, Pro, or His;
  f. Gly120 is replaced with Ser, Asp, Asn, Glu, Arg, Lys, Leu, Ile, Phe, Tyr, Met, Pro, or His;
  g. Gly121 is replaced with Ala, Asp, Asn, Glu, Arg, Lys, Leu, Ile, Phe, Tyr, Met, Pro, or His;
  h. Leu122 is replaced with Asp, Glu, Asn, Ala, Gln, Arg, Lys, Pro, or His;
  i. Glu123 is replaced with Asp, Ala, Gln, Asn, Arg, Lys, Gly, Leu, Ser, Ile, Phe, Tyr, Pro, His, or Thr;
  j. Val124 is replaced with Lys, Gln, Asn, Arg, Lys, Gly, Ala, Pro, His, or Thr; or/and wherein (ii) Ala44 in SEQ ID NO: 4 is replaced with Asn, Asp, Gln, Glu, Arg, Lys, Leu, Ile, Phe, Tyr, Met, Pro, or His;

or a fragment thereof in which up to five amino acids are deleted from the N terminus of the modified Coversin polypeptide.

LK/E binding activity as used herein refers to the ability to bind to leukotrienes and hydroxyeicosanoids including but not limited to LTB4, B4 isoleukotrienes and any hydroxylated derivative thereof, HETEs, HPETEs and EETs. LTB4 binding is of particular interest.

The modified Coversin polypeptides which have reduced or absent C5-binding activity but which retain LTB-4-binding ability may consist of SEQ ID NO: 2 or 4, modified in accordance with the description below, or may comprise SEQ ID NO: 2 or 4, modified in accordance with the description below.

The unmodified Coversin polypeptide in SEQ ID NO: 2 and SEQ ID NO: 4 features a loop between beta H and alpha2 at amino acid positions 114 to 124 of SEQ ID NO: 4 (amino acid positions 132-142 of SEQ ID NO: 2). This loop has the sequence shown below: -Met-Trp-Met-Leu-Asp-Ala-Gly-Gly-Leu-Glu-Val- (SEQ ID NO: 26)

The first Met is at position 114 of SEQ ID NO: 4 and at position 132 of SEQ ID NO: 2.

In the modified Coversin polypeptide which has reduced or absent C5-binding activity but which retains LTB-4-binding ability, the Coversin polypeptide of SEQ ID NO: 2 or SEQ ID NO: 4 is modified such that at positions 114 to 124 of SEQ ID NO: 4 one or more of the following substitutions (a)-(j) is made:

a. Met114 is replaced with Gln, Asp, Asn, Glu, Arg, Lys, Gly, Ala, Pro, His, or Thr, preferably Gln or Ala;
  b. Met116 is replaced with Gln, Asp, Asn, Glu, Arg, Lys, Gly, Ala, Pro, His, or Thr, preferably Gln or Ala;
  c. Leu117 is replaced with Ser, Asp, Asn, Glu, Arg, Lys, Gly, Ala, or Pro, preferably Ser or Ala;
  d. Asp118 is replaced with Asn, Gln, Arg, Lys, Gly, Ala, Leu, Ser, Ile, Phe, Tyr, Met Pro, His, or Thr, preferably Asn;
  e. Ala119 is replaced with Gly, Asp, Asn, Glu, Arg, Lys, Leu, Ile, Phe, Tyr, Met, Pro, or His, preferably Gly or Asn;
  f. Gly120 is replaced with Ser, Asp, Asn, Glu, Arg, Lys, Leu, Ile, Phe, Tyr, Met, Pro, or His, preferably Ser or Asn;
  g. Gly121 is replaced with Ala, Asp, Asn, Glu, Arg, Lys, Leu, Ile, Phe, Tyr, Met, Pro, or His, preferably Ala or Asn;
  h. Leu122 is replaced with Asp, Glu, Asn, Ala, Gln, Arg, Lys, Pro, or His, preferably Asp or Ala;
  i. Glu123 is replaced with Asp, Ala, Gln, Asn, Arg, Lys, Gly, Leu, Ser, Ile, Phe, Tyr, Pro, His, or Thr, preferably Asp, Ala, Gln or Asn;
  j. Val124 is replaced with Lys, Gln, Asn, Arg, Lys, Gly, Ala, Pro, His, or Thr, preferably Lys or Ala.

In the modified Coversin polypeptide which has reduced or absent C5-binding activity but which retains LTB-4-binding ability the Coversin polypeptide in SEQ ID NO: 2 or SEQ ID NO: 4 can be modified such that at positions 114 to 124 of SEQ ID NO: 4 one or more of the following substitutions (a)-(j) is made:

a. Met114 is replaced with Gln;
  b. Met116 is replaced with Gln;
  c. Leu117 is replaced with Ser;
  d. Asp118 is replaced with Asn;
  e. Ala119 is replaced with Gly;
  f. Gly120 is replaced with Ser;
  g. Gly121 is replaced with Ala;
  h. Leu122 is replaced with Asp;
  i. Glu123 is replaced with Asp, or Ala;
  j. Val124 is replaced with Lys.

In the modified Coversin polypeptide two, three, four, five, six, seven, eight, nine, or ten of the substitutions (a)-(j)

are present. Preferably two or more, five or more, or eight or more of the substitutions (a)-(j) are present.

In the modified Coversin polypeptide which has reduced or absent C5-binding activity but which retains LTB-4-binding ability the Coversin polypeptide in SEQ ID NO: 2 or SEQ ID NO: 4 can be modified such that at positions 114 to 124 of SEQ ID NO: 4 the following substitutions are present:
  a. Met114 is replaced with Gln;
  b. Met116 is replaced with Gln;
  c. Leu117 is replaced with Ser;
  d. Asp118 is replaced with Asn;
  e. Ala119 is replaced with Gly;
  f. Gly120 is replaced with Ser;
  g. Gly121 is replaced with Ala;
  h. Leu122 is replaced with Asp;
  i. Glu123 is replaced with Asp;
  j. Val124 is replaced with Lys.

Optionally in the modified Coversin polypeptide referred to above Trp115 is not substituted. A preferred modified Coversin polypeptide has a loop between beta H and alpha2 at amino acid positions 114 to 124 of SEQ ID NO: 4 that has the sequence Gln-Trp-Gln-Ser-Asn-Gly-Ser-Ala-Asp-Asp-Lys (SEQ ID NO: 27).

In the modified Coversin polypeptide which has reduced or absent C5-binding activity but which retains LTB-4-binding ability, the Coversin polypeptide can be modified such that at positions 114 to 124 of SEQ ID NO: 4 the following substitutions are present:
  a. Met114 is replaced with Gln, Asp, Asn, Glu, Arg, Lys, Gly, Ala, Pro, His, or Thr, preferably Gln;
  b. Leu117 is replaced with Ser, Asp, Asn, Glu, Arg, Lys, Gly, Ala, or Pro, preferably Ser;
  c. Gly121 is replaced with Ala, Asp, Glu, Arg, Lys, Leu, Ile, Phe, Tyr, Met, Pro, or His, preferably Ala;
  d. Leu122 is replaced with Asp, Glu, Asn, Gln, Arg, Lys, Pro, or His, preferably Asp;
  e. Glu123 is replaced with Asp, Ala, Gln, Asn, Arg, Lys, Gly, Leu, Ser, Ile, Phe, Tyr, Pro, His, or Thr, preferably Asp.

In more particular embodiments;
  a. Met116 is replaced with Gln;
  b. Leu117 is replaced with Ser;
  c. Gly121 is replaced with Ala;
  d. Leu122 is replaced with Asp;
  e. Glu123 is replaced with Ala.

Optionally in this modified Coversin polypeptide referred to above Trp 115 is not substituted. Optionally in this embodiment Met114, Trp 115, Asp118, Ala119, Gly120 and Val124 are not substituted, or are substituted with conservative substitutions as referred to elsewhere herein. A preferred modified Coversin polypeptide which has reduced or absent C5-binding activity but which retains LTB-4-binding ability has a loop between beta H and alpha2 at amino acid positions 114 to 124 of SEQ ID NO: 4 that has the sequence Met-Trp-Gln-Ser-Asp-Ala-Gly-Ala-Asp-Ala-Val (SEQ ID NO: 28).

In the modified Coversin polypeptide which has reduced or absent C5-binding activity but which retains LTB-4-binding ability, the Coversin polypeptide can be modified such that at positions 114 to 124 of SEQ ID NO: 4 the following substitutions are present:
  a. Met116 is replaced with Gln, Asp, Asn, Glu, Arg, Lys, Gly, Ala, Pro, His, or Thr, preferably Gln;
  b. Leu122 is replaced with Asp, Glu, Asn, Gln, Arg, Lys, Pro, or His, preferably Asp;

In more particular embodiments;
  a. Met116 is replaced with Gln;
  b. Leu122 is replaced with Asp.

Optionally in this modified Coversin polypeptide referred to above Trp 115 is not substituted. Optionally in this embodiment Met114, Trp 115, Leu117, Asp118, Ala119, Gly120, Gly121, Glu123 and Val124 are not substituted. A preferred modified Coversin polypeptide which has reduced or absent C5-binding activity but which retains LTB-4-binding ability has a loop between beta H and alpha2 at amino acid positions 114 to 124 of SEQ ID NO: 4 that has the sequence Met-Trp-Gln-Leu-Asp-Ala-Gly-Gly-Asp-Glu-Val (SEQ ID NO: 29).

In the modified Coversin polypeptide which has reduced or absent C5-binding activity but which retains LTB-4-binding ability the Coversin polypeptide can be modified such that Ala44 in SEQ ID NO: 4 (Ala62 in SEQ ID NO: 2) is replaced with Asn, Asp, Gln, Glu, Arg, Lys, Leu, Ile, Phe, Tyr, Met, Pro, or His.

In preferred embodiments Ala44 in SEQ ID NO: 4 is replaced with Asn.

This substitution at position 44 of SEQ ID NO: 4 (or position 62 of SEQ ID NO: 2) may be made in combination with any of the other substitutions referred to herein.

In another modified Coversin polypeptide which has reduced or absent C5-binding activity but which retains LTB-4-binding ability the Coversin polypeptide can be modified such that at positions 114 to 124 of SEQ ID NO: 4 one or more of the following substitutions (a)-(j) is present:
  a. Met114 is replaced with Gln, Asp, Asn, Glu, Arg, Lys, Gly, Ala, Pro, His, or Thr, preferably Gln or Ala, e.g. Gln;
  b. Met116 is replaced with Gln, Asp, Asn, Glu, Arg, Lys, Gly, Ala, Pro, His, or Thr, preferably Gln or Ala e.g. Gln;
  c. Leu117 is replaced with Ser, Asp, Asn, Glu, Arg, Lys, Gly, Ala, or Pro, preferably Ser or Ala, e.g. Ser;
  d. Asp118 is replaced with Asn, Gln, Arg, Lys, Gly, Ala, Leu, Ser, Ile, Phe, Tyr, Met Pro, His, or Thr, preferably Asn;
  e. Ala119 is replaced with Gly, Asp, Glu, Arg, Lys, Leu, Ile, Phe, Tyr, Met, Pro, or His, preferably Gly or Asn, e.g. Gly;
  f. Gly120 is replaced with Ser, Asp, Glu, Arg, Lys, Leu, Ile, Phe, Tyr, Met, Pro, or His, preferably Ser or Asn, e.g. Ser;
  g. Gly121 is replaced with Ala, Asp, Glu, Arg, Lys, Leu, Ile, Phe, Tyr, Met, Pro, or His preferably Ala or Asn, e.g. Ala;
  h. Leu122 is replaced with Asp, Glu, Asn, Gln, Arg, Lys, Pro, or His, preferably Asp or Ala, e.g. Asp;
  i. Glu123 is replaced with Asp, Ala, Gln, Asn, Arg, Lys, Gly, Leu, Ser, Ile, Phe, Tyr, Pro, His, or Thr, preferably Asp, Ala, Gln or Asn, e.g. Asp or Ala;
  j. Val124 is replaced with Lys, Gln, Asn, Arg, Lys, Gly, Ala, Pro, His, or Thr, preferably Lys or Ala, e.g. Lys;
  and additionally Ala44 in SEQ ID NO: 4 (Ala62 in SEQ ID NO: 2) is replaced with Asn, Asp, Gln, Glu, Arg, Lys, Leu, Ile, Phe, Tyr, Met, Pro, or His, preferably Asn.

In some modified Coversin polypeptides which have reduced or absent C5-binding activity but which retain LTB-4-binding ability, the Coversin polypeptide can be modified such that at positions 114 to 124 of SEQ ID NO: 4 the following substitutions are present:
  a. Met116 is replaced with Gln;
  b. Leu117 is replaced with Ser;
  c. Gly121 is replaced with Ala;
  d. Leu122 is replaced with Asp;
  e. Glu123 is replaced with Ala;
  and Ala44 in SEQ ID NO: 4 is replaced with Asn.

In preferred aspects of this embodiment the amino acid residues corresponding to positions 114 to 124 of SEQ ID NO: 4 are as set out in SEQ ID NO: 28.

In some modified Coversin polypeptides which have reduced or absent C5-binding activity but which retain LTB-4-binding ability, the Coversin polypeptide is modified such that at positions 114 to 124 of SEQ ID NO: 4 the following substitutions are present:
a. Met116 is replaced with Gln;
b. Leu122 is replaced with Asp;
and Ala44 in SEQ ID NO: 4 is replaced with Asn In preferred aspects of this embodiment the amino acid residues corresponding to positions 114 to 124 of SEQ ID NO: 4 are as set out in SEQ ID NO: 29.

In some modified Coversin polypeptides which have reduced or absent C5-binding activity but which retain LTB-4-binding ability the Coversin polypeptide can be modified such that Asp149 in SEQ ID NO: 4 is replaced with Gly, Gln, Asn, Ala, Met, Arg, Lys, Leu, Ser, Ile, Phe, Tyr, Pro, His, or Thr. In some embodiments the Coversin polypeptide is modified such that Asp149 of SEQ ID NO: 4 is replaced with Gly. This substitution at position 149 of SEQ ID NO: 4 (position 167 of SEQ ID NO: 2) may be made in combination with any of the other substitutions referred to herein.

In some modified Coversin polypeptides which have reduced or absent C5-binding activity but which retain LTB-4-binding ability the Coversin polypeptide can be modified such that at positions 114 to 124 of SEQ ID NO: 4 the following substitutions are present:
a. Met116 is replaced with Gln;
b. Leu117 is replaced with Ser;
c. Gly121 is replaced with Ala;
d. Leu122 is replaced with Asp;
e. Glu123 is replaced with Ala;
Ala44 in SEQ ID NO: 4 is replaced with Asn and Asp149 of SEQ ID NO: 4 is replaced with Gly149.

In preferred aspects of this embodiment the amino acid residues corresponding to positions 114 to 124 of SEQ ID NO: 4 are as set out in SEQ ID NO: 28.

In some modified Coversin polypeptides which have reduced or absent C5-binding activity but which retain LTB-4-binding ability, the Coversin polypeptide can be modified such that at positions 114 to 124 of SEQ ID NO: 4 the following substitutions are present:
a. Met116 is replaced with Gln;
b. Leu122 is replaced with Asp;
Ala44 in SEQ ID NO: 4 is replaced with Asn and Asp149 of SEQ ID NO: 4 is replaced with Gly149.

In preferred aspects of this embodiment the amino acid residues corresponding to positions 114 to 124 of SEQ ID NO: 4 are as set out in SEQ ID NO: 29.

In the various aspects and embodiments of this disclosure, the modified Coversin polypeptides which have reduced or absent C5-binding activity but which retain LTB-4-binding ability differ from the unmodified Coversin polypeptides in SEQ ID NO: 2 and SEQ ID NO: 4 by from 1 to 30 amino acids. Any modifications may be made to the Coversin polypeptide in SEQ ID NO: 2 and SEQ ID NO: 4 provided that the resulting modified Coversin polypeptide exhibits LK/E binding activity and reduced or absent C5 binding, compared to the unmodified Coversin polypeptide.

In some embodiments the six cysteine amino acids at positions 6, 38, 100, 128, 129, 150 of SEQ ID NO: 4 are retained in the modified Coversin polypeptides of the invention.

In some modified Coversin polypeptides, Asn60 and Asn84 in SEQ ID NO: 4 are each replaced with Gln. This modification can be carried out by site directed mutagenesis to prevent N-linked hyperglycosylation when the polypeptide is expressed in yeast.

In some modified Coversin polypeptides one or more of the following amino acids in SEQ ID NO: 4 are thought to be involved in binding to LTB4 and may therefore be retained in unmodified form: Phe18, Tyr25, Arg36, Leu39, Gly41, Pro43, Leu52, Val54, Met56, Phe58, Thr67, Trp69, Phe71, Gln87, Arg89, His99, His101, Asp103, and Trp115. In some modified Coversin polypeptides, at least five, ten or fifteen, or all of these amino acids are retained in unmodified form in the modified Coversin polypeptides of the invention. In some modified Coversin polypeptides which have reduced or absent C5-binding activity but which retain LTB-4-binding ability one or more of these amino acids may be conservatively substituted. In some modified Coversin polypeptides which have reduced or absent C5-binding activity but which retain LTB-4-binding ability up to five, ten or fifteen, or all of these amino acids are conservatively substituted in the modified Coversin polypeptides of the invention.

Amino acids at the following positions in SEQ ID NO: 4 are highly conserved between Coversin and TSGP2 and TSGP3: 5, 6, 11, 13-15, 20-21, 24-27, 29-32, 35-41, 45, 47-48, 50, 52-60, 64, 66, 69-81, 83, 84, 86, 90-94, 97-104, 112-113, 115, 125-129, 132-139, 145, 148, and 150.

Amino acids at the following positions in SEQ ID NO: 4 are thought to be involved in binding to LTB4 and/or are highly conserved between Coversin and TSGP2 and TSGP3: 5, 6, 11, 13-15, 18, 20-21, 24-27, 29-32, 35-41, 43, 45, 47-48, 50, 52-60, 64, 66, 67, 69-81, 83, 84, 86, 87, 89, 90-94, 97-104, 112-113, 115, 125-129, 132-139, 145, 148, and 150.

Amino acids at the following positions in SEQ ID NO: 4 are thought to be involved in binding to LTB4 and/or are highly conserved between Coversin and TSGP2 and TSGP3: 5, 6, 11, 13-15, 18, 20-21, 24-25, 27, 30-32, 35-41, 43, 47-48, 50, 52-60, 64, 66, 67, 69-81, 83, 84, 86, 87, 89, 90-94, 98, 100, 102-104, 112-113, 115, 126, 128-129, 132-139, 145, 148, and 150.

In some modified Coversin polypeptides which have reduced or absent C5-binding activity but which retain LTB-4-binding ability therefore the above amino acids are retained in unmodified form. In some embodiments, at least five, ten or fifteen, or all of these amino acids are retained in unmodified form in the modified Coversin polypeptides of the invention. In some embodiments one or more of these amino acids may be conservatively substituted. In some embodiments up to five, ten or fifteen, twenty, twenty five, 30, 40, 50 or all of these amino acids are conservatively substituted in the modified Coversin polypeptides of the invention The modified Coversin polypeptides referred to herein typically differ from SEQ ID NO: 2 or SEQ ID NO: 4 by from 1 to 30, preferably from 2 to 25, more preferably from 3 to 20, even more preferably from 4 to 15 amino acids. Typically the difference will be 5 to 12, or 6 to 10 amino acid changes. For example, from 1 to 30, or 2 to 25, 3 to 30, 4 to 15, 5 to 12, or 6 to 10 amino acid substitutions may be made in SEQ ID NO: 2 or SEQ ID NO: 4.

Modified Coversin polypeptides which have the loop between beta H and alpha2 at amino acid positions 114 to 124 of SEQ ID NO: 4 (amino acid positions 132-142 of SEQ ID NO: 2) as set out in SEQ ID NO: 27 have 10 amino acid substitutions compared to SEQ ID NO: 4 as a result of the presence of this loop. In some embodiments, the modified Coversin polypeptides referred to herein preferably therefore have 1-15, 2-10, 3-5, or up to 2, 3, 4 or 5 additional substitutions compared to SEQ ID NO: 4 beyond those that are set out in SEQ ID NO: 22 (e.g. in the loop of SEQ ID NO: 27).

Modified Coversin polypeptides which have the loop between beta H and alpha2 at amino acid positions 114 to 124 of SEQ ID NO: 4 (amino acid positions 132-142 of SEQ ID NO: 2) as set out in SEQ ID NO: 28 have 5 amino acid substitutions compared to SEQ ID NO: 4 as a result of the presence of this loop. In some embodiments, the modified Coversin polypeptides referred to herein preferably therefore have 1-20, 2-15, 3-10, or up to 2, 3, 4, 5, 6, 7, 8, 9, 10 additional substitutions compared to SEQ ID NO: 4 beyond those that are set out in SEQ ID NO: 23 (e.g. in the loop of SEQ ID NO: 28). The additional substitutions preferably include substitutions at position 44 and 149, as set out elsewhere herein.

Modified Coversin polypeptides which have the loop between beta H and alpha2 at amino acid positions 114 to 124 of SEQ ID NO: 4 (amino acid positions 132-142 of SEQ ID NO: 2) as set out in SEQ ID NO: 29 have 2 amino acid substitutions compared to SEQ ID NO: 4 as a result of the presence of this loop. In some embodiments, the modified Coversin polypeptides preferably therefore have 1-25, 2-12, 3-15, or up to 2, 3, 4, 5, 6, 7, 8, 9, 10, 11, 12, 13, 14, 15 additional substitutions compared to SEQ ID NO: 4 beyond those that are set out in SEQ ID NO: 24 (e.g. substitutions in the loop of SEQ ID NO: 29). The additional substitutions preferably include substitutions at position 44 and 149, as set out elsewhere herein.

Modified Coversin polypeptides which have the substitution at position 44 of SEQ ID NO: 4 as set out elsewhere herein preferably have 1-25, 2-12, 3-15, or up to 2, 3, 4, 5, 6, 7, 8, 9, 10, 11, 12, 13, 14, 15 additional substitutions compared to SEQ ID NO: 4.

Substitutions other than those explicitly referred to above are preferably conservative substitutions, for example according to the following Table. Amino acids in the same block in the second column and preferably in the same line in the third column may be substituted for each other:

| Aliphatic | Non-polar | G A P |
| | | I L V |
| | Polar - uncharged | C S T M |
| | | N Q |
| | Polar - charged | D E |
| | | K R |
| Aromatic | | H F W Y |

Preferred modified Coversin polypeptides which have reduced or absent C5-binding activity but which retain LTB-4-binding ability may comprise or consist of the amino acid sequences set out in one of SEQ ID NOs: 22, 23, 24, 25.

The present invention also encompasses use of fragments of the modified Coversin polypeptide which has reduced or absent C5-binding activity but which retains LTB-4-binding ability referred to above in which up to five amino acids are deleted from the N terminus of the modified Coversin polypeptide. The fragment may correspond to 1, 2, 3, 4 or 5 deletions from the N terminus of the modified Coversin polypeptide. Deletions from other positions in the amino acid sequence of SEQ ID NO: 2 or SEQ ID NO: 4 are also envisaged as forming part of the invention, if the resulting polypeptide retains the LK/E binding activity of the modified Coversin and has reduced or absent complement inhibitor activity.

Where modified Coversin polypeptides are used that have reduced or absent C5-binding activity but which retain LTB-4-binding ability, C5 binding may for example, reduced by at least 2, 5, 10, 15, 20, 50, 100 fold, or eliminated relative to the binding exhibited by the unmodified Coversin polypeptide in SEQ ID NO: 2 or 4. C5 binding may e.g. be reduced by at least 50%, 60%, 70%, 80%, 90% or 95% relative to the unmodified Coversin polypeptide in SEQ ID NO: 2 or 4. The modified Coversin polypeptides may bind C5 with a KD greater than 1 micromolar as determined by Surface Plasma Resonance according to the method described in Roversi et al. (2013) J Biol Chem. 288, 18789-18802, or as set out in Example 2 of GB1706406.4.

A functional equivalent used according to the invention may be a fusion protein, obtained, for example, by cloning a polynucleotide encoding the Coversin protein in frame to the coding sequences for a heterologous protein sequence. The term "heterologous", when used herein, is intended to designate any polypeptide other than the Coversin protein or its functional equivalent. Example of heterologous sequences, that can be comprised in the soluble fusion proteins either at N- or at C-terminus, are the following: extracellular domains of membrane-bound protein, immunoglobulin constant regions (Fc region), PAS or XTEN or similar unstructured polypeptides, multimerization domains, domains of extracellular proteins, signal sequences, export sequences, or sequences allowing purification by affinity chromatography. Many of these heterologous sequences are commercially available in expression plasmids since these sequences are commonly included in the fusion proteins in order to provide additional properties without significantly impairing the specific biological activity of the protein fused to them [36]. Examples of such additional properties are a longer lasting half-life in body fluids (e.g. resulting from the addition of an Fc region or Pasylation [37]), the extracellular localization, or an easier purification procedure as allowed by a tag such as a histidine, GST, FLAG, avidin or HA tag. Fusion proteins may additionally contain linker sequences (e.g. 1-50 amino acids in length, such that the components are separated by this linker.

Fusion proteins are thus examples of proteins comprising a Coversin-like protein, and include by way of specific example a protein comprising a PAS sequence and a Coversin-type protein sequence. PAS sequences are described e.g. in Schlapschy M, et al [37], and EP 08773567.6, with a PASylated Coversin molecule being described in Kuhn et al [38]. PASylation describes the genetic fusion of a protein with conformationally disordered polypeptide sequences composed of the amino acids Pro, Ala, and/or Ser. This is a technology developed by XL Protein (http://xl-protein.com/) and provides a simple way to attach a solvated random chain with large hydrodynamic volume to the protein to which it is fused. The polypeptide sequence adopts a bulky random coil structure. The size of the resulting fusion protein is thus much bigger than the protein to which it is fused. This has been shown to reduce clearance in biological systems. Appropriate PAS sequences are described in EP08773567.6, as well as the Schlapschy reference above. Any suitable PAS sequence may be used in the fusion protein. Examples include an amino acid sequence consisting of at least about 100 amino acid residues forming a random coil conformation and consisting of alanine, serine and proline residues (or consisting of proline and alanine residues). This may comprise a plurality of amino acid repeats, wherein said repeats consist of Ala, Ser, and Pro residues (or proline and alanine residues) and wherein no more than 6 consecutive amino acid residues are identical. Proline residues may constitute more than 4% and less than 40% of the amino acids of the sequence. The sequence may comprise an amino acid sequence selected from:

ASPAAPAPASPAAPAPSAPA; (SEQ ID NO: 15)

AAPASPAPAAPSAPAPAAPS; (SEQ ID NO: 16)

APSSPSPSAPSSPSPASPSS, (SEQ ID NO: 17)

SAPSSPSPSAPSSPSPASPS, (SEQ ID NO: 18)

SSPSAPSPSSPASPSPSSPA, (SEQ ID NO: 19)

AASPAAPSAPPAAASPAAPSAPPA (SEQ ID NO: 20)
and

ASAAAPAAASAAASAPSAAA (SEQ ID NO: 21)

or circular permuted versions or multimers of these sequences as a whole or parts of these sequences. There may, for example be 5-40, 10-30, 15-25, 18-20 preferably 20-30 or 30 copies of one of the repeats present in the PAS sequence, i.e. one of SEQ ID NOs 15-21, preferably 15. Preferably the PAS sequence comprises or consists of 30 copies of SEQ ID NO:15. Preferably the PAS sequence is fused to the N terminus of the Coversin-type protein (directly or via a linker sequence) and in certain preferred embodiments the Coversin-type protein may comprise or consist of amino acids 19-168 of SEQ ID NO:2 (e.g. the fusion protein comprises (a) a PAS sequence consisting of 30 copies of SEQ ID NO:15 and (b) amino acids 19-168 of SEQ ID NO:2, wherein (a) is fused to the N terminus of (b) directly or via a linker sequence).

Fusion proteins may additionally contain linker sequences (e.g. 1-50, 2-30, 3-20, 5-10 amino acids in length), such that the components are separated by this linker. In one embodiment the linker sequence can be a single alanine residue.

The protein and functional equivalents thereof, may be prepared in recombinant form by expression in a host cell. Such expression methods are well known to those of skill in the art and are described in detail by [39] and [40]. Recombinant forms of the Coversin protein and functional equivalents thereof are preferably unglycosylated. Preferably the host cell is *E. coli*.

The Coversin protein and functional equivalents thereof, are preferably in isolated form, e.g. separated from at least one component of the host cell and/or cell growth media in which it was expressed. In some embodiments, the Coversin protein or functional equivalent thereof is purified to at least 90%, 95%, or 99% purity as determined, for example, by electrophoresis or chromatography. The proteins and fragments of the present invention can also be prepared using conventional techniques of protein chemistry. For example, protein fragments may be prepared by chemical synthesis. Methods for the generation of fusion proteins are standard in the art and will be known to the skilled reader. For example, most general molecular biology, microbiology recombinant DNA technology and immunological techniques can be found in [39] or [41].

According to a further embodiment of the invention, the agent may be a nucleic acid molecule encoding the Coversin-type protein. For example, gene therapy may be employed to effect the endogenous production of the Coversin-type protein by the relevant cells in the subject, either in vivo or ex vivo. Another approach is the administration of "naked DNA" in which the therapeutic gene is directly injected into the bloodstream or into muscle tissue.

Preferably, such a nucleic acid molecule comprises or consists of bases 55 to 507 of the nucleotide sequence in FIG. 2 (SEQ ID NO: 1). This nucleotide sequence encodes the Coversin protein in FIG. 2 without the signal sequence. The first 54 bases of the nucleotide sequence in FIG. 2 encode the signal sequence which is not required for complement inhibitory activity or LTB4 binding activity. Alternatively, the nucleic acid molecule may comprise or consist of bases 1 to 507 of the nucleic acid sequence in FIG. 2, which encodes the protein with the signal sequence.

Modes of Administration

Coversin-type proteins do not require a medical professional for administration to be carried out, and these molecules are rapidly absorbed. In contrast, many recombinant antibodies are absorbed very slowly and as a result need to be infused over long periods (e.g. intravenously). The administration of such molecules thus also requires a medical professional. Thus, as well as having the advantage of being more effective at inhibiting the activation of the complement pathways in subjects with a C5 polymorphism, Coversin-type proteins also possess the advantage of being easier to administer than other agents such as antibodies like eculizumab.

The agent is administered in a therapeutically or prophylactically effective amount. The term "therapeutically effective amount" refers to the amount of agent needed to treat the AIBD. In this context, "treating" includes reducing the severity of the disorder.

The term "prophylactically effective amount" used herein refers to the amount of agent needed to prevent the relevant condition, e.g. AIBD. In this context, "preventing" includes reducing the severity of the disorder, e.g. if the presence of the disorder is not detected before the administration of the agent is commenced. Reducing the severity of the disorder could be, for example, reducing the size or the number of the blisters the body surface that is affected, as discussed elsewhere herein.

The reduction or improvement is relative to the outcome without administration or the agent as described herein. The outcomes are assessed according to the standard criteria used to assess such patients. To the extent that this can be quantitated, there is a reduction or improvement of at least 10, 20, 30, 40, 50, 60, 70, 80, 90, 100% in the relative criteria (e.g. the size or number of blisters or of the body surface that is affected).

Preferably, the dose of the agent is sufficient to bind as much available C5 as possible in the subject, more preferably, all available C5. The dose of the agent may alternatively be sufficient to bind as much available LTB4 as possible in the subject, more preferably, all available LTB4. In some aspects, the dose of the agent is sufficient to binds as much available C5 and LTB4 as possible, for example all available C5 and LTB4. The dose of the agent supplied may be at least 1× or 1.5 times or twice the molar dose needed to bind all available C5 and/or LTB4 in the subject. The dose of the agent supplied may be e.g. about or at least 1, 1.5, 2, 2.5 times, 3 times or 4 times the molar dose needed to bind all available C5 and/or LTB4 in the subject.

Preferably, the dose is from 0.0001 mg/kg (mass of drug compared to mass of patient) to 20 mg/kg, 0.001 mg/kg to 10 mg/kg, 0.01 mg/kg to 2 mg/kg, 0.1 mg/kg to 1 mg/kg, 0.2 mg/kg to 0.8 mg/kg, 0.3 mg/kg to 0.6 mg/kg, 0.4 mg/kg to 0.6 mg/kg (e.g. about 0.57 mg/kg).

The therapeutically or prophylactically effective amount can additionally be defined in terms of the inhibition of terminal complement, for example, an amount that means that terminal complement activity (TCA) is reduced by at least 10, 20, 30, 40, 50, 60, 70, 80, 90, 91, 92, 93, 94, 95, 96, 97, 98, 99, 100%, compared to terminal complement activity in the absence of treatment. Dose and frequency may be adjusted in order to maintain terminal complement activity at the desired level, which may be, for example 10% or less, for example 9, 8, 7, 6, 5, 4, 3, 2, 1% or less compared to terminal complement activity in the absence of treatment.

Where a dose is given, this relates to a dose of the agent which is a protein or functional equivalent thereof. Appropriate doses for an agent which is a nucleic acid molecule may be used to give rise to these levels.

Terminal complement activity can be measured by standard assays known in the art, e.g. using the Quidel $CH_{50}$ haemolysis assay and the sheep red blood cell lytic CH50 assay.

The frequency with which the dose needs to be administered will depend on the half-life of the agent involved. The Coversin protein or a functional equivalent thereof, may be administered e.g. on a twice daily basis, daily basis, or every two, three, four days, five, six, seven, 10, 15 or 20 days or more.

Single or multiple doses may be administered. For example at least 2, 3, 4, 5, 6, 7, or 8 doses may be administered. Single doses are one embodiment. The exact dosage and the frequency of doses may also be dependent on the patient's status at the time of administration. Factors that may be taken into consideration when determining dosage include the need for treatment or prophylaxis, the severity of the disease state in the patient, the general health of the patient, the age, weight, gender, diet, time and frequency of administration, drug combinations, reaction sensitivities and the patient's tolerance or response to therapy. The precise amount can be determined by routine experimentation, but may ultimately lie with the judgment of the clinician.

The dosage regimen may also take the form of an initial "loading dose" followed by one or more subsequence "maintenance doses". In general, the loading dose will be greater than the maintenance dose. The loading dose may be 2, 5, 10 or more times greater than the maintenance dose. The loading dose may be administered as a single dose, or as one or more doses in a particular time frame. Typically, the loading dose will be 1, 2, 3, 4 or 5 doses administered in a single 24 hour period. The maintenance dose may be a lower dose that is repeated at regular intervals. The maintenance dose may be repeated at intervals, such as every 3, 4, 6, 8, 12, 24, or 48 hours. The precise regimen can be determined by routine experimentation, but may ultimately lie with the judgment of the clinician. The maintenance dose may be at least 20, 30, 40, 50, 60, 70, 80, 90 or 100% of the initial loading dose, or up to 20, 30, 40, 50, 60, 70, 80, 90 or 100% of the initial loading dose.

In a further embodiment the same dose is used throughout the course of treatment (e.g. daily or twice daily).

The loading dose may be 0.0001 mg/kg (mass of drug compared to mass of patient) to 20 mg/kg, and the maintenance dose may be between 0.0001 mg/kg to 20 mg/kg; alternatively the loading dose is 0.001 mg/kg to 10 mg/kg and the maintenance dose is 0.001 mg/kg to 10 mg/kg, alternatively the loading dose is 0.01 mg/kg to 2 mg/kg and the maintenance dose is 0.01 mg/kg to 2 mg/kg; alternatively the loading dose is 0.1 mg/kg to 1 mg/kg and the maintenance dose is 0.1 mg/kg to 1 mg/kg; alternatively the loading dose is 0.1 mg/kg to 1 mg/kg and the maintenance dose is 0.05 mg/kg to 0.5 mg/kg; alternatively the loading dose is 0.2 mg/kg to 0.8 mg/kg and the maintenance dose is 0.1 mg/kg to 0.4 mg/kg; alternatively the loading dose is 0.3 mg/kg to 0.7 mg/kg and the maintenance dose is 0.1 mg/kg to 0.3 mg/kg; alternatively the loading dose is 0.4 mg/kg to 0.6 mg/kg and the maintenance dose is 0.1 mg/kg to 0.2 mg/kg for example where the loading dose is 0.57 mg/kg and the maintenance dose is 0.14 mg/kg. For example a loading dose of 0.6 mg/kg-1.8 mg/kg followed by a maintenance dose of 0.2 mg/kg-0.6 mg/kg (for example 0.3 mg/kg).

The loading dose may be 0.0001 mg/kg (mass of drug compared to mass of patient) to 20 mg/kg, and the maintenance dose may be between 0.0001 mg/kg to 20 mg/kg; alternatively the maintenance dose may be 0.001 mg/kg to 10 mg/kg, alternatively the maintenance dose may be 0.01 mg/kg to 2 mg/kg; alternatively the maintenance dose may be 0.1 mg/kg to 1 mg/kg; alternatively the maintenance dose may be 0.1 mg/kg to 0.8 mg/kg; alternatively the maintenance dose may be 0.1 mg/kg to 0.6 mg/kg; alternatively the maintenance dose may be 0.1 mg/kg to 0.4 mg/kg; alternatively the maintenance dose may be 0.1 mg/kg to 0.2 mg/kg.

The loading dose may be 0.0001 mg/kg (mass of drug compared to mass of patient) to 20 mg/kg, and the maintenance dose may be between 0.0001 mg/kg to 20 mg/kg; alternatively the loading dose may be 0.001 mg/kg to 10 mg/kg, alternatively the loading dose may be 0.01 mg/kg to 2 mg/kg; alternatively the loading dose may be 0.1 mg/kg to 1 mg/kg; alternatively the loading dose may be 0.1 mg/kg to 1 mg/kg; alternatively the loading dose may be 0.2 mg/kg to 0.8 mg/kg; alternatively the loading dose may be 0.3 mg/kg to 0.6 mg/kg; alternatively the loading dose may be 0.4 mg/kg to 0.6 mg/kg, or 0.6 mg/kg-1.8 mg/kg.

The agent will generally be administered in conjunction with a pharmaceutically acceptable carrier. The term "pharmaceutically acceptable carrier", as used herein, includes genes, polypeptides, antibodies, liposomes, polysaccharides, polylactic acids, polyglycolic acids and inactive virus particles or indeed any other agent provided that the carrier does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. The pharmaceutical carrier employed will thus vary depending on the route of administration. Carriers may enable the pharmaceutical compositions to be formulated into tablets, pills, dragees, capsules, liquids, gels, syrups, slurries, suspensions to aid intake by the patient. A thorough discussion of pharmaceutically acceptable carriers is available in [42]. In a preferred embodiment the agent is administered in water or PBS.

The agent may be delivered by any known route of administration. The agent may be delivered locally or systemically. The agent may be delivered by a parenteral route (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications, needles, and hyposprays. Local administration includes topical administration, e.g. application to the skin, e.g. in the affected area. This may be of particular use in mild AIBD, e.g. mild BP.

Preferably the agent is delivered via subcutaneous injection. In some embodiments this is via once or twice daily subcutaneous injection, e.g. with an initial loading dose of between 0.0001 mg/kg (mass of drug compared to mass of patient) to 20 mg/kg, followed by once daily maintenance doses of between 0.0001 mg/kg to 20 mg/kg, or other doses disclosed elsewhere herein. Alternatively the agent may be delivered via subcutaneous injection every other day.

In a preferred embodiment the agent is delivered via once daily subcutaneous injection at an initial loading dose of 0.6 mg/kg-1.8 mg/kg (for example 0.57 mg/kg) followed by once daily maintenance doses of 0.2 mg/kg-0.6 mg/kg (for example 0.3 mg/kg), or via once daily subcutaneous injection at an initial loading dose of 0.6 mg/kg-3.6 mg/kg (for example 1.0 mg/kg) followed by once daily maintenance doses of 0.2 mg/kg-1.2 mg/kg (for example 0.6 mg/kg).

Preferably the course of treatment is continued for at least 1, 2, 3, 4, 5 or 6 weeks.

The course of treatment is preferably continued until the subject's symptoms have reduced. The course of treatment may thus be administration of the agent (e.g. daily) for at least 1, 2, 3, 4, 5, 6, 7, 8, 9, 10, 15, 20, 25, 30, 35, 40 weeks.

The maintenance dose (e.g. a single daily maintenance dose) may remain constant throughout the course of treatment) or the maintenance dose (e.g. a daily maintenance dose) may be modified (e.g. increased or decreased) during the course of treatment. The maintenance dose may be modified in order to maintain terminal complement activity at a desired level, e.g. 10% or less compared to serum from said patient in the absence of treatment or compared to normal control serum. The or each maintenance dose may be continued for at least 1, 2, 3, 4, 5, 6, 7, 8, 9, 10 weeks, e.g. daily for at least 1, 2, 3, 4, 5, 6, 7, 8, 9, 10 weeks. The maintenance dose may be decreased as the subject's symptoms improve. The amount of agent or the frequency with which the agent is administered may be decreased as the subject's symptoms improve.

There may thus be an initial loading dose, followed by an initial maintenance dose (e.g. a daily initial maintenance dose) which may be a maintenance dose as defined above, and one or more further maintenance doses (e.g. a daily further maintenance dose), e.g. at least 2, 3, 4, 5 further maintenance doses.

The invention thus further comprises a method of treating or preventing an AIBD, in a subject, comprising administering to the subject an initial loading dose of the agent as defined above, and then administering maintenance doses (e.g. daily maintenance doses) of the agent as defined above, wherein there is an initial maintenance dose and one or more further maintenance doses.

The invention thus further comprises an agent as defined above for use in a method of treating or preventing an AIBD in a subject, the method comprising administering to the subject an initial loading dose of the agent as defined above, and then administering maintenance doses (e.g. daily maintenance doses) of the agent as defined above, wherein there is an initial maintenance dose and one or more further maintenance doses.

The one or more further maintenance doses may be determined by testing the terminal complement activity in the subject (e.g. in a biological sample from the subject), and determining the further maintenance dose on the basis of the level of terminal complement activity and/or testing the subject's symptoms and determining the further maintenance dose on the basis of the symptoms. The method may optionally further comprise administering said further maintenance dose. Said further dose may be calculated to be at a level that maintains terminal complement activity at the desired level.

Where a biological sample is taken, this may be blood, e.g. a whole blood or a serum sample. The method optionally further comprises the step of taking the sample, and further optionally comprises the step of determining the TCA of the sample.

The one or more further maintenance doses may be determined by testing the terminal complement activity in the subject (e.g. in a biological sample), and determining the further maintenance dose on the basis of the level of terminal complement activity and/or testing the subject's symptoms and determining the further maintenance dose on the basis of the symptoms. The method may optionally further comprise administering said further maintenance dose. Said further dose may be calculated to be at a level that maintains terminal complement activity at the desired level.

In certain aspects, the desired complement activity level is 10% or less compared to serum from said subject in the absence of treatment or compared to normal control serum.

In certain aspects, if the TCA is higher than the desired level the maintenance dose is increased, and optionally wherein if TCA is less than 5, 4, 3, 2, 1% the dose is maintained or decreased.

In certain aspects, if the symptoms deteriorate the maintenance dose is increased, and optionally wherein if the symptoms improve the dose is maintained or decreased.

In some embodiments the subject is tested within one month of initiating the treatment, within two weeks of initiating the treatment, within a week of initiating the treatment. In other embodiments the subject is tested once a day or at least once a day, once a week, or at least once a week, once every two weeks or at least once every two weeks, once a month or once every two months.

Preferably the loading dose is 1.2 mg/kg or about 1.2 mg/kg protein or functional equivalent and the maintenance dose is at least 0.6 mg/kg (e.g. at least 0.7 mg/kg, 0.8-1.5, 0.9-1.2 or 1.0-1.25 mg/kg) or is up to 0.3 mg/kg (e.g. up to 0.2 mg/kg, 0.15-0.4, 0.2-0.3 mg/kg) and optionally (i) that maintenance dose is continued for at least 2, 3, 4, 5, 6 weeks and/or (ii) treatment is continued for at least 6 weeks and/or (iii) treatment is continued daily for at least 3, 4, 5, 6 weeks.

Preferably the loading dose is 0.6-1.8 mg/kg protein or functional equivalent and the maintenance dose is 0.2-0.6 mg/kg, e.g. about 0.3 mg/kg, and (i) that maintenance dose is continued for at least 2, 3, 4, 5, 6 weeks and/or (ii) treatment is continued for at least 6 weeks and/or (iii) treatment is continued daily for at least 3, 4, 5, 6 weeks.

The dosage regimen may also take the form of fixed dose not dependent on the weight of the subject being treated. The fixed dose may be administered as a single dose, or as one or more doses in a particular time frame. The fixed dose can be 1 mg-100 mg of Coversin (SEQ ID NO: 4) for typical human patients (e.g. those between 50 kg and 100 kg in weight). The molecular weight of Coversin-type proteins and modified Coversin polypeptides can be used to calculate equivalent fixed doses of functionally equivalent agents. In some embodiments, the fixed dose is between 1 mg-80 mg, 1 mg-50 mg, 5 mg-80 mg, 5 mg-50 mg, 10 mg-60 mg, 10 mg-50 mg, 20 mg-50 mg, 20 mg-40 mg or 25 mg-35 mg. Preferably the fixed dose is 30 mg of Coversin (SEQ ID NO: 4) or the molar equivalent of a Coversin-type protein or modified Coversin polypeptide. Typically, the fixed dose will be 1, 2, 3, 4 or 5 doses administered in a single 24 hour period. The fixed dose may be repeated at intervals, such as every 3, 4, 6, 8, 12, 24, or 48 hours. The precise regimen can be determined by routine experimentation, but may ultimately lie with the judgment of the clinician.

BRIEF DESCRIPTION OF FIGURES

FIG. 2A: Primary sequence of Coversin. Signal sequence underlined. Cysteine residues in bold type. Nucleotide (SEQ ID NO: 1) and amino acid (SEQ ID NO: 2) number indicated at right.

FIG. 2B: Examples of Coversin variants

FIG. 10 shows the sequence of certain modified Coversin polypeptides with reduced or absent C5-binding activity but which retain LTB-4-binding ability

EXAMPLES

Example 1

Effect of Coversin in EBA Transfer Model with Coversin Administered Prophylactically Antibody transfer EBA was induced using a modified version of the protocol described by Sitaru et al., 2005 [43]. Five mice were tested in each treatment group. Briefly, mice were injected subcutaneously with 50 µg affinity-purified anti-Col7 IgG on days 0, 2, and 4. Mice were injected subcutaneously twice daily with three varying doses of Coversin starting four days before the first injection of anti-Col7 IgG (day −2). This application was continued throughout the experiment until its last day on day 11. In the control groups the mice received only the vehicle subcutaneously, or 20 mg/kg methylprednisolone once daily.

To generate antibodies directed to murine type VII collagen ("anti-COL7"), New Zealand White rabbits were immunized with 200 µg of a protein mixture containing three different recombinant proteins ("Col7A, B, and C") derived from the non-collagenous 1 (NC1) domain of collagen VII together with incomplete Freund's adjuvant. IgGs were isolated from the serum of immunized rabbits by use of protein G, and afterwards IgGs were affinity-purified with his-Col7 to specifically obtain rabbit anti-Col7 IgG. Antibodies were quality checked by determining the titer and the potency in the cryosection assay.

Starting on day 4, the extent of skin lesions was scored in each individual mouse every other day. Skin areas exhibiting erythema, blisters, erosions, crusts, or alopecia were categorized as "affected" or "unaffected" by a trained observer [43]. The percentage of the total body surface affected by skin lesions (ABSA) was calculated.

Two independent experiments were conducted.

Figure 1:
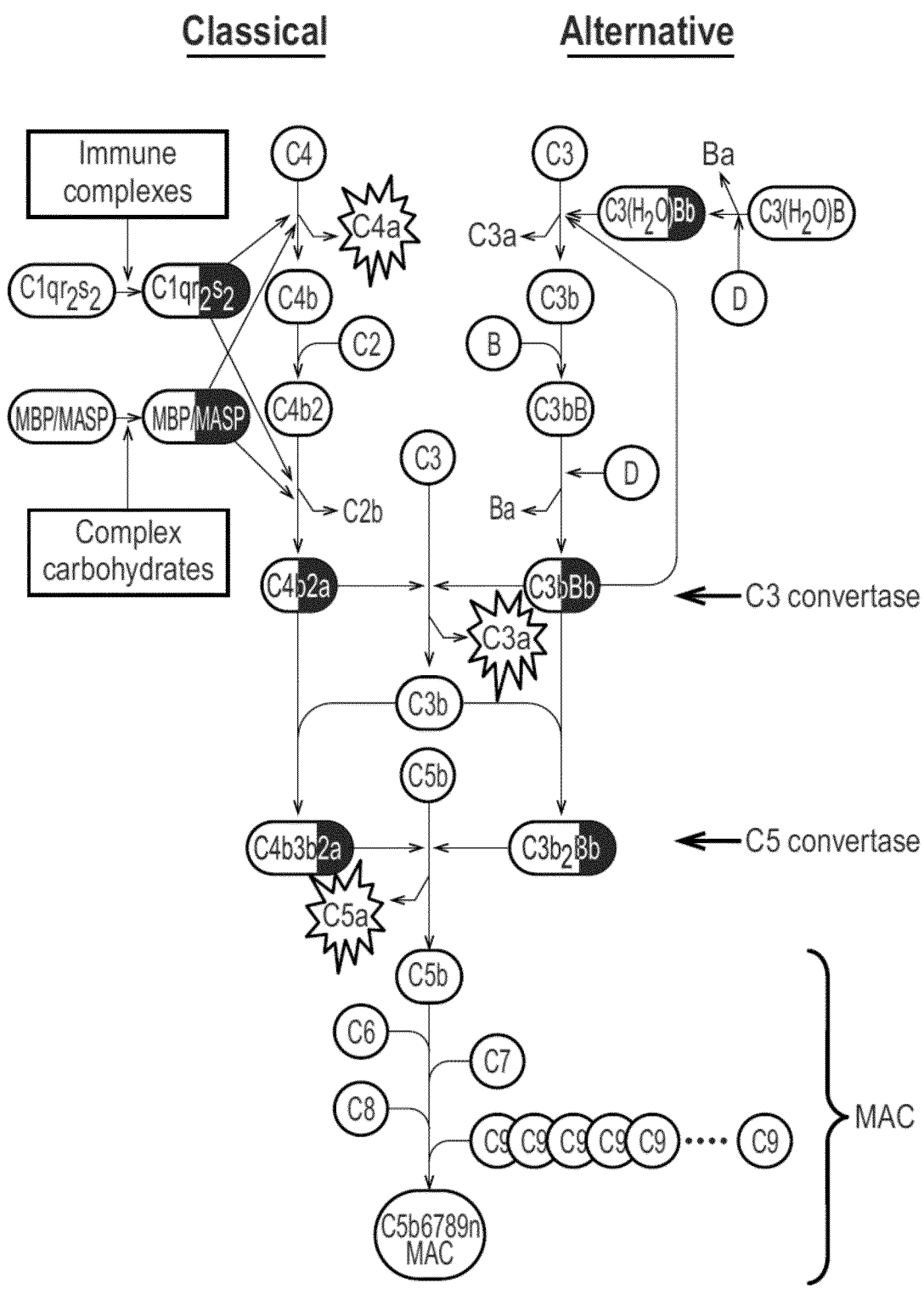
FIG. 1: Schematic diagram of classical and alternative pathways of complement activation. Enzymatic components, dark grey. Anaphylatoxins enclosed in starbursts.
Figure 3:
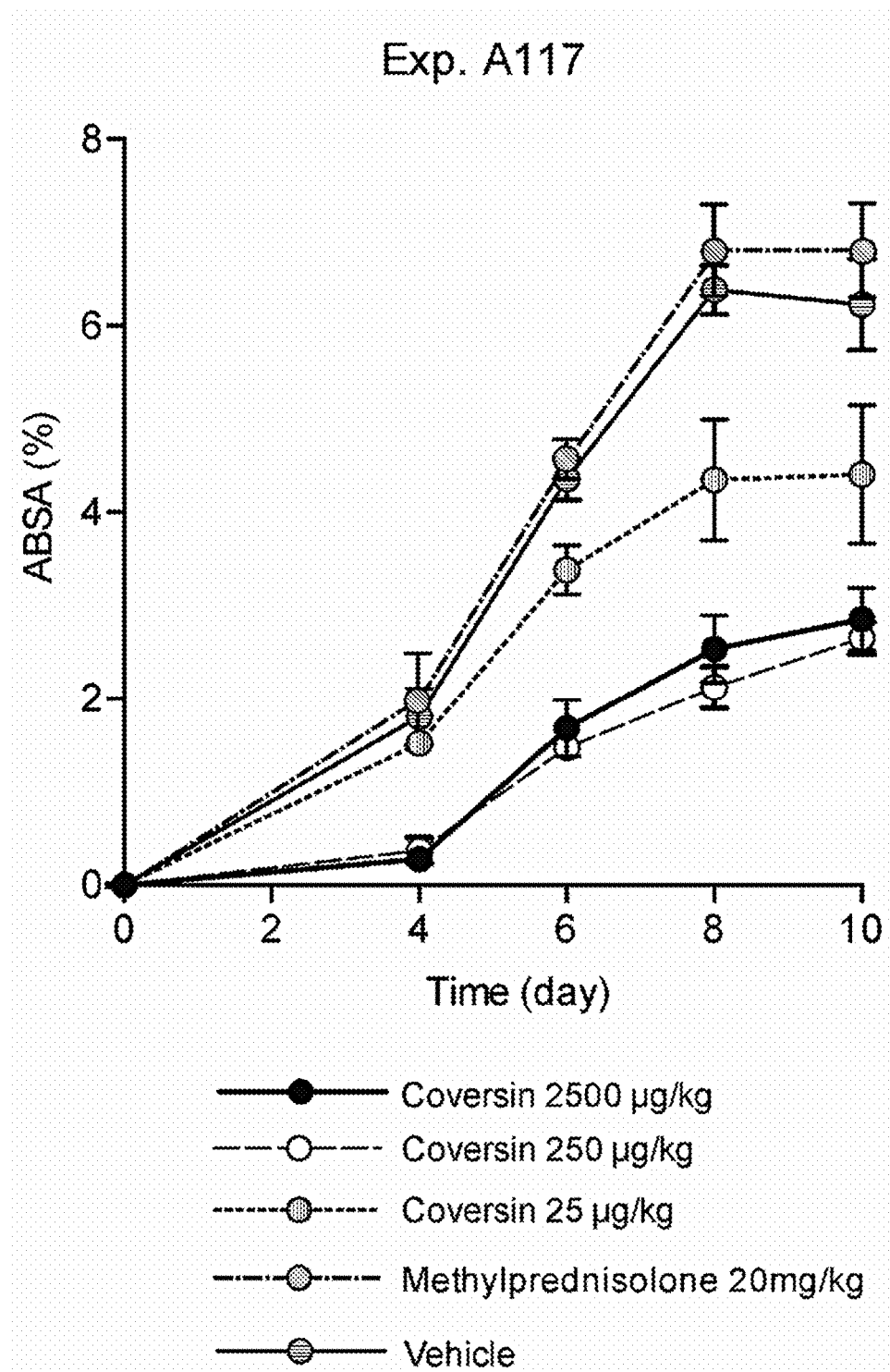
FIG. 3: Clinical score of experimental EBA in vehicle versus mice treated with prophylactic Coversin demonstrate ameliorated disease in mice treated with all doses of Coversin as compared to the vehicle control group and the methylprednisolone group, experiment 1.
Figure 4:
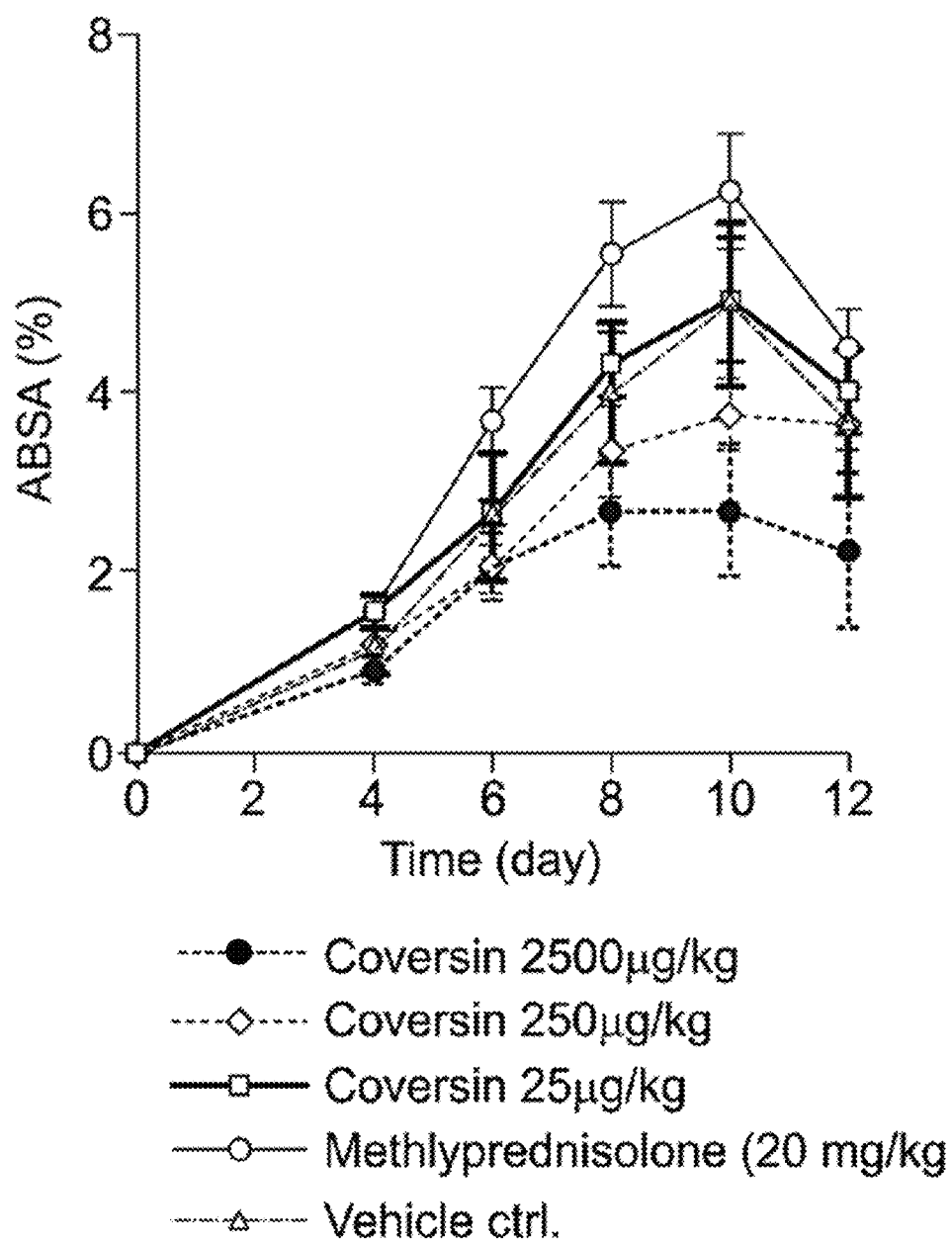
FIG. 4: Clinical score of experimental EBA in vehicle versus mice treated with prophylactic Coversin demonstrate ameliorated disease in mice treated with all doses of Coversin as compared to the vehicle control group and the methylprednisolone group, experiment 2. In comparison to the first experiment, Coversin only had a significant effect compared to the vehicle control group at the 2.5 mg/kg dose. Notably, in this experiment, several mice in the control group did not develop a significant level of disease, which is likely the reason for this difference compared to the first experiment.
Figure 5:
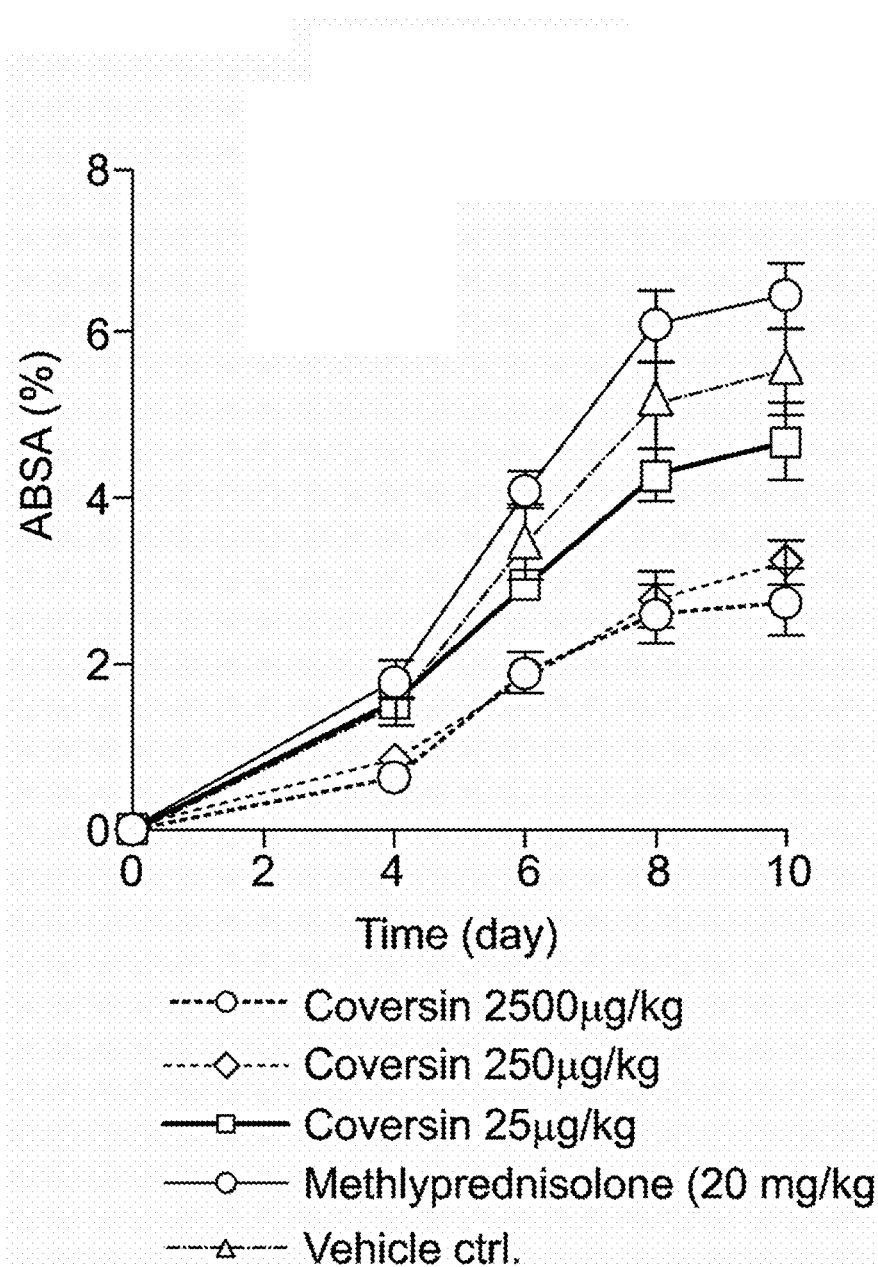
FIG. 5: Clinical score of experimental EBA in vehicle versus mice treated with prophylactic Coversin demonstrate ameliorated disease in mice treated with all doses of Coversin as compared to the vehicle control group and the methylprednisolone group, combined results of experiments 1 and 2, Two-way ANOVA analysis reveals a statistically significant difference between the vehicle control and Coversin in the doses of 250 and 2500 µg/ml.

The results of the first experiment are shown in FIG. 4. It can be seen that the percentage ABSA in mice treated with Coversin at 25 µg/kg was reduced, and that treatment with Coversin at Coversin 2500 µg/kg, and Coversin 250 µg/kg was further reduced. There was a 63% difference between vehicle and the 0.25 mg/kg dose. The P value for this difference by two tailed t-test is 0.0023. The mean ABSA scores for vehicle and 0.25 mg/kg dose at day 10 were 6.23+1.1 and 2.65+0.4. The values after the means are SDs.

Coversin reduced the percentage ABSA to a greater degree than previously tested molecules. For example, in previous similar experiments N-[1-(1-benzothien-2-yl) ethyl]-N-hydroxyurea (Zileuton), which is a 5-lipoxygenase inhibition (5-LO) oral inhibitor (an important enzyme of the arachidonic acid cascade and is involved in the formation of bioactive leukotrienes (LTs)) was administrated to C57Bl/6J 8-weeks-old female mice in a preventive dosing scheme. In this earlier experiment, mice were distributed into two groups and received 0.6-0.8 mg/mouse/day Zileuton or vehicle control supplemented into their drinking water. Experimental EBA was induced and evaluated [44]. The % ABSA was reduced, and it was concluded that "starting from day 7 of the experiment and until its end-point, mice treated with Zileuton exhibited a significantly reduced disease severity as compared to control group (clinical score day 7; control group: $X^-=9.2\pm0.7$; Zileuton treated group: $X^-=5.9\pm0.5\%$ of affected surface body area)".

In a similar earlier experiment in which 20 mg/kg/day of Methylprednisolone was administered in an antibody transfer model of EBA, 7.5±0.1% of the body surface area were affected by skin lesions in control mice at the end of the experiment, but this disease severity was significantly reduced to 4.7±0.4% in the Methylprednisolone treated mice [45].

Example 2

Effect of Coversin in EBA Transfer Model

The study included the following experimental groups, with 5 mice in each experimental group:
1. Vehicle (PBS) control group
2. 125 µg/kg Coversin 2× daily s.c.
3. 2500 µg/kg Coversin 2× daily s.c.

Antibody transfer EBA-like skin inflammation was induced, as described in Sezin et al [46]. Briefly, C57Bl/6J WT mice were injected subcutaneously (s.c.) with 50 µg affinity-purified anti-Col7 IgG on days 0, 2, and 4.

The treatment of mice with Coversin started on Day 5 of the experiment (Day 0=day of first administration of anti-COL7 antibody). Afterwards, mice were injected 12 hourly s.c. in the scapular region with Coversin or vehicle control until the end of the experiment.

Disease severity was scored. To score disease severity, skin areas exhibiting erythema, blisters, erosions, crusts, or alopecia were categorized as "affected" by a single trained examiner blinded to treatment. The percentage of the absolute body surface affected by skin lesions (ABSA) was calculated. To score the disease, the mice were anesthetized every other day with a mixture of ketamine/xylazine administered i.p. starting day 4 of the experiment.

Two independent experiments were conducted according to this protocol.

Test Item Preparation 18 mg of Coversin were reconstituted with 0.6 ml of sterile water to achieve a concentration of 30 mg/ml, aliquoted, and stored at −20° C. until final dilution.

Prior to the beginning of the experiment mean weight of the mice was calculated and 2.5 mg/kg and 0.125 mg/kg of the drug were prepared freshly to a final volume of 100 µl in PBS pH 7.2. The drug was prepared freshly, twice daily, 30 minutes before the final injection into the mice. Thereafter, based on the mean weight of the mice the drug was adjusted with PBS pH 7.2 to a concentration appropriate to provide the required mg/kg dose in a final volume of 100 µl. Drug was prepared freshly twice daily, 30 minutes before the final application into the animals. As a vehicle control 100 µl of PBS pH 7.2 was injected s.c into the mice.

Statistical Analysis

ABSA between treatment groups was evaluated by two-way ANOVA conducted using GraphPad Prism 7.

Results

Clinical Signs and Efficacy of Treatment

Figure 6A:
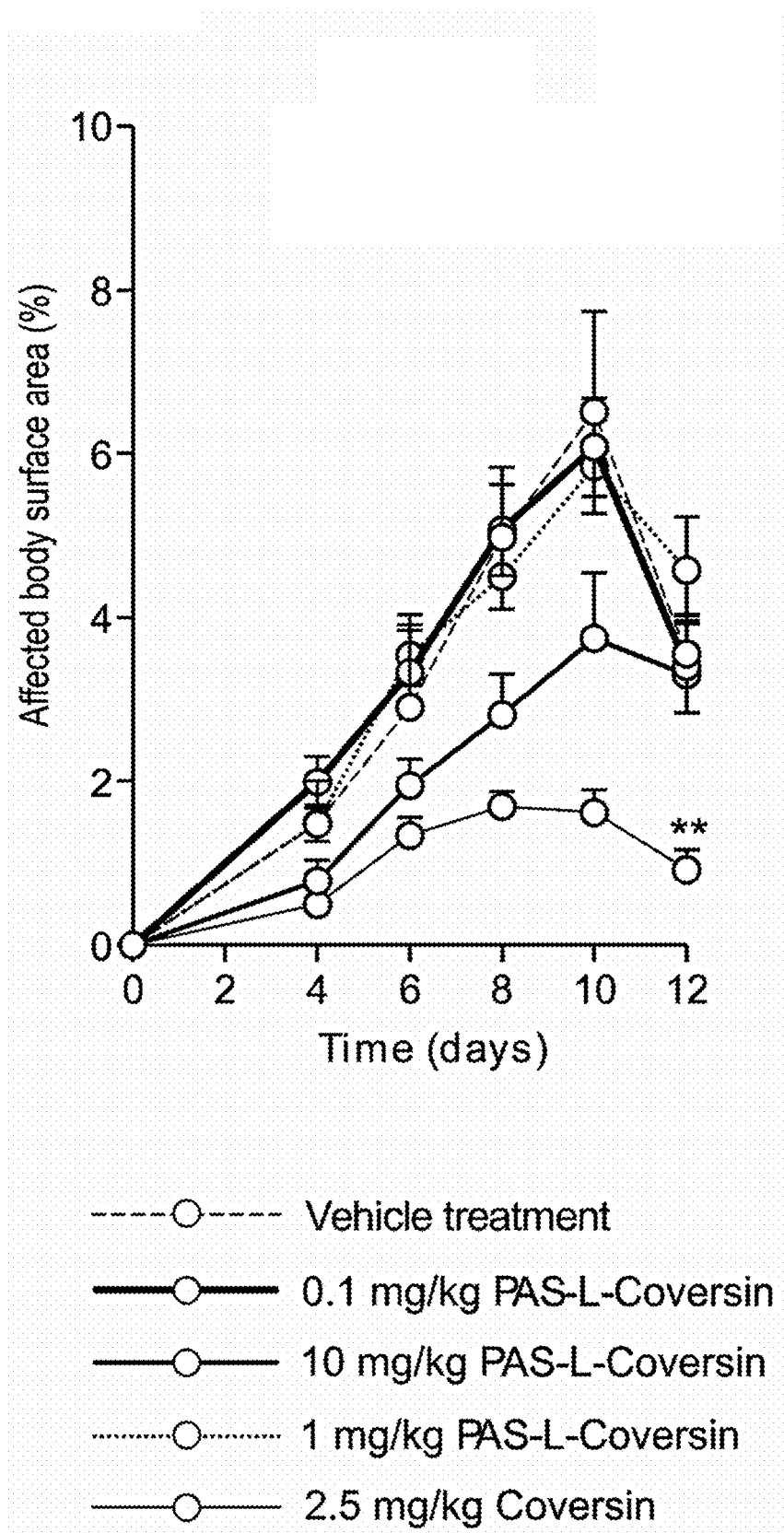
FIG. 6A: Clinical score of experimental EBA in vehicle versus mice treated with prophylactic Coversin and prophylactic PAS-L-Coversin demonstrate ameliorated disease in mice treated with 2.5 mg/kg Coversin (Example 4, experiment 1).
Figure 6B:
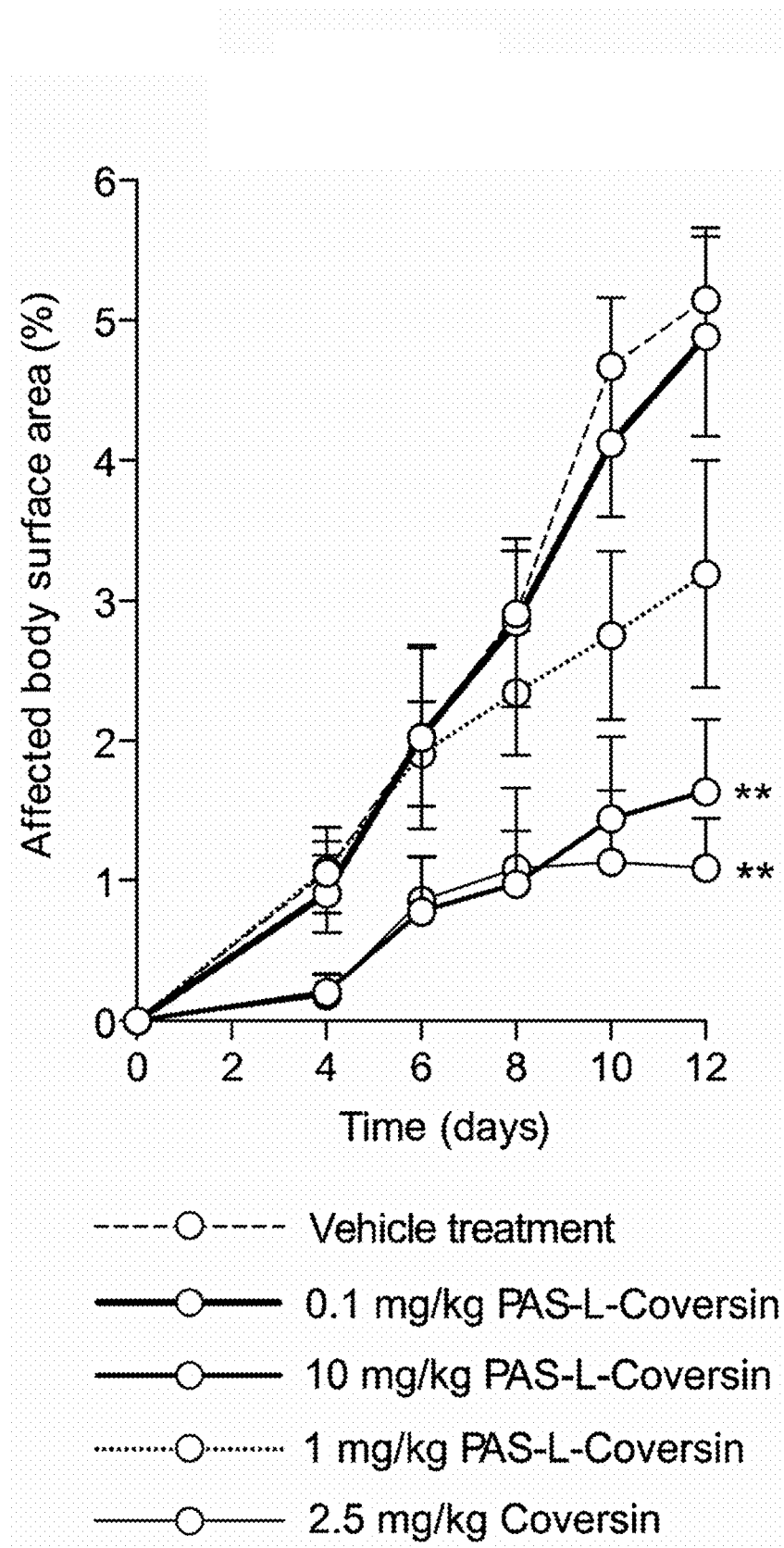
FIG. 6B: Clinical score of experimental EBA in vehicle versus mice treated with prophylactic Coversin and prophylactic PAS-L-Coversin demonstrate ameliorated disease in mice treated with 2.5 mg/kg Coversin (Example 4, experiment 2). Here the 10 mg/kg dose of PAS-L-Coversin and 2.5 mg/kg Coversin both show a statistically significant effect on ABSA.
Figure 6C:
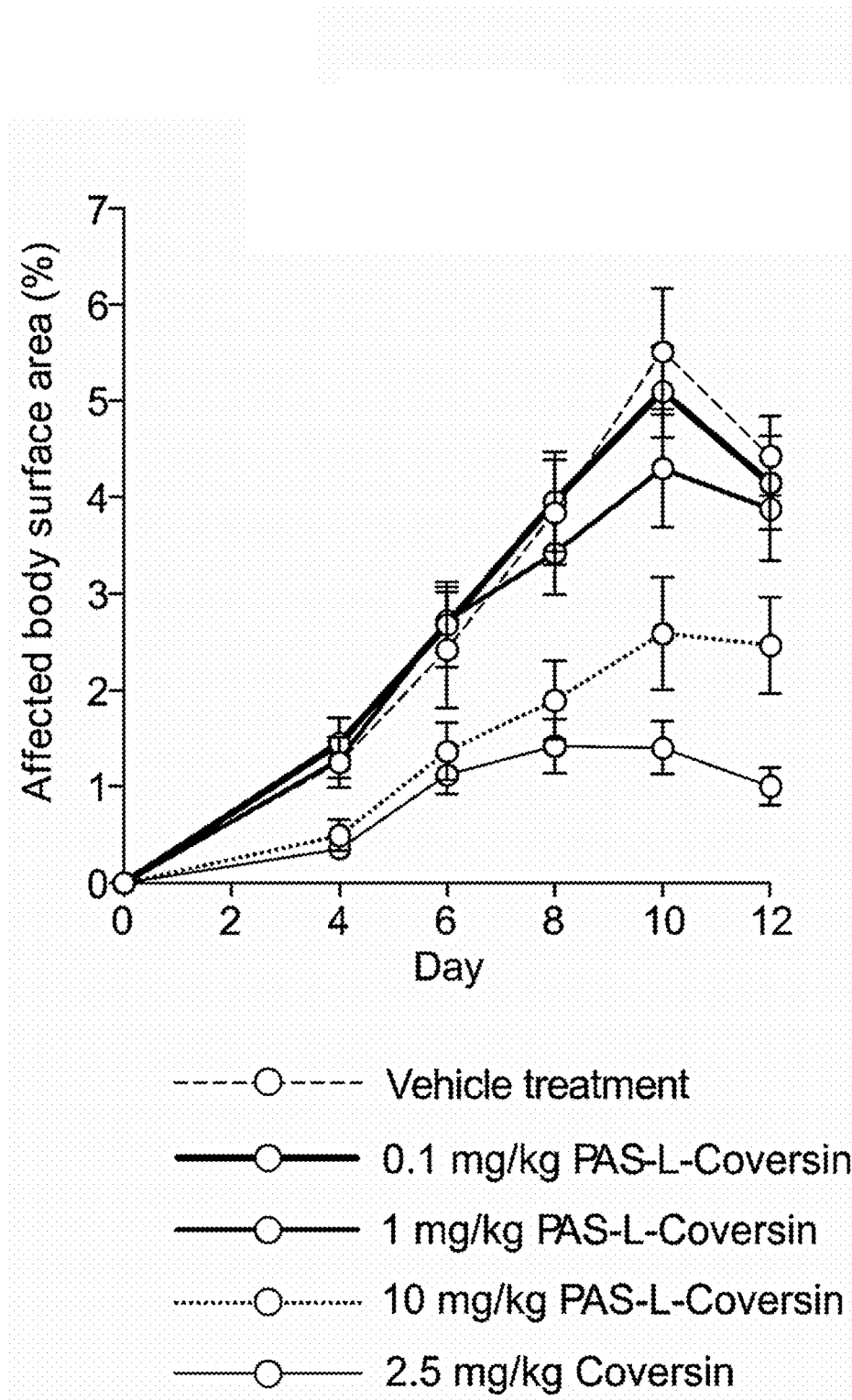
FIG. 6C: Clinical score of experimental EBA in vehicle versus mice treated with prophylactic Coversin and prophylactic PAS-L-Coversin. This shows the combined results of Example 4, experiments 1 and 2.
Figure 8:
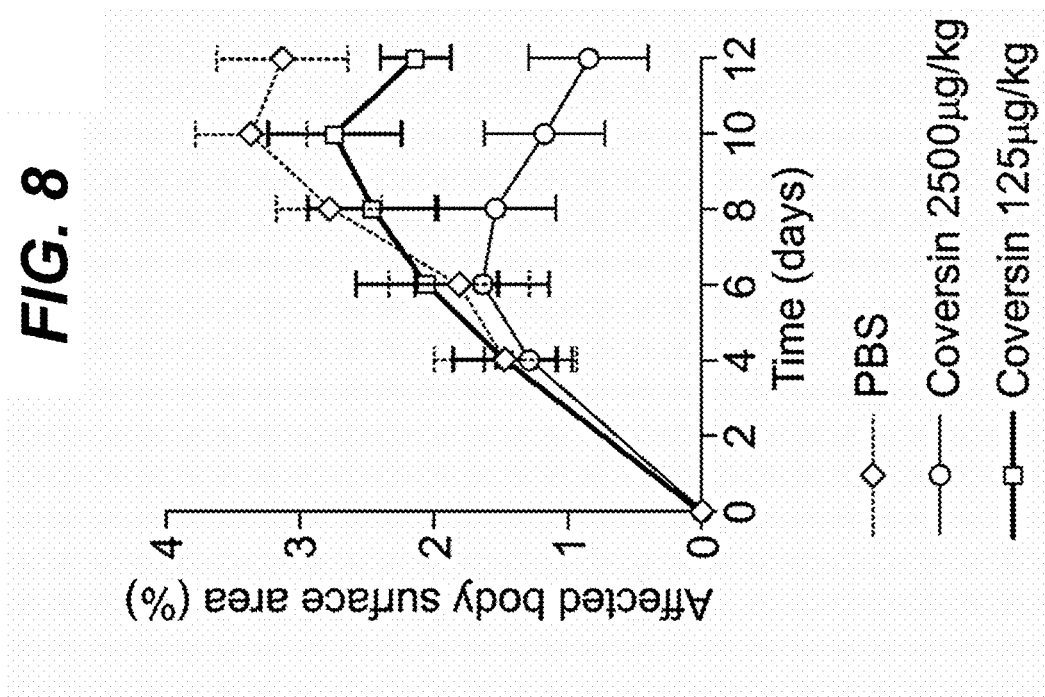
FIG. 8: Effect of therapeutically administered Coversin on the course of pemphigoid disease-like skin inflammation in the passive EBA mouse model (Example 2, experiment 2). Coversin dose-dependently ameliorated skin inflammation. Data are presented as means+/−SEM; N=5 mice per group; Two-way ANOVA testing for statistical significance confirms significant differences between the vehicle control and coversin in all doses used. The experiment was conducted exclusively in males.

In Experiment 1, Coversin dose-dependently ameliorated skin inflammation measured by absolute body surface area affected (ABSA). 2.5 mg/kg Coversin was effective in reducing ABSA (FIG. 6). The ABSA in the negative control (vehicle) group was about 7% in experiment 1, which is a typical value achieved in this model. All mice in the negative control group showed a similar inflammatory response.

Figure 7:
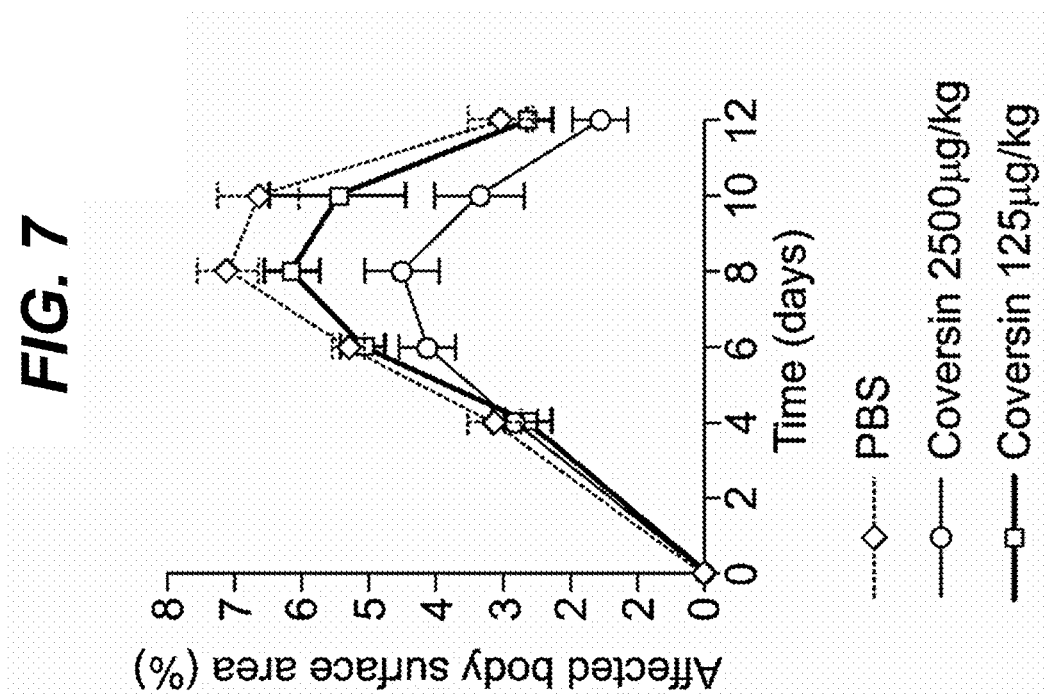
FIG. 7: Effect of therapeutically administered Coversin on the course of pemphigoid disease-like skin inflammation in the passive EBA mouse model (Example 2, experiment 1). Coversin dose-dependently ameliorated skin inflammation. Data are presented as means+/−SEM; N=5 mice per group; Two-way ANOVA testing for statistical significance confirms significant differences between the vehicle control and Coversin in all doses used. The experiment was conducted exclusively in females.

In Experiment 2, 2.5 mg/kg Coversin significantly (P<0.01) ameliorated skin inflammation measured by (ABSA) (FIG. 7). In this experiment, the ABSA in the negative control (vehicle) group peaked at a mean of about 4%, which is a little bit lower than the value mostly achieved in this model.

There were no deaths during treatment of mice in the two experiments. Mice were terminated on day 12 after initiation of Col7 IgG passive transfer.

Example 3 C5 and LTB4 in Blister Fluid of Patients

Figure 9A:
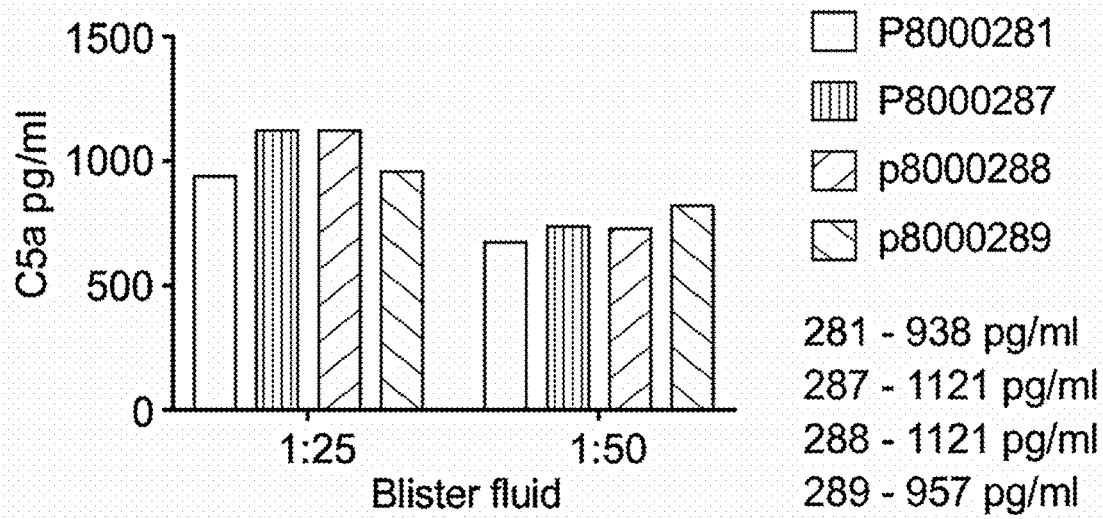
FIG. 9A shows C5a levels in blister fluid of bullous pemphigoid patients.
Figure 9B:
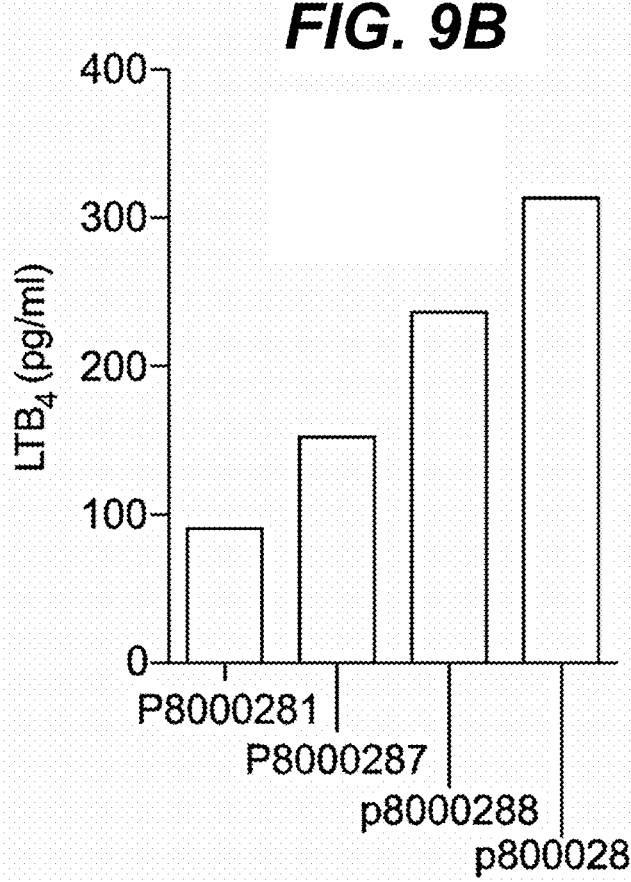
FIG. 9B shows LTB4 levels in blister fluid of bullous pemphigoid patients.

The levels of C5a and LTB4 in blister fluid from 4 bullous pemphigoid patients was tested. The results of each of the 4 patients are shown in FIGS. 9A (C5a) and 9B (LTB4). Blister fluid was aspirated with a syringe from blisters of four BP patients admitted to an inpatient clinic with acute BP. Samples were immediately frozen on liquid nitrogen. LTB4 and C5a levels were measured in the fluid using ELISA kits from R&D Systems.

Example 4

Comparison of Effect of Dual Action and Single Action Coversin

In a further experiment, the effect of PAS-L-Coversin was assessed. Mice were treated with 0.1 mg/kg, 10 mg/kg, 1 mg/kg PAS-L-Coversin, or 2.5 mg/kg Coversin, with the experiment being carried out as described above. PAS-L-Coversin has a PAS sequence fused to the N-terminus of the Coversin sequence, which has been mutated such that it binds LTB4 but does not bind C5 (referred to as "L-Coversin"). The sequence of the L-Coversin sequence is a variant of the mature Coversin sequence (SEQ ID NO: 4) in which the following residues have been modified: Ala44 to Asn, Met116 to Gln, Leu117 to Ser, Gly121 to Ala, Leu122 to Asp, Glu123 to Ala and Asp149 to Gly, (referred to as variant 2, sequence is dsesdctgse pvdafqafse gkeayvlvrs tdpkardclk gepNgekqdn tlpvmmtfkn gtdwastdwt ftldgakvta tlgnitqnre vvydsqshhc hvdkvekevp dyemwQSdag ADAveveccr qkleelasgr nqmyphlkGc (SEQ ID NO:23), where the changes relative to the native Coversin sequence of SEQ ID NO:4 are in capitals). Because of the higher molecule weight of the PAS-L-Cov, 10 mg/kg PAS-L-Cov corresponds to 2.5 mg/kg Coversin. In the first experiment (FIG. 6A) the 10 mg/kg dose but not 1 mg/kg or 0.1 mg/kg dose of PAS-L-Coversin reduced ABSA compared to control. In the second experiment (FIG. 6B), the 10 mg/kg dose and the 1 mg/kg but not the 0.1 mg/kg dose of PAS-L-Coversin reduced ABSA compared to control. The 10 mg/kg dose PAS-L-Coversin was not as effective as the molar equivalent 2.5 mg/kg dose of Coversin (although the 10 mg/kg dose of PAS-L-Coversin shows a statistically significant effect in the second experiment). This suggests that the dual inhibitory activity of Coversin (C5 and LTB4 inhibition) provides improved therapeutic benefit in this model.

REFERENCES

[1] Hoover et al, 1984, Proc. Nat. Acad. Sci. U.S.A. 81, 2191-2193
[2] Harrison and Murphy, 1995, J. Biol. Chem. 270, 17273-17276
[3] Ford-Hutchinson, 1990, Crit. Rev. Immunol. 10, 1-12
[4] Showell et al., 1995, J. Pharm. Exp. Ther. 273, 176-184
[5] Klaas et al, 2005 J. Exp. Med. 201, 1281-1292
[6] Del Prete et al, 2007 Blood, 109, 626-631
[7] Miyahara et al, 2006 Allergol Int. 55, 91-7
[8] Taube et al, 2006 J. Immunol. 176, 3157-3164
[9] Yamaoka et al, 1989 J. Immunol. 143, 1996-2000

[10] Yokomizo et al, 1997 Nature 387, 620-624

[11] Yokomizo et al, 2000 J. Exp. Med. 192, 421-432

[12] Tager and Luster, 2003 Prostaglandins Leukot. Essent. Fatty Acids 69, 123-134

[13] Yokomizo et al., 2001, J. Biol. Chem. 276, 12454-12459

[14] Kim, N. D. and Luster, A. D. (2007) The Scientific World Journal 7, 1307-1328.

[15] Kim et al., 2006. J. Exp. Med. 203, 829-835

[16] Noiri et al., 2000 Proc Nat Acad Sci USA 97, 823-828

[17] Lundeen et al., 2006. J. Immunol. 177, 3439-3447

[18] Shao et al, 2006. J. Immunol. 176, 6254-6261

[19] Chen et al., 2006. J. Exp. Med. 203, 837-842

[20] Sebaldt et al., 1990 Proc Natl Acad Sd. U.S.A. 8, 6974-6978

[21] Curry et al., 2005 Journal of the American Animal Hospital Association 41, 298-309

[22] Dube et al., 1998. Zileuton: the first leukotriene inhibitor for use in the management of chronic asthma. In: Drazen J M, Dahlen S, Lee T H, eds. Five-lipoxygenase Products in Asthma. New York, N.Y.: Marcel Dekkar, Inc

[23] Sharma and Mohammed, 2006 Immunopharmacology 14, 10-16

[24] Venning, V. A., British Journal of Dermatology, Volume 167, Issue 6, pages 1200-1214, December 2012

[25] WO2004/106369

[26] Ujiie, H., et al., J Immunol. 2014 Nov. 1; 193(9): 4415-28

[27] Sezin T, et al, The Journal of Investigative Dermatology (2017), doi: 10.1016/j.jid.2016.12.021.

[28] Schmidt, E. E., Dtsch Arztebl Int. 2011 June; 108 (23): 399-405.

[29] Bağci I S, et al, Bullous pemphigoid, Autoimmun Rev (2017), http://dx.doi.org/10.1016/j.autrev.2017.03.010

[30] Murrell et al Definitions and outcome measures for bullous pemphigoid: Recommendations by an international panel of experts. J Am Acad Dermatol. 2012 March; 66(3): 479-85

[31] Roversi, P et al Journal of Biological Chemistry 2013, 288(26) 18789-18802

[32] Guo, R. F. and P. A. Ward, Annu Rev Immunol, 2005, 23: p. 821-52

[33] Ricklin D & Lambris J, Nature Biotechnology, 25: 1265-1275 (2007)

[34] Nishimura, J et al., New Engl J. Med., 30;7: 632-639 (2014)

[35] Breustedt D. A., Schönfeld D. L., Skerra A. (2006) Comparative ligand-binding analysis of ten human lipocalins. Biochim Biophys Acta 1764(2):161-173.

[36] Terpe K, Appl Microbiol Biotechnol, 60: 523-33, 2003

[37] Schlapschy M, et al Protein Eng Des Sel. 2013 August; 26(8):489-501

[38] Kuhn et al Bioconjugate Chem., 2016, 27 (10), pp 2359-2371

[39] Sambrook et al (2000)

[40] Fernandez & Hoeffler (1998)

[41] Ausubel et al. (1991)

[42] Remington's Pharmaceutical Sciences; Mack Pub. Co., N.J. 1991

[43] Sitaru, C., et al. J Clin Invest 2005; 115:870-8.

[44] Sezin, T PhD thesis, Lubeck University 2016 http://www.zhb.uni-luebeck.de/epubs/ediss1702.pdf

[45] Hellberg, L., et al Journal of Investigative Dermatology (2013) 133, 2390-2399.

[46] Sezin T, Krajewski M, Wutkowski A, Mousavi S, Chakievska L, Bieber K, et al. The Leukotriene B4 and Its Receptor BLT1 Act as Critical Drivers of Neutrophil Recruitment in Murine Bullous Pemphigoid-Like Epidermolysis Bullosa Acquisita. J Invest Dermatol. 2017, 137(5): 1104-13.

The invention claimed is:

1. A method of treating an autoimmune blistering disease (AIBD) in a subject in need thereof, which comprises administering to the subject a therapeutically effective amount of an agent which is a protein comprising the sequence of amino acids 19 to 168 of the amino acid sequence of SEQ ID NO: 2 or a functional equivalent of this protein,
wherein the functional equivalent is:
a) a protein comprising a sequence having at least 90% sequence identity to the sequence of amino acids 19 to 168 of SEQ ID NO: 2; or
b) a fragment of a protein, the protein comprising a sequence having at least 90% sequence identity to the sequence of amino acids 19 to 168 of SEQ ID NO: 2,
and wherein the functional equivalent binds C5 to prevent the cleavage of complement C5 by convertase into complement C5a and complement C5b and binds to Leukotriene B4 (LTB4),
wherein the AIBD is bullous pemphigoid or epidermolysis bullosa acquisita (EBA).

2. A method of treating an autoimmune blistering disease (AIBD) in a subject in need thereof, which comprises administering to the subject a therapeutically effective amount of an agent which is a nucleic acid molecule encoding a protein comprising the sequence of amino acids 19 to 168 of the amino acid sequence of SEQ ID NO: 2 or a functional equivalent of this protein,
wherein the functional equivalent is:
a) a protein comprising a sequence having at least 90% sequence identity to the sequence of amino acids 19 to 168 of SEQ ID NO: 2; or
b) a fragment of a protein, the protein comprising a sequence having at least 90% sequence identity to the sequence of amino acids 19 to 168 of SEQ ID NO: 2,
and wherein the functional equivalent binds C5 to prevent the cleavage of complement C5 by convertase into complement C5a and complement C5b and binds to Leukotriene B4 (LTB4),
wherein the AIBD is bullous pemphigoid or epidermolysis bullosa acquisita (EBA).

3. The method of claim 1, wherein the agent is a protein comprising a sequence having at least 95% sequence identity to the sequence of amino acids 19 to 168 of SEQ ID NO: 2, and said protein binds C5 to prevent the cleavage of complement C5 by convertase into complement C5a and complement C5b and/or binds to LTB4.

4. The method of claim 1, wherein the agent is a protein comprising or consisting of the sequence of amino acids 19 to 168 of SEQ ID NO: 2.

5. The method of claim 1, wherein the agent is a protein comprising the sequence of amino acids 19 to 168 of SEQ ID NO: 2, in which up to 10 amino acid substitutions, insertions or deletions have been made,
and the protein binds C5 to prevent the cleavage of complement C5 by convertase into complement C5a and complement C5b and binds to LTB4.

6. The method of claim 1, wherein the agent is administered subcutaneously.

7. The method of claim 1, wherein the subject is a human.

8. The method of claim 1, wherein the agent is administered in a dose sufficient to bind as much available C5 and/or LTB4 as possible in the subject, or all available C5.

9. The method of claim 1, wherein the agent is administered in a dose 1.5 times the molar dose needed to bind all available C5 and/or LTB4 in the subject.

10. The method of claim 1, wherein the method comprises administering to the subject an initial loading dose of the agent and then administering maintenance doses thereof.

11. The method of claim 10, wherein there is an initial maintenance dose and one or more further maintenance doses.

12. The method of claim 1, wherein the method further comprises the administration of a second AIBD treatment.

13. The method of claim 12, wherein the second AIBD treatment is selected from systemic corticosteroid therapy, topical corticosteroid therapy, immunosuppressive therapy and immunosuppressive biological therapy.

14. The method of claim 13, wherein the corticosteroid is selected from prednisone and prednisolone, the immunosuppressive therapy is selected from methylprednisolone, mycophenolate, azathioprine, dapsone and cyclophosphamide and the immunosuppressive biological therapy is selected from rituximab and intravenous immunoglobulin G (IVIG).

15. The method of claim 1, wherein the AIBD is EBA.

16. The method of claim 1, wherein the functional equivalent of the protein comprising amino acids 19 to 168 of SEQ ID NO:2 is a fusion protein comprising (a) a sequence having at least 90% sequence identity to the sequence of amino acids 19 to 168 of SEQ ID NO: 2, and (b) a second sequence and said fusion protein binds C5 to prevent the cleavage of complement C5 by convertase into complement C5a and complement C5b and binds LTB4.

17. The method of claim 16, wherein said second sequence is a PAS sequence.

18. The method of claim 16, wherein said fusion protein comprises (a) a PAS sequence consisting of 30 copies of SEQ ID NO:15 and (b) (i) amino acids 19-168 of SEQ ID NO:2, wherein (a) is fused to the N terminus of (b).

19. The method of claim 13, wherein the corticosteroid is prednisone.

20. The method of claim 13, wherein the corticosteroid is prednisolone.

21. The method of claim 1, wherein the AIBD is bullous pemphigoid.

* * * * *

UNITED STATES PATENT AND TRADEMARK OFFICE
CERTIFICATE OF CORRECTION

PATENT NO. : 11,730,792 B2
APPLICATION NO. : 16/603352
DATED : August 22, 2023
INVENTOR(S) : Miles Nunn, Brihad Abhyankar and Christian David Sadik It is certified that error appears in the above-identified patent and that said Letters Patent is hereby corrected as shown below:

In the Claims

In Claim 3, at Column 56, Line 27, "and/or" should read --and--.

Signed and Sealed this
Third Day of October, 2023

Katherine Kelly Vidal
*Director of the United States Patent and Trademark Office*